US011737832B2

(12) United States Patent
Esposito et al.

(10) Patent No.: US 11,737,832 B2
(45) Date of Patent: Aug. 29, 2023

(54) VIEWING SYSTEM FOR USE IN A SURGICAL ENVIRONMENT

(71) Applicant: Magic Leap, Inc., Plantation, FL (US)

(72) Inventors: Jennifer Miglionico Esposito, Davie, FL (US); Daniel Andrew Garcia, Miami, FL (US); Manuela Tamayo, Boca Raton, FL (US); Emilio Patrick Shironoshita, Miami, FL (US); David Charles Lundmark, Los Altos, CA (US)

(73) Assignee: Magic Leap, Inc., Plantation, FL (US)

( * ) Notice: Subject to any disclaimer, the term of this patent is extended or adjusted under 35 U.S.C. 154(b) by 109 days.

(21) Appl. No.: 17/098,059

(22) Filed: Nov. 13, 2020

(65) Prior Publication Data

US 2021/0145525 A1    May 20, 2021

Related U.S. Application Data

(60) Provisional application No. 62/936,383, filed on Nov. 15, 2019.

(51) Int. Cl.
*A61B 34/20* (2016.01)
*G06T 11/00* (2006.01)
(Continued)

(52) U.S. Cl.
CPC .............. *A61B 34/20* (2016.02); *A61B 90/37* (2016.02); *G02B 27/0172* (2013.01);
(Continued)

(58) Field of Classification Search
CPC ................................ A61B 34/20; A61B 90/37
(Continued)

(56) References Cited

U.S. PATENT DOCUMENTS 4,344,092 A   8/1982   Miller
4,652,930 A   3/1987   Crawford
(Continued)

FOREIGN PATENT DOCUMENTS

CN   101449270 A   6/2009
CN   104040410 A   9/2014
(Continued)

OTHER PUBLICATIONS

Communication according to Rule 164(1) EPC dated Feb. 23, 2022, European Patent Application No. 20753144.3, (11 pages).
(Continued)

*Primary Examiner* — Javid A Amini
(74) *Attorney, Agent, or Firm* — Stephen M. De Klerk

(57) ABSTRACT

The invention relates to a viewing system for use in a surgical environment. Various real object detection devices detect locations of real objects in a real environment, such as a patient and body part of patient, medical staff, robots, a cutting tool on a robot, implant transferred by robot into body part, surgical tools, and disposable items. A map generator generates a map that forms a digital representation or a digital twin of the real environment. Various guiding modules including a room setup module, an anatomy registration module, a surgical planning module, and a surgical execution module make use of the digital representation to guide virtual or real objects based on the digital representation.

28 Claims, 57 Drawing Sheets

(51) Int. Cl.
   *G06F 3/01* (2006.01)
   *A61B 90/00* (2016.01)
   *G02B 27/01* (2006.01)
   *A61B 90/50* (2016.01)

(52) U.S. Cl.
   CPC .............. *G06F 3/011* (2013.01); *G06T 11/00* (2013.01); *A61B 2034/2057* (2016.02); *A61B 2034/2065* (2016.02); *A61B 2090/363* (2016.02); *A61B 2090/365* (2016.02); *A61B 2090/3614* (2016.02); *A61B 2090/502* (2016.02); *G06T 2210/41* (2013.01)

(58) Field of Classification Search
   USPC ........................................................ 345/156
   See application file for complete search history.

(56) References Cited

U.S. PATENT DOCUMENTS

| | | | |
|---|---|---|---|
| 4,810,080 | A | 3/1989 | Grendol et al. |
| 4,997,268 | A | 3/1991 | Dauvergne |
| 5,007,727 | A | 4/1991 | Kahaney et al. |
| 5,074,295 | A | 12/1991 | Willis |
| 5,240,220 | A | 8/1993 | Elberbaum |
| 5,251,635 | A | 10/1993 | Dumoulin et al. |
| 5,410,763 | A | 5/1995 | Bolle |
| 5,455,625 | A | 10/1995 | Englander |
| 5,495,286 | A | 2/1996 | Adair |
| 5,497,463 | A | 3/1996 | Stein et al. |
| 5,682,255 | A | 10/1997 | Friesem et al. |
| 5,826,092 | A | 10/1998 | Flannery |
| 5,854,872 | A | 12/1998 | Tai |
| 5,864,365 | A | 1/1999 | Sramek et al. |
| 5,937,202 | A | 8/1999 | Crosetto |
| 6,012,811 | A | 1/2000 | Chao et al. |
| 6,016,160 | A | 1/2000 | Coombs et al. |
| 6,064,749 | A | 5/2000 | Hirota et al. |
| 6,076,927 | A | 6/2000 | Owens |
| 6,117,923 | A | 9/2000 | Amagai et al. |
| 6,124,977 | A | 9/2000 | Takahashi |
| 6,191,809 | B1 | 2/2001 | Hori et al. |
| 6,375,369 | B1 | 4/2002 | Schneider et al. |
| 6,385,735 | B1 | 5/2002 | Wilson |
| 6,538,655 | B1 | 3/2003 | Kubota |
| 6,541,736 | B1 | 4/2003 | Huang et al. |
| 6,757,068 | B2 | 6/2004 | Foxlin |
| 7,046,515 | B1 | 5/2006 | Wyatt |
| 7,051,219 | B2 | 5/2006 | Hwang |
| 7,076,674 | B2 | 7/2006 | Cervantes |
| 7,111,290 | B1 | 9/2006 | Yates, Jr. |
| 7,119,819 | B1 | 10/2006 | Robertson et al. |
| 7,219,245 | B1 | 5/2007 | Raghuvanshi |
| 7,431,453 | B2 | 10/2008 | Hogan |
| 7,542,040 | B2 | 6/2009 | Templeman |
| 7,573,640 | B2 | 8/2009 | Nivon et al. |
| 7,724,980 | B1 | 5/2010 | Shenzhi |
| 7,751,662 | B2 | 7/2010 | Kleemann |
| 7,758,185 | B2 | 7/2010 | Lewis |
| 8,060,759 | B1 | 11/2011 | Arnan et al. |
| 8,120,851 | B2 | 2/2012 | Iwasa |
| 8,214,660 | B2 | 7/2012 | Capps, Jr. |
| 8,246,408 | B2 | 8/2012 | Elliot |
| 8,353,594 | B2 | 1/2013 | Lewis |
| 8,360,578 | B2 | 1/2013 | Nummela et al. |
| 8,508,676 | B2 | 8/2013 | Silverstein et al. |
| 8,547,638 | B2 | 10/2013 | Levola |
| 8,605,764 | B1 | 10/2013 | Rothaar et al. |
| 8,619,365 | B2 | 12/2013 | Harris et al. |
| 8,696,113 | B2 | 4/2014 | Lewis |
| 8,698,701 | B2 | 4/2014 | Margulis |
| 8,733,927 | B1 | 5/2014 | Lewis |
| 8,736,636 | B2 | 5/2014 | Kang |
| 8,759,929 | B2 | 6/2014 | Shiozawa et al. |
| 8,793,770 | B2 | 7/2014 | Lim |
| 8,823,855 | B2 | 9/2014 | Hwang |
| 8,847,988 | B2 | 9/2014 | Geisner et al. |
| 8,874,673 | B2 | 10/2014 | Kim |
| 9,010,929 | B2 | 4/2015 | Lewis |
| 9,015,501 | B2 | 4/2015 | Gee |
| 9,086,537 | B2 | 7/2015 | Iwasa et al. |
| 9,095,437 | B2 | 8/2015 | Boyden et al. |
| 9,239,473 | B2 | 1/2016 | Lewis |
| 9,244,293 | B2 | 1/2016 | Lewis |
| 9,244,533 | B2 | 1/2016 | Friend et al. |
| 9,383,823 | B2 | 7/2016 | Geisner et al. |
| 9,489,027 | B1 | 11/2016 | Ogletree |
| 9,519,305 | B2 | 12/2016 | Wolfe |
| 9,581,820 | B2 | 2/2017 | Robbins |
| 9,582,060 | B2 | 2/2017 | Balatsos |
| 9,658,473 | B2 | 5/2017 | Lewis |
| 9,671,566 | B2 | 6/2017 | Abovitz et al. |
| 9,671,615 | B1 | 6/2017 | Vallius et al. |
| 9,696,795 | B2 | 7/2017 | Marcolina et al. |
| 9,798,144 | B2 | 10/2017 | Sako et al. |
| 9,874,664 | B2 | 1/2018 | Stevens et al. |
| 9,880,441 | B1 | 1/2018 | Osterhout |
| 9,918,058 | B2 | 3/2018 | Takahas et al. |
| 9,955,862 | B2 | 5/2018 | Freeman et al. |
| 9,978,118 | B1 | 5/2018 | Ozgumer et al. |
| 9,996,797 | B1 | 6/2018 | Holz et al. |
| 10,018,844 | B2 | 7/2018 | Levola et al. |
| 10,082,865 | B1 | 9/2018 | Raynal et al. |
| 10,151,937 | B2 | 12/2018 | Lewis |
| 10,185,147 | B2 | 1/2019 | Lewis |
| 10,218,679 | B1 | 2/2019 | Jawahar |
| 10,241,545 | B1 | 3/2019 | Richards et al. |
| 10,317,680 | B1 | 6/2019 | Richards et al. |
| 10,436,594 | B2 | 10/2019 | Belt et al. |
| 10,516,853 | B1 | 12/2019 | Gibson et al. |
| 10,551,879 | B1 | 2/2020 | Richards et al. |
| 10,578,870 | B2 | 3/2020 | Kimmel |
| 10,698,202 | B2 | 6/2020 | Kimmel et al. |
| 10,856,107 | B2 | 10/2020 | Mycek et al. |
| 10,825,424 | B2 | 11/2020 | Zhang |
| 10,987,176 | B2 * | 4/2021 | Poltaretskyi ............ G06F 30/10 |
| 11,190,681 | B1 | 11/2021 | Brook et al. |
| 11,209,656 | B1 | 12/2021 | Choi et al. |
| 11,236,993 | B1 | 2/2022 | Hall et al. |
| 2001/0010598 | A1 | 8/2001 | Aritake et al. |
| 2002/0007463 | A1 | 1/2002 | Fung |
| 2002/0108064 | A1 | 2/2002 | Nunally |
| 2002/0063913 | A1 | 5/2002 | Nakamura et al. |
| 2002/0071050 | A1 | 6/2002 | Homberg |
| 2002/0122648 | A1 | 9/2002 | Mule' et al. |
| 2002/0140848 | A1 | 10/2002 | Cooper et al. |
| 2003/0028816 | A1 | 2/2003 | Bacon |
| 2003/0048456 | A1 | 3/2003 | Hill |
| 2003/0067685 | A1 | 4/2003 | Niv |
| 2003/0077458 | A1 | 4/2003 | Korenaga et al. |
| 2003/0115494 | A1 | 6/2003 | Cervantes |
| 2003/0218614 | A1 | 11/2003 | Lavelle et al. |
| 2003/0219992 | A1 | 11/2003 | Schaper |
| 2003/0226047 | A1 | 12/2003 | Park |
| 2004/0001533 | A1 | 1/2004 | Tran et al. |
| 2004/0021600 | A1 | 2/2004 | Wittenberg |
| 2004/0025069 | A1 | 2/2004 | Gary et al. |
| 2004/0042377 | A1 | 3/2004 | Nikoloai et al. |
| 2004/0073822 | A1 | 4/2004 | Greco |
| 2004/0073825 | A1 | 4/2004 | Itoh |
| 2004/0111248 | A1 | 6/2004 | Granny et al. |
| 2004/0174496 | A1 | 9/2004 | Ji et al. |
| 2004/0186902 | A1 | 9/2004 | Stewart |
| 2004/0201857 | A1 | 10/2004 | Foxlin |
| 2004/0238732 | A1 | 12/2004 | State et al. |
| 2004/0240072 | A1 | 12/2004 | Schindler et al. |
| 2004/0246391 | A1 | 12/2004 | Travis |
| 2004/0268159 | A1 | 12/2004 | Aasheim et al. |
| 2005/0001977 | A1 | 1/2005 | Zelman |
| 2005/0034002 | A1 | 2/2005 | Flautner |
| 2005/0157159 | A1 | 7/2005 | Komiya et al. |
| 2005/0177385 | A1 | 8/2005 | Hull |
| 2005/0231599 | A1 | 10/2005 | Yamasaki |
| 2005/0273792 | A1 | 12/2005 | Inohara et al. |

(56) References Cited

U.S. PATENT DOCUMENTS

| | | |
|---|---|---|
| 2006/0013435 A1 | 1/2006 | Rhoads |
| 2006/0015821 A1 | 1/2006 | Jacques Parker et al. |
| 2006/0019723 A1 | 1/2006 | Vorenkamp |
| 2006/0038880 A1 | 2/2006 | Starkweather et al. |
| 2006/0050224 A1 | 3/2006 | Smith |
| 2006/0090092 A1 | 4/2006 | Verhulst |
| 2006/0126181 A1 | 6/2006 | Levola |
| 2006/0129852 A1 | 6/2006 | Bonola |
| 2006/0132914 A1 | 6/2006 | Weiss et al. |
| 2006/0179329 A1 | 8/2006 | Terechko |
| 2006/0221448 A1 | 10/2006 | Nivon et al. |
| 2006/0228073 A1 | 10/2006 | Mukawa et al. |
| 2006/0250322 A1 | 11/2006 | Hall et al. |
| 2006/0259621 A1 | 11/2006 | Ranganathan |
| 2006/0268220 A1 | 11/2006 | Hogan |
| 2007/0058248 A1 | 3/2007 | Nguyen et al. |
| 2007/0103836 A1 | 5/2007 | Oh |
| 2007/0124730 A1 | 5/2007 | Pytel |
| 2007/0159673 A1 | 7/2007 | Freeman et al. |
| 2007/0188837 A1 | 8/2007 | Shimizu et al. |
| 2007/0198886 A1 | 8/2007 | Saito |
| 2007/0204672 A1 | 9/2007 | Huang et al. |
| 2007/0213952 A1 | 9/2007 | Cirelli |
| 2007/0283247 A1 | 12/2007 | Brenneman et al. |
| 2008/0002259 A1 | 1/2008 | Ishizawa et al. |
| 2008/0002260 A1 | 1/2008 | Arrouy et al. |
| 2008/0043334 A1 | 2/2008 | Itzkovitch et al. |
| 2008/0046773 A1 | 2/2008 | Ham |
| 2008/0063802 A1 | 3/2008 | Maula et al. |
| 2008/0068557 A1 | 3/2008 | Menduni et al. |
| 2008/0146942 A1 | 6/2008 | Dala-Krishna |
| 2008/0173036 A1 | 7/2008 | Williams |
| 2008/0177506 A1 | 7/2008 | Kim |
| 2008/0205838 A1 | 8/2008 | Crippa et al. |
| 2008/0215907 A1 | 9/2008 | Wilson |
| 2008/0225393 A1 | 9/2008 | Rinko |
| 2008/0316768 A1 | 12/2008 | Travis |
| 2009/0153797 A1 | 6/2009 | Allon et al. |
| 2009/0224416 A1 | 9/2009 | Laakkonen et al. |
| 2009/0245730 A1 | 10/2009 | Kleemann |
| 2009/0310633 A1 | 12/2009 | Ikegami |
| 2010/0005326 A1 | 1/2010 | Archer |
| 2010/0019962 A1 | 1/2010 | Fujita |
| 2010/0056274 A1 | 3/2010 | Uusitalo et al. |
| 2010/0063854 A1 | 3/2010 | Purvis et al. |
| 2010/0079841 A1 | 4/2010 | Levola |
| 2010/0153934 A1 | 6/2010 | Lachner |
| 2010/0194632 A1 | 8/2010 | Raento et al. |
| 2010/0232016 A1 | 9/2010 | Landa et al. |
| 2010/0232031 A1 | 9/2010 | Batchko et al. |
| 2010/0244168 A1 | 9/2010 | Shiozawa et al. |
| 2010/0277803 A1 | 11/2010 | Pockett et al. |
| 2010/0284085 A1 | 11/2010 | Laakkonen |
| 2010/0296163 A1 | 11/2010 | Sarikko |
| 2011/0021263 A1 | 1/2011 | Anderson et al. |
| 2011/0022870 A1 | 1/2011 | Mcgrane |
| 2011/0050640 A1 | 3/2011 | Lundback et al. |
| 2011/0050655 A1 | 3/2011 | Mukawa |
| 2011/0122240 A1 | 5/2011 | Becker |
| 2011/0145617 A1 | 6/2011 | Thomson et al. |
| 2011/0170801 A1 | 7/2011 | Lu et al. |
| 2011/0218733 A1 | 9/2011 | Hamza et al. |
| 2011/0286735 A1 | 11/2011 | Temblay |
| 2011/0291969 A1 | 12/2011 | Rashid et al. |
| 2012/0011389 A1 | 1/2012 | Driesen |
| 2012/0050535 A1 | 3/2012 | Densham et al. |
| 2012/0075501 A1 | 3/2012 | Oyagi et al. |
| 2012/0081392 A1 | 4/2012 | Arthur |
| 2012/0089854 A1 | 4/2012 | Breakstone |
| 2012/0113235 A1 | 5/2012 | Shintani |
| 2012/0127062 A1 | 5/2012 | Bar-Zeev et al. |
| 2012/0154557 A1 | 6/2012 | Perez et al. |
| 2012/0218301 A1 | 8/2012 | Miller |
| 2012/0246506 A1 | 9/2012 | Knight |
| 2012/0249416 A1 | 10/2012 | Maciocci et al. |
| 2012/0249741 A1 | 10/2012 | Maciocci et al. |
| 2012/0260083 A1 | 10/2012 | Andrews |
| 2012/0307075 A1 | 12/2012 | Margalitq |
| 2012/0307362 A1 | 12/2012 | Silverstein et al. |
| 2012/0314959 A1 | 12/2012 | White et al. |
| 2012/0320460 A1 | 12/2012 | Levola |
| 2012/0326948 A1 | 12/2012 | Crocco et al. |
| 2013/0021486 A1 | 1/2013 | Richardon |
| 2013/0050642 A1 | 2/2013 | Lewis et al. |
| 2013/0050833 A1 | 2/2013 | Lewis et al. |
| 2013/0051730 A1 | 2/2013 | Travers et al. |
| 2013/0502058 | 2/2013 | Liu et al. |
| 2013/0061240 A1 | 3/2013 | Yan et al. |
| 2013/0077049 A1 | 3/2013 | Bohn |
| 2013/0077170 A1 | 3/2013 | Ukuda |
| 2013/0094148 A1 | 4/2013 | Sloane |
| 2013/0129282 A1 | 5/2013 | Li |
| 2013/0162940 A1 | 6/2013 | Kurtin et al. |
| 2013/0169923 A1 | 7/2013 | Schnoll et al. |
| 2013/0205126 A1 | 8/2013 | Kruglick |
| 2013/0222386 A1 | 8/2013 | Tannhauser et al. |
| 2013/0268257 A1 | 10/2013 | Hu |
| 2013/0278633 A1 | 10/2013 | Ahn et al. |
| 2013/0314789 A1 | 11/2013 | Saarikko et al. |
| 2013/0318276 A1 | 11/2013 | Dalal |
| 2013/0336138 A1 | 12/2013 | Venkatraman et al. |
| 2013/0342564 A1 | 12/2013 | Kinnebrew et al. |
| 2013/0342570 A1 | 12/2013 | Kinnebrew et al. |
| 2013/0342571 A1 | 12/2013 | Kinnebrew et al. |
| 2013/0343408 A1 | 12/2013 | Cook |
| 2014/0013098 A1 | 1/2014 | Yeung |
| 2014/0016821 A1 | 1/2014 | Arth et al. |
| 2014/0022819 A1 | 1/2014 | Oh et al. |
| 2014/0078023 A1 | 3/2014 | Ikeda et al. |
| 2014/0082526 A1 | 3/2014 | Park et al. |
| 2014/0119598 A1 | 5/2014 | Ramachandran et al. |
| 2014/0126769 A1 | 5/2014 | Reitmayr et al. |
| 2014/0140653 A1 | 5/2014 | Brown et al. |
| 2014/0149573 A1 | 5/2014 | Tofighbakhsh et al. |
| 2014/0168260 A1 | 6/2014 | O'Brien et al. |
| 2014/0266987 A1 | 9/2014 | Magyari |
| 2014/0267419 A1 | 9/2014 | Ballard et al. |
| 2014/0274391 A1 | 9/2014 | Stafford |
| 2014/0282105 A1 | 9/2014 | Nordstrom |
| 2014/0313228 A1 | 10/2014 | Kasahara |
| 2014/0340449 A1 | 11/2014 | Plagemann et al. |
| 2014/0359589 A1 | 12/2014 | Kodsky et al. |
| 2014/0375680 A1 | 12/2014 | Ackerman et al. |
| 2015/0005785 A1 | 1/2015 | Olson |
| 2015/0009099 A1 | 1/2015 | Queen |
| 2015/0077312 A1 | 3/2015 | Wang |
| 2015/0097719 A1 | 4/2015 | Balachandreswaran et al. |
| 2015/0123966 A1 | 5/2015 | Newman |
| 2015/0130790 A1 | 5/2015 | Vazquez, II et al. |
| 2015/0134995 A1 | 5/2015 | Park et al. |
| 2015/0138248 A1 | 5/2015 | Schrader |
| 2015/0155939 A1 | 6/2015 | Oshima et al. |
| 2015/0168221 A1 | 6/2015 | Mao et al. |
| 2015/0205126 A1 | 7/2015 | Schowengerdt |
| 2015/0235427 A1 | 8/2015 | Nobori et al. |
| 2015/0235431 A1 | 8/2015 | Schowengerdt |
| 2015/0253651 A1 | 9/2015 | Russell et al. |
| 2015/0256484 A1 | 9/2015 | Cameron |
| 2015/0269784 A1 | 9/2015 | Miyawaki et al. |
| 2015/0294483 A1 | 10/2015 | Wells et al. |
| 2015/0301955 A1 | 10/2015 | Yakovenko et al. |
| 2015/0310657 A1 | 10/2015 | Eden |
| 2015/0338915 A1 | 11/2015 | Publicover et al. |
| 2015/0355481 A1 | 12/2015 | Hilkes et al. |
| 2016/0004102 A1 | 1/2016 | Nisper et al. |
| 2016/0015470 A1 | 1/2016 | Border |
| 2016/0027215 A1 | 1/2016 | Burns et al. |
| 2016/0033770 A1 | 2/2016 | Fujimaki et al. |
| 2016/0077338 A1 | 3/2016 | Robbins et al. |
| 2016/0085285 A1 | 3/2016 | Mangione-Smith |
| 2016/0085300 A1 | 3/2016 | Robbins et al. |
| 2016/0091720 A1 | 3/2016 | Stafford et al. |
| 2016/0093099 A1 | 3/2016 | Bridges |
| 2016/0093269 A1 | 3/2016 | Buckley et al. |

(56) References Cited

U.S. PATENT DOCUMENTS

| | | |
|---|---|---|
| 2016/0123745 A1 | 5/2016 | Cotier et al. |
| 2016/0155273 A1 | 6/2016 | Lyren et al. |
| 2016/0180596 A1 | 6/2016 | Gonzalez del Rosario |
| 2016/0187654 A1 | 6/2016 | Border et al. |
| 2016/0191887 A1 | 6/2016 | Casas |
| 2016/0202496 A1 | 7/2016 | Billetz et al. |
| 2016/0217624 A1 | 7/2016 | Finn et al. |
| 2016/0266412 A1 | 9/2016 | Yoshida |
| 2016/0267708 A1 | 9/2016 | Nistico et al. |
| 2016/0274733 A1 | 9/2016 | Hasegawa et al. |
| 2016/0287337 A1* | 10/2016 | Aram ............ A61B 34/10 |
| 2016/0300388 A1 | 10/2016 | Stafford et al. |
| 2016/0321551 A1 | 11/2016 | Priness et al. |
| 2016/0327798 A1 | 11/2016 | Xiao et al. |
| 2016/0334279 A1 | 11/2016 | Mittleman et al. |
| 2016/0357255 A1 | 12/2016 | Lindh et al. |
| 2016/0370404 A1 | 12/2016 | Quadrat et al. |
| 2016/0370510 A1 | 12/2016 | Thomas |
| 2017/0038607 A1 | 2/2017 | Camara |
| 2017/0060225 A1 | 3/2017 | Zha et al. |
| 2017/0061696 A1 | 3/2017 | Li et al. |
| 2017/0064066 A1 | 3/2017 | Das et al. |
| 2017/0100664 A1 | 4/2017 | Osterhout et al. |
| 2017/0102544 A1 | 4/2017 | Vallius et al. |
| 2017/0115487 A1 | 4/2017 | Travis |
| 2017/0122725 A1 | 5/2017 | Yeoh et al. |
| 2017/0123526 A1 | 5/2017 | Trail et al. |
| 2017/0127295 A1 | 5/2017 | Black et al. |
| 2017/0131569 A1 | 5/2017 | Aschwanden et al. |
| 2017/0147066 A1 | 5/2017 | Katz et al. |
| 2017/0160518 A1 | 6/2017 | Lanman et al. |
| 2017/0161951 A1 | 6/2017 | Fix et al. |
| 2017/0185261 A1 | 6/2017 | Perez et al. |
| 2017/0192239 A1 | 7/2017 | Nakamura et al. |
| 2017/0201709 A1 | 7/2017 | Igarashi et al. |
| 2017/0205903 A1 | 7/2017 | Miller et al. |
| 2017/0206668 A1 | 7/2017 | Poulos et al. |
| 2017/0213388 A1 | 7/2017 | Margolis et al. |
| 2017/0219841 A1 | 8/2017 | Popovich et al. |
| 2017/0232345 A1 | 8/2017 | Rofougaran et al. |
| 2017/0235126 A1 | 8/2017 | DiDomenico |
| 2017/0235129 A1 | 8/2017 | Kamakura |
| 2017/0235142 A1 | 8/2017 | Wall et al. |
| 2017/0235144 A1 | 8/2017 | Piskunov et al. |
| 2017/0235147 A1 | 8/2017 | Kamakura |
| 2017/0243403 A1 | 8/2017 | Daniels et al. |
| 2017/0246070 A1 | 8/2017 | Osterhout et al. |
| 2017/0254832 A1 | 9/2017 | Ho et al. |
| 2017/0256096 A1 | 9/2017 | Faaborg et al. |
| 2017/0258526 A1* | 9/2017 | Lang ............ A61B 34/74 |
| 2017/0266529 A1 | 9/2017 | Reikmoto |
| 2017/0270712 A1 | 9/2017 | Tyson et al. |
| 2017/0281054 A1 | 10/2017 | Stever et al. |
| 2017/0287376 A1 | 10/2017 | Bakar et al. |
| 2017/0293141 A1 | 10/2017 | Schowengerdt et al. |
| 2017/0307886 A1 | 10/2017 | Stenberg et al. |
| 2017/0307891 A1 | 10/2017 | Bucknor et al. |
| 2017/0312032 A1 | 11/2017 | Amanatullah et al. |
| 2017/0322418 A1 | 11/2017 | Liu |
| 2017/0322426 A1 | 11/2017 | Tervo |
| 2017/0329137 A1 | 11/2017 | Tervo |
| 2017/0332098 A1 | 11/2017 | Rusanovskyy et al. |
| 2017/0336636 A1 | 11/2017 | Amitai et al. |
| 2017/0357332 A1 | 12/2017 | Balan et al. |
| 2017/0363871 A1 | 12/2017 | Vallius |
| 2017/0371394 A1 | 12/2017 | Chan |
| 2017/0371661 A1 | 12/2017 | Sparling |
| 2018/0014266 A1 | 1/2018 | Chen |
| 2018/0024289 A1 | 1/2018 | Fattal |
| 2018/0044173 A1 | 2/2018 | Netzer |
| 2018/0052007 A1 | 2/2018 | Teskey et al. |
| 2018/0052501 A1 | 2/2018 | Jones, Jr. et al. |
| 2018/0059305 A1 | 3/2018 | Popovich et al. |
| 2018/0067779 A1 | 3/2018 | Pillalamarri et al. |
| 2018/0070855 A1 | 3/2018 | Eichler |
| 2018/0082480 A1* | 3/2018 | White ............ G06T 11/00 |
| 2018/0088185 A1 | 3/2018 | Woods et al. |
| 2018/0102981 A1 | 4/2018 | Kurtzman et al. |
| 2018/0108179 A1 | 4/2018 | Tomlin et al. |
| 2018/0114298 A1 | 4/2018 | Malaika et al. |
| 2018/0129112 A1 | 5/2018 | Osterhout |
| 2018/0131907 A1 | 5/2018 | Schmirler et al. |
| 2018/0136466 A1 | 5/2018 | Ko |
| 2018/0144691 A1 | 5/2018 | Choi et al. |
| 2018/0150971 A1 | 5/2018 | Adachi et al. |
| 2018/0151796 A1 | 5/2018 | Akahane |
| 2018/0172995 A1 | 6/2018 | Lee et al. |
| 2018/0188115 A1 | 7/2018 | Hsu et al. |
| 2018/0189568 A1 | 7/2018 | Powderly et al. |
| 2018/0190017 A1 | 7/2018 | Mendez et al. |
| 2018/0191990 A1 | 7/2018 | Motoyama et al. |
| 2018/0218545 A1 | 8/2018 | Garcia et al. |
| 2018/0250589 A1 | 9/2018 | Cossairt et al. |
| 2018/0284877 A1 | 10/2018 | Klein |
| 2018/0292654 A1 | 10/2018 | Wall et al. |
| 2018/0299678 A1 | 10/2018 | Singer et al. |
| 2018/0357472 A1 | 12/2018 | Dreessen |
| 2019/0005069 A1 | 1/2019 | Filgueiras De Araujo et al. |
| 2019/0011691 A1 | 1/2019 | Peyman |
| 2019/0056591 A1 | 2/2019 | Tervo et al. |
| 2019/0087015 A1 | 3/2019 | Lam et al. |
| 2019/0101758 A1 | 4/2019 | Zhu et al. |
| 2019/0107723 A1 | 4/2019 | Lee et al. |
| 2019/0137788 A1 | 5/2019 | Suen |
| 2019/0155034 A1 | 5/2019 | Singer et al. |
| 2019/0155439 A1 | 5/2019 | Mukherjee et al. |
| 2019/0158926 A1 | 5/2019 | Kang et al. |
| 2019/0167095 A1 | 6/2019 | Krueger |
| 2019/0172216 A1 | 6/2019 | Ninan et al. |
| 2019/0178654 A1 | 6/2019 | Hare |
| 2019/0196690 A1 | 6/2019 | Chong et al. |
| 2019/0206116 A1 | 7/2019 | Xu et al. |
| 2019/0219815 A1 | 7/2019 | Price et al. |
| 2019/0243123 A1 | 8/2019 | Bohn |
| 2019/0287270 A1 | 9/2019 | Nakamura et al. |
| 2019/0318502 A1 | 10/2019 | He et al. |
| 2019/0318540 A1 | 10/2019 | Piemonte et al. |
| 2019/0321728 A1 | 10/2019 | Imai et al. |
| 2019/0347853 A1 | 11/2019 | Chen et al. |
| 2019/0380792 A1* | 12/2019 | Poltaretskyi ......... G06K 9/6261 |
| 2019/0388182 A1 | 12/2019 | Kumar et al. |
| 2020/0066045 A1 | 2/2020 | Stahl et al. |
| 2020/0098188 A1 | 3/2020 | Bar-Zeev et al. |
| 2020/0100057 A1 | 3/2020 | Galon et al. |
| 2020/0110928 A1 | 4/2020 | Al Jazaery et al. |
| 2020/0117267 A1 | 4/2020 | Gibson et al. |
| 2020/0117270 A1 | 4/2020 | Gibson et al. |
| 2020/0184217 A1* | 6/2020 | Faulkner ............ G06T 7/50 |
| 2020/0184653 A1* | 6/2020 | Faulkner ............ G06T 7/40 |
| 2020/0202759 A1 | 6/2020 | Ukai et al. |
| 2020/0242848 A1 | 7/2020 | Ambler et al. |
| 2020/0309944 A1 | 10/2020 | Thoresen et al. |
| 2020/0356161 A1 | 11/2020 | Wagner |
| 2020/0368616 A1 | 11/2020 | Delamont |
| 2020/0391115 A1 | 12/2020 | Leeper et al. |
| 2020/0409528 A1 | 12/2020 | Lee |
| 2021/0008413 A1 | 1/2021 | Asikainen et al. |
| 2021/0033871 A1 | 2/2021 | Jacoby et al. |
| 2021/0041951 A1 | 2/2021 | Gibson et al. |
| 2021/0053820 A1 | 2/2021 | Gurin et al. |
| 2021/0093391 A1* | 4/2021 | Poltaretskyi ........... G16H 30/40 |
| 2021/0093410 A1* | 4/2021 | Gaborit ................ A61B 90/36 |
| 2021/0093414 A1* | 4/2021 | Moore ................. G16H 40/60 |
| 2021/0097886 A1* | 4/2021 | Kuester ................ A61B 5/1114 |
| 2021/0132380 A1 | 5/2021 | Wieczorek |
| 2021/0142582 A1 | 5/2021 | Jones et al. |
| 2021/0158627 A1 | 5/2021 | Cossairt et al. |
| 2021/0173480 A1 | 6/2021 | Osterhout et al. |
| 2022/0366598 A1 | 11/2022 | Azimi et al. |

FOREIGN PATENT DOCUMENTS

| | | |
|---|---|---|
| CN | 104603675 A | 5/2015 |
| CN | 106662754 A | 5/2017 |

(56) References Cited

FOREIGN PATENT DOCUMENTS

| | | |
|---|---|---|
| CN | 107683497 A1 | 2/2018 |
| CN | 105190427 B | 11/2019 |
| EP | 0504930 A1 | 3/1992 |
| EP | 0535402 A1 | 4/1993 |
| EP | 0632360 A1 | 1/1995 |
| EP | 1215522 A2 | 6/2002 |
| EP | 1494110 A2 | 1/2005 |
| EP | 1938141 A1 | 7/2008 |
| EP | 1943556 A2 | 7/2008 |
| EP | 2290428 A2 | 3/2011 |
| EP | 2350774 A1 | 8/2011 |
| EP | 1237067 B1 | 1/2016 |
| EP | 3139245 A1 | 3/2017 |
| EP | 3164776 B1 | 5/2017 |
| EP | 3236211 A1 | 10/2017 |
| EP | 2723240 B1 | 8/2018 |
| EP | 2896986 B1 | 2/2021 |
| GB | 2499635 A | 8/2013 |
| GB | 2542853 A | 4/2017 |
| IN | 938/DEL/2004 A | 6/2006 |
| JP | H03-036974 U | 4/1991 |
| JP | 2002-529806 | 9/2002 |
| JP | 2003-029198 A | 1/2003 |
| JP | 2003-141574 A | 5/2003 |
| JP | 2003-228027 A | 8/2003 |
| JP | 2003-329873 A | 11/2003 |
| JP | 2005-303843 A | 10/2005 |
| JP | 2007-012530 A | 1/2007 |
| JP | 2007-86696 A | 4/2007 |
| JP | 2007-273733 A | 10/2007 |
| JP | 2008-257127 A | 10/2008 |
| JP | 2009-090689 A | 4/2009 |
| JP | 2009-244869 A | 10/2009 |
| JP | 2011-033993 A | 2/2011 |
| JP | 2011-257203 A | 12/2011 |
| JP | 2012-015774 A | 1/2012 |
| JP | 2012-235036 A | 11/2012 |
| JP | 2013-525872 A1 | 6/2013 |
| JP | 2014-500522 A | 1/2014 |
| JP | 2015-191032 A | 11/2015 |
| JP | 2016-502120 A | 1/2016 |
| JP | 2016-85463 A | 5/2016 |
| JP | 2016-516227 A | 6/2016 |
| JP | 2017-015697 A | 1/2017 |
| JP | 2017-153498 | 9/2017 |
| JP | 2017-531840 A | 10/2017 |
| JP | 6232763 B2 | 11/2017 |
| JP | 6333965 B2 | 5/2018 |
| KR | 2005-0010775 A | 1/2005 |
| KR | 10-1372623 B1 | 3/2014 |
| TW | 201219829 A | 5/2012 |
| TW | 201803289 A | 1/2018 |
| WO | 1991/000565 A2 | 1/1991 |
| WO | 2000/030368 A1 | 6/2000 |
| WO | 2002/071315 A2 | 9/2002 |
| WO | 2004095248 A | 11/2004 |
| WO | 2006132614 A1 | 12/2006 |
| WO | 2007/037089 A1 | 5/2007 |
| WO | 2007/085682 A1 | 8/2007 |
| WO | 2007/102144 A1 | 9/2007 |
| WO | 2008148927 A1 | 12/2008 |
| WO | 2009/101238 A1 | 8/2009 |
| WO | 2014203440 A1 | 12/2010 |
| WO | 2012030787 A2 | 3/2012 |
| WO | 2013/049012 A1 | 4/2013 |
| WO | 2013062701 A1 | 5/2013 |
| WO | 2014033306 A1 | 3/2014 |
| WO | 2015/143641 A1 | 10/2015 |
| WO | 2015143641 A1 | 10/2015 |
| WO | 2016/054092 A1 | 4/2016 |
| WO | 2017004695 A1 | 1/2017 |
| WO | 2017044761 A1 | 3/2017 |
| WO | 2017049163 A1 | 3/2017 |
| WO | 2017120475 A1 | 7/2017 |
| WO | 2017176861 A1 | 10/2017 |
| WO | 2017/203201 A1 | 11/2017 |
| WO | 2018008232 A1 | 1/2018 |
| WO | 2018/031261 A1 | 2/2018 |
| WO | 2018022523 A1 | 2/2018 |
| WO | 2018/044537 A1 | 3/2018 |
| WO | 2018039273 A1 | 3/2018 |
| WO | 2018057564 A1 | 3/2018 |
| WO | 2018085287 A1 | 5/2018 |
| WO | 2018087408 A1 | 5/2018 |
| WO | 2018097831 A1 | 5/2018 |
| WO | 2018166921 A1 | 9/2018 |
| WO | 2019148154 A1 | 8/2019 |
| WO | 2020010226 A1 | 1/2020 |

OTHER PUBLICATIONS

Communication Pursuant to Article 94(3) EPC dated Jan. 4, 2022, European Patent Application No. 20154070.5, (8 pages).
Communication Pursuant to Article 94(3) EPC dated Oct. 21, 2021, European Patent Application No. 16207441.3, (4 pages).
Extended European Search Report dated Jan. 28, 2022, European Patent Application No. 19815876.8, (9 pages).
Extended European Search Report dated Jan. 4, 2022, European Patent Application No. 19815085.6, (9 pages).
Extended European Search Report dated Jun. 19, 2020, European Patent Application No. 20154750.2, (10 pages).
Extended European Search Report dated Mar. 22, 2022, European Patent Application No. 19843487.0, (14 pages).
Extended European Search Report dated Oct. 27, 2021, European Patent Application No. 19833664.6, (10 pages).
Extended European Search Report dated Sep. 20, 2021, European Patent Application No. 19851373.1, (8 pages).
Extended European Search Report dated Sep. 28, 2021, European Patent Application No. 19845418.3, (13 pages).
Final Office Action dated Feb. 23, 2022, U.S. Appl. No. 16/748,193, (23 pages).
Final Office Action dated Feb. 3, 2022, U.S. Appl. No. 16/864,721, (36 pages).
Final Office Action dated Sep. 17, 2021, U.S. Appl. No. 16/938,782, (44 pages).
First Office Action dated Mar. 14, 2022 with English translation, Chinese Patent Application No. 201880079474.6, (11 pages).
"Multi-core processor", TechTarget , 2013 , (1 page).
Non Final Office Action dated Apr. 1, 2022, U.S. Appl. No. 17/256,961, (65 pages).
Non Final Office Action dated Apr. 11, 2022, U.S. Appl. No. 16/938,782, (52 pages).
Non Final Office Action dated Apr. 12, 2022, U.S. Appl. No. 17/262,991, (60 pages).
Non Final Office Action dated Aug. 4, 2021, U.S. Appl. No. 16/864,721, (51 pages).
Non Final Office Action dated Feb. 2, 2022, U.S. Appl. No. 16/783,866, (8 pages).
Non Final Office Action dated Mar. 31, 2022, U.S. Appl. No. 17/257,814, (60 pages).
Non Final Office Action dated Mar. 9, 2022, U.S. Appl. No. 16/870,676, (57 pages).
Non Final Office Action dated Sep. 20, 2021, U.S. Appl. No. 17/105,848, (56 pages).
Non Final Office Action dated Sep. 29, 2021, U.S. Appl. No. 16/748,193, (62 pages).
Mrad , et al., "A framework for System Level Low Power Design Space Exploration", 1991.
"ARToolKit: Hardware", https://web.archive.org/web/20051013062315/http://www.hitl.washington.edu:80/artoolkit/documentation/hardware.htm (downloaded Oct. 26, 2020), Oct. 13, 2015, (3 pages).
Communication Pursuant to Article 94(3) EPC dated Sep. 4, 2019, European Patent Application No. 10793707.0, (4 pages).
Communication Pursuant to Rule 164(1) EPC, European Patent Application No. 19833664.6, (11 pages).
European Search Report dated Oct. 15, 2020, European Patent Application No. 20180623.9, (10 pages).

(56) References Cited

OTHER PUBLICATIONS

Examination Report dated Jun. 19, 2020, European Patent Application No. 20154750.2, (10 pages).
Extended European Search Report dated May 20, 2020, European Patent Application No. 20154070.5, (7 pages).
Extended European Search Report dated Jan. 22, 2021, European Patent Application No. 18890390.0, (11 pages).
Extended European Search Report dated Nov. 3, 2020, European Patent Application No. 18885707.2, (7 pages).
Extended European Search Report dated Jun. 30, 2021, European Patent Application No. 19811971.1, (9 pages).
Extended European Search Report dated Mar. 4, 2021, European Patent Application No. 19768418.6, (9 pages).
Extended European Search Report dated Nov. 4, 2020, European Patent Application No. 20190980.1, (14 pages).
Extended European Search Report dated Jun. 12, 2017, European Patent Application No. 16207441.3, (8 pages).
Extended European Search Report dated Jul. 16, 2021, European Patent Application No. 19810142.0, (14 pages).
Extended European Search Report dated Jul. 30, 2021, European Patent Application No. 19839970.1, (7 pages).
Final Office Action dated Aug. 10, 2020, U.S. Appl. No. 16/225,961, (13 pages).
Final Office Action dated Dec. 4, 2019, U.S. Appl. No. 15/564,517, (15 pages).
Final Office Action dated Feb. 19, 2020, U.S. Appl. No. 15/552,897, (17 pages).
Final Office Action dated Jun. 15, 2021, U.S. Appl. No. 16/928,313, (42 pages).
Final Office Action dated Mar. 1, 2021, U.S. Appl. No. 16/214,575, (29 pages).
Final Office Action dated Mar. 19, 2021, U.S. Appl. No. 16/530,776, (25 pages).
Final Office Action dated Nov. 24, 2020, U.S. Appl. No. 16/435,933, (44 pages).
International Search Report and Written Opinion dated Feb. 12, 2021, International Application No. PCT/US20/60555, (25 pages).
International Search Report and Written Opinion dated Mar. 12, 2020, International PCT Patent Application No. PCT/US19/67919, (14 pages).
International Search Report and Written Opinion dated Aug. 15, 2019, International PCT Patent Application No. PCT/US19/33987, (20 pages).
International Search Report and Written Opinion dated Jun. 15, 2020, International PCT Patent Application No. PCT/US2020/017023, (13 pages).
International Search Report and Written Opinion dated Oct. 16, 2019, International PCT Patent Application No. PCT/US19/43097, (10 pages).
International Search Report and Written Opinion dated Oct. 16, 2019, International PCT Patent Application No. PCT/US19/36275, (10 pages).
International Search Report and Written Opinion dated Oct. 16, 2019, International PCT Patent Application No. PCT/US19/43099, (9 pages).
International Search Report and Written Opinion dated Jun. 17, 2016, International PCT Patent Application No. PCT/FI2016/050172, (9 pages).
International Search Report and Written Opinion dated Feb. 2, 2021, International PCT Patent Application No. PCT/US20/60550, (9 pages).
International Search Report and Written Opinion dated Oct. 22, 2019, International PCT Patent Application No. PCT/US19/43751, (9 pages).
International Search Report and Written Opinion dated Dec. 23, 2019, International PCT Patent Application No. PCT/US19/44953, (11 pages).
International Search Report and Written Opinion dated May 23, 2019, International PCT Patent Application No. PCT/US18/66514, (17 pages).
International Search Report and Written Opinion dated Sep. 26, 2019, International PCT Patent Application No. PCT/US19/40544, (12 pages).
International Search Report and Written Opinion dated Aug. 27, 2019, International PCT Application No. PCT/US2019/035245, (8 pages).
International Search Report and Written Opinion dated Dec. 27, 2019, International Application No. PCT/US19/47746, (16 pages).
International Search Report and Written Opinion dated Dec. 3, 2020, International Patent Application No. PCT/US20/43596, (25 pages).
International Search Report and Written Opinion dated Sep. 30, 2019, International Patent Application No. PCT/US19/40324, (7 pages).
International Search Report and Written Opinion dated Sep. 4, 2020, International Patent Application No. PCT/US20/31036, (13 pages).
International Search Report and Written Opinion dated Jun. 5, 2020, International Patent Application No. PCT/US20/19871, (9 pages).
International Search Report and Written Opinion dated Aug. 8, 2019, International PCT Patent Application No. PCT/US2019/034763, (8 pages).
International Search Report and Written Opinion dated Oct. 8, 2019, International PCT Patent Application No. PCT/US19/41151, (7 pages).
International Search Report and Written Opinion dated Jan. 9, 2020, International Application No. PCT/US19/55185, (10 pages).
International Search Report and Written Opinion dated Feb. 28, 2019, International Patent Application No. PCT/US18/64686, (8 pages).
International Search Report and Written Opinion dated Feb. 7, 2020, International PCT Patent Application No. PCT/US2019/061265, (11 pages).
International Search Report and Written Opinion dated Jun. 11, 2019, International PCT Application No. PCT/US19/22620, (7 pages).
Invitation to Pay Additional Fees dated Aug. 15, 2019, International PCT Patent Application No. PCT/US19/36275, (2 pages).
Invitation to Pay Additional Fees dated Sep. 24, 2020, International Patent Application No. PCT/US2020/043596, (3 pages).
Invitation to Pay Additional Fees dated Oct. 22, 2019, International PCT Patent Application No. PCT/US19/47746, (2 pages).
Invitation to Pay Additional Fees dated Apr. 3, 2020, International Patent Application No. PCT/US20/17023, (2 pages).
Invitation to Pay Additional Fees dated Oct. 17, 2019, International PCT Patent Application No. PCT/US19/44953, (2 pages).
Non Final Office Action dated Aug. 21, 2019, U.S. Appl. No. 15/564,517, (14 pages).
Non Final Office Action dated Jan. 26, 2021, U.S. Appl. No. 16/928,313, (33 pages).
Non Final Office Action dated Jan. 27, 2021, U.S. Appl. No. 16/225,961, (15 pages).
Non Final Office Action dated Jul. 27, 2020, U.S. Appl. No. 16/435,933, (16 pages).
Non Final Office Action dated Jul. 9, 2021, U.S. Appl. No. 17/002,663, (43 pages).
Non Final Office Action dated Jul. 9, 2021, U.S. Appl. No. 16/833,093, (47 pages).
Non Final Office Action dated Jun. 10, 2021, U.S. Appl. No. 16/938,782, (40 Pages).
Non Final Office Action dated Jun. 17, 2020, U.S. Appl. No. 16/682,911, (22 pages).
Non Final Office Action dated Jun. 19, 2020, U.S. Appl. No. 16/225,961, (35 pages).
Non Final Office Action dated Mar. 3, 2021, U.S. Appl. No. 16/427,337, (41 pages).
Non Final Office Action dated May 26, 2021, U.S. Appl. No. 16/214,575, (19 pages).
Non Final Office Action dated Nov. 19, 2019, U.S. Appl. No. 16/355,611, (31 pages).
Non Final Office Action dated Nov. 5, 2020, U.S. Appl. No. 16/530,776, (45 pages).
Non Final Office Action dated Jun. 29, 2021, U.S. Appl. No. 16/698,588, (58 pages).

(56) References Cited

OTHER PUBLICATIONS

Non Final Office Action dated Oct. 22, 2019, U.S. Appl. No. 15/859,277, (15 pages).
Non Final Office Action dated Sep. 1, 2020, U.S. Appl. No. 16/214,575, (40 pages).
Notice of Allowance dated Mar. 25, 2020, U.S. Appl. No. 15/564,517, (11 pages).
Notice of Allowance dated Oct. 5, 2020, U.S. Appl. No. 16/682,911, (27 pages).
Notice of Reason of Refusal dated Sep. 11, 2020 with English translation, Japanese Patent Application No. 2019-140435, (6 pages).
"Phototourism Challenge", CVPR 2019 Image Matching Workshop. https://image matching-workshop.github.io., (16 pages).
Summons to attend oral proceedings pursuant to Rule 115(1) EPC mailed Jul. 15, 2019, European Patent Application No. 15162521.7, (7 pages).
Aarik, J. et al., "Effect of crystal structure on optical properties of TiO2 films grown by atomic layer deposition", Thin Solid Films; Publication [online]. May 19, 1998 [retrieved Feb. 19, 2020], Retrieved from the Internet: <URL: https://www.sciencedirect.com/science/article/pii/S0040609097001351?via%3Dihub>; DOI: 10.1016/50040-6090(97)00135-1; see entire document, (2 pages).
Altwaijry, et al., "Learning to Detect and Match Keypoints with Deep Architectures", Proceedings of the British Machine Vision Conference (BMVC), BMVA Press, Sep. 2016, [retrieved on Jan. 8, 2021 (Jan. 8, 2021 )] < URL: http://www.bmva.org/bmvc/2016/papers/paper049/index.html >, en lire document, especially Abstract, pp. 1-6 and 9.
Arandjelović, Relja et al., "Three things everyone should know to improve object retrieval", CVPR, 2012, (8 pages).
Azom, , "Silica—Silicon Dioxide (SiO2)", AZO Materials; Publication [Online], Dec. 13, 2001 [retrieved Feb. 19, 2020], Retrieved from the Internet: <URL https://www.azom.com/article.aspx?Article1D=1114>, (6 pages).
Azuma, Ronald T. , "A Survey of Augmented Reality", Presence: Teleoperators and Virtual Environments 6, 4 (Aug. 1997), 355-385; https://web.archive.org/web/20010604100006/http://www.cs.unc.edu/~azuma/ARpresence.pdf (downloaded Oct. 26, 2020).
Azuma, Ronald T. , "Predictive Tracking for Augmented Reality", Department of Computer Science, Chapel Hill NC; TR95-007, Feb. 1995, 262 pages.
Battaglia, Peter W. et al., "Relational inductive biases, deep learning, and graph networks", arXiv:1806.01261, Oct. 17, 2018, pp. 1-40.
Berg, Alexander C et al., "Shape matching and object recognition using low distortion correspondences", In CVPR, 2005, (8 pages).
Bian, Jiawang et al., "GMS: Grid-based motion statistics for fast, ultra-robust feature correspondence.", In CVPR (Conference on Computer Vision and Pattern Recognition), 2017, (10 pages).
Bimber, Oliver et al., "Spatial Augmented Reality: Merging Real and Virtual Worlds", https://web.media.mit.edu/~raskar/book/BimberRaskarAugmentedRealityBook.pdf; published by A K Peters/CRC Press (Jul. 31, 2005); eBook (3rd Edition, 2007), (393 pages).
Brachmann, Eric et al., "Neural-Guided RANSAC: Learning Where to Sample Model Hypotheses", In ICCV (International Conference on Computer Vision ), arXiv:1905.04132v2 [cs.CV] Jul. 31, 2019, (17 pages).
Butail, et al., "Putting the fish in the fish tank: Immersive VR for animal behavior experiments", In: 2012 IEEE International Conference on Robotics and Automation. May 18, 2012 (May 18, 2012) Retrieved on Nov. 14, 2020 (Nov. 14, 2020) from <http:/lcdcl.umd.edu/papers/icra2012.pdf> entire document, (8 pages).
Caetano, Tibério S et al., "Learning graph matching", IEEE TPAMI, 31(6):1048-1058, 2009.
Cech, Jan et al., "Efficient sequential correspondence selection by cosegmentation", IEEE TPAMI, 32(9):1568-1581, Sep. 2010.
Cuturi, Marco , "Sinkhorn distances: Lightspeed computation of optimal transport", NIPS, 2013, (9 pages).

Dai, Angela et al., "ScanNet: Richly-annotated 3d reconstructions of indoor scenes", In CVPR, arXiv:1702.04405v2 [cs.CV] Apr. 11, 2017, (22 pages).
Deng, Haowen et al., "PPFnet: Global context aware local features for robust 3d point matching", In CVPR, arXiv:1802.02669v2 [cs.CV] Mar. 1, 2018, (12 pages).
Detone, Daniel et al., "Deep image homography estimation", In RSS Work-shop: Limits and Potentials of Deep Learning in Robotics, arXiv:1606.03798v1 [cs.CV] Jun. 13, 2016, (6 pages).
Detone, Daniel et al., "Self-improving visual odometry", arXiv:1812.03245, Dec. 8, 2018, (9 pages).
Detone, Daniel et al., "SuperPoint: Self-supervised interest point detection and description", In CVPR Workshop on Deep Learning for Visual SLAM, arXiv:1712.07629v4 [cs.CV] Apr. 19, 2018, (13 pages).
Dusmanu, Mihai et al., "D2-net: A trainable CNN for joint detection and description of local features", CVPR, arXiv:1905.03561v1 [cs.CV] May 9, 2019, (16 pages).
Ebel, Patrick et al., "Beyond cartesian representations for local descriptors", ICCV, arXiv:1908.05547v1 [cs.CV] Aug. 15, 2019, (11 pages).
Fischler, Martin A et al., "Random sample consensus: a paradigm for model fitting with applications to image analysis and automated cartography", Communications of the ACM, 24(6): 1981, pp. 381-395.
Gilmer, Justin et al., "Neural message passing for quantum chemistry", In ICML, arXiv:1704.01212v2 [cs.LG] Jun. 12, 2017, (14 pages).
Giuseppe, Donato et al., "Stereoscopic helmet mounted system for real time 3D environment reconstruction and indoor ego-motion estimation", Proc. SPIE 6955, Head- and Helmet-Mounted Displays XIII: Design and Applications, SPIE Defense and Security Symposium, 2008, Orlando, Florida, United States, Apr. 18, 2008, 69550P.
Goodfellow, , "Titanium Dioxide—Titania (TiO2)", AZO Materials: Publication [online], Jan. 11, 2002 [retrieved Feb. 19, 2020], Retrieved from the Internet: <URL: https://www.azom.com/article.aspx?Article1D=1179>, (9 pages).
Hartley, Richard et al., "Multiple View Geometry in Computer Vision", Cambridge University Press, 2003, pp. 1-673.
Jacob, Robert J. , "Eye Tracking in Advanced Interface Design", Human-Computer Interaction Lab, Naval Research Laboratory, Washington, D.C., date unknown. 2003, pp. 1-50.
Lee, et al., "Self-Attention Graph Pooling", Cornell University Library/Computer Science/ Machine Learning, Apr. 17, 2019 [retrieved on Jan. 8, 2021 from the Internet< URL: https://arxiv.org/abs/1904.08082 >, entire document.
Lee, Juho et al., "Set transformer: A frame-work for attention-based permutation-invariant neural networks", ICML, arXiv:1810.00825v3 [cs.LG] May 26, 2019, (17 pages).
Leordeanu, Marius et al., "A spectral technique for correspondence problems using pairwise constraints", Proceedings of (ICCV) International Conference on Computer Vision, vol. 2, pp. 1482-1489, Oct. 2005, (8 pages).
Levola, T. , "Diffractive Optics for Virtual Reality Displays", Journal of the SID Eurodisplay 14/05, 2005, XP008093627, chapters 2-3, Figures 2 and 10, pp. 467-475.
Levola, Tapani , "Invited Paper: Novel Diffractive Optical Components for Near to Eye Displays—Nokia Research Center", SID 2006 DIGEST, 2006 SID International Symposium, Society for Information Display, vol. XXXVII, May 24, 2005, chapters 1-3, figures 1 and 3, pp. 64-67.
Li, Yujia et al., "Graph matching networks for learning the similarity of graph structured objects", ICML, arXiv:1904.12787v2 [cs.LG] May 12, 2019, (18 pages).
Li, Zhengqi et al., "Megadepth: Learning single-view depth prediction from internet photos", In CVPR, fromarXiv: 1804.00607v4 [cs.CV] Nov. 28, 2018, (10 pages).
Libovicky, et al., "Input Combination Strategies for Multi-Source Transformer Decoder", Proceedings of the Third Conference on Machine Translation (WMT). vol. 1: Research Papers, Belgium,

(56) References Cited

OTHER PUBLICATIONS

Brussels, Oct. 31-Nov. 1, 2018; retrieved on Jan. 8, 2021 (Jan. 8, 2021) from < URL: https://doi.org/10.18653/v1/W18-64026 >, entire document, pp. 253-260.

Loiola, Eliane M. et al., "A survey for the quadratic assignment problem", European journal of operational research, 176(2): 2007, pp. 657-690.

Lowe, David G., "Distinctive image features from scale-invariant keypoints", International Journal of Computer Vision, 60(2): 91-110, 2004, (28 pages).

Luo, Zixin et al., "ContextDesc: Local descriptor augmentation with cross-modality context", CVPR, arXiv:1904.04084v1 [cs.CV] Apr. 8, 2019, (14 pages).

Memon, F. et al., "Synthesis, Characterization and Optical Constants of Silicon Oxycarbide", EPJ Web of Conferences; Publication [online]. Mar. 23, 2017 [retrieved Feb. 19, 2020).<URL: https://www.epj-conferences.org/articles/epjconf/pdf/2017/08/epjconf_nanop2017_00002.pdf> DOI: 10.1051/epjconf/201713900002, (8 pages).

Molchanov, Pavlo et al., "Short-range FMCW monopulse radar for hand-gesture sensing", 2015 IEEE Radar Conference (RadarCon) (2015), pp. 1491-1496.

Munkres, James, "Algorithms for the assignment and transportation problems", Journal of the Society for Industrial and Applied Mathematics, 5(1): 1957, pp. 32-38.

Ono, Yuki et al., "LF-Net: Learning local features from images", 32nd Conference on Neural Information Processing Systems (NIPS 2018), arXiv:1805.09662v2 [cs.CV] Nov. 22, 2018, (13 pages).

Paszke, Adam et al., "Automatic differentiation in Pytorch", 31st Conference on Neural Information Processing Systems (NIPS 2017), Long Beach, CA, USA, (4 pages).

Peyré, Gabriel et al., "Computational Optimal Transport", Foundations and Trends in Machine Learning, 11(5-6):355-607, 2019; arXiv:1803.00567v4 [stat.ML] Mar. 18, 2020, (209 pages).

Qi, Charles R. et al., "Pointnet++: Deep hierarchical feature learning on point sets in a metric space.", 31st Conference on Neural Information Processing Systems (NIPS 2017), Long Beach, CA, USA., (10 pages).

Qi, Charles R et al., "Pointnet: Deep Learning on Point Sets for 3D Classification and Segmentation", CVPR, arXiv:1612.00593v2 [cs.CV] Apr. 2, 201, (19 pages).

Radenović, Filip et al., "Revisiting Oxford and Paris: Large-Scale Image Retrieval Benchmarking", CVPR, arXiv:1803.11285v1 [cs.CV] Mar. 29, 2018, (10 pages).

Raguram, Rahul et al., "A comparative analysis of ransac techniques leading to adaptive real-time random sample consensus", Computer Vision—ECCV 2008, 10th European Conference on Computer Vision, Marseille, France, Oct. 12-18, 2008, Proceedings, Part I, (15 pages).

Ranftl, René et al., "Deep fundamental matrix estimation", European Conference on Computer Vision (ECCV), 2018, (17 pages).

Revaud, Jerome et al., "R2D2: Repeatable and Reliable Detector and Descriptor", In NeurIPS, arXiv:1906.06195v2 [cs.CV] Jun. 17, 2019, (12 pages).

Rocco, Ignacio et al., "Neighbourhood Consensus Networks", 32nd Conference on Neural Information Processing Systems (NeurIPS 2018), Montréal, Canada, arXiv:1810.10510v2 [cs.CV] Nov. 29, 2018, (20 pages).

Rublee, Ethan et al., "ORB: An efficient alternative to SIFT or SURF", Proceedings of the IEEE International Conference on Computer Vision. 2564-2571.2011; 10.1109/ICCV.2011.612654, (9 pages).

Sarlin, et al., "SuperGlue: Learning Feature Matching with Graph Neural Networks", Cornell University Library/Computer Science/Computer Vision and Pattern Recognition, Nov. 26, 2019 [retrieved on Jan. 8, 2021 from the Internet< URL: https://arxiv.org/abs/1911.11763 >, entire document.

Sattler, Torsten et al., "SCRAMSAC: Improving RANSAC's efficiency with a spatial consistency filter", ICCV, 2009: 2090-2097., (8 pages).

Schonberger, Johannes L. et al., "Pixelwise view selection for un-structured multi-view stereo", Computer Vision—ECCV 2016: 14th European Conference, Amsterdam, The Netherlands, Oct. 11-14, 2016, Proceedings, Part III, pp. 501-518, 2016.

Schonberger, Johannes L. et al., "Structure-from-motion revisited", Proceedings of the IEEE Conference on Computer Vision and Pattern Recognition (CVPR), 2016, pp. 4104-4113, (11 pages).

Sheng, Liu et al., "Time-multiplexed dual-focal plane head-mounted display with a liquid lens", Optics Letters, Optical Society of Amer i ca, US, vol. 34, No. 11, Jun. 1, 2009 (Jun. 1, 2009), XP001524475, ISSN: 0146-9592, pp. 1642-1644.

Sinkhorn, Richard et al., "Concerning nonnegative matrices and doubly stochastic matrices.", Pacific Journal of Mathematics, 1967, pp. 343-348.

Spencer, T. et al., "Decomposition of poly(propylene carbonate) with UV sensitive iodonium 11 salts", Polymer Degradation and Stability (online], Dec. 24, 2010 (retrieved Feb. 19, 2020]., <URL: http:/fkohl.chbe.gatech.edu/sites/default/files/linked_files/publications/2011Decomposition%20of%20poly(propylene%20carbonate)%20with%20UV%20sensitive%20iodonium%20salts,pdf>; DOI: 10,1016/j.polymdegradstab.2010, 12.003, (17 pages).

Tanriverdi, Vildan et al., "Interacting With Eye Movements in Virtual Environments", Department of Electrical Engineering and Computer Science, Tufts University; Proceedings of the SIGCHI conference on Human Factors in Computing Systems, Apr. 2000, pp. 1-8.

Thomee, Bart et al., "YFCC100m: The new data in multimedia research", Communications of the ACM, 59(2):64-73, 2016; arXiv:1503.01817v2 [cs.MM] Apr. 25, 2016, (8 pages).

Torresani, Lorenzo et al., "Feature correspondence via graph matching: Models and global optimization", Computer Vision—ECCV 2008, 10th European Conference on Computer Vision, Marseille, France, Oct. 12-18, 2008, Proceedings, Part II, (15 pages).

Tuytelaars, Tinne et al., "Wide baseline stereo matching based on local, affinely invariant regions", BMVC, 2000, pp. 1-14.

Ulyanov, Dmitry et al., "Instance normalization: The missing ingredient for fast stylization", arXiv:1607.08022v3 [cs.CV] Nov. 6, 2017, (6 pages).

Vaswani, Ashish et al., "Attention is all you need", 31st Conference on Neural Information Processing Systems (NIPS 2017), Long Beach, CA, USA; arXiv:1706.03762v5 [cs.CL] Dec. 6, 2017, (15 pages).

Veličković, Petar et al., "Graph attention networks", ICLR, arXiv:1710.10903v3 [stat.ML] Feb. 4, 2018, (12 pages).

Villani, Cédric, "Optimal transport: old and new", vol. 338. Springer Science & Business Media, Jun. 2008, pp. 1-998.

Wang, Xiaolong et al., "Non-local neural networks", CVPR, arXiv:1711.07971v3 [cs.CV] Apr. 13, 2018, (10 pages).

Wang, Yue et al., "Deep Closest Point: Learning representations for point cloud registration", ICCV, arXiv:1905.03304v1 [cs.CV] May 8, 2019, (10 pages).

Wang, Yue et al., "Dynamic Graph CNN for learning on point clouds", ACM Transactions on Graphics, arXiv:1801.07829v2 [cs.CV] Jun. 11, 2019, (13 pages).

Weissel, et al., "Process cruise control: event-driven clock scaling for dynamic power management", Proceedings of the 2002 international conference on Compilers, architecture, and synthesis for embedded systems. Oct. 11, 2002 (Oct. 11, 2002) Retrieved on May 16, 2020 (May 16, 2020) from <URL: https://dl.acm.org/doi/pdf/10.1145/581630.581668>, p. 238-246.

Yi, Kwang M. et al., "Learning to find good correspondences", CVPR, arXiv:1711.05971v2 [cs.CV] May 21, 2018, (13 pages).

Yi, Kwang Moo et al., "Lift: Learned invariant feature transform", ECCV, arXiv:1603.09114v2 [cs.CV] Jul. 29, 2016, (16 pages).

Zaheer, Manzil et al., "Deep Sets", 31st Conference on Neural Information Processing Systems (NIPS 2017), Long Beach, CA, USA; arXiv:1703.06114v3 [cs.LG] Apr. 14, 2018, (29 pages).

Zhang, Jiahui et al., "Learning two-view correspondences and geometry using order-aware network", ICCV; aarXiv:1908.04964v1 [cs.CV] Aug. 14, 2019, (11 pages).

Zhang, Li et al., "Dual graph convolutional net-work for semantic segmentation", BMVC, 2019; arXiv:1909.06121v3 [cs.CV] Aug. 26, 2020, (18 pages).

(56) References Cited

OTHER PUBLICATIONS

"Communication Pursuant to Article 94(3) EPC dated Apr. 25, 2022", European Patent Application No. 18885707.2, (5 pages).
"Communication Pursuant to Article 94(3) EPC dated May 30, 2022", European Patent Application No. 19768418.6, (6 pages).
"Communication Pursuant to Rule 164(1) EPC dated Feb. 23, 2022", European Patent Application No. 20753144.3, (11 pages).
"Extended European Search Report dated Aug. 24, 2022", European Patent Application No. 20846338.0, (13 pages).
"Extended European Search Report dated Aug. 8, 2022", European Patent Application No. 19898874.3, (8 pages).
"Extended European Search Report dated Sep. 8, 2022", European Patent Application No. 20798769.4, (13 pages).
"Extended European Search Report dated May 16, 2022", European Patent Application No. 19871001.4, (9 pages).
"Extended European Search Report dated May 30, 2022", European Patent Application No. 20753144.3, (10 pages).
"Final Office Action dated Jul. 13, 2022", U.S. Appl. No. 17/262,991, (18 pages).
"First Examination Report dated Jul. 27, 2022", Chinese Patent Application No. 201980036675.2, (5 pages).
"First Examination Report dated Jul. 28, 2022", Indian Patent Application No. 202047024232, (6 pages).
"First Examination Report dated May 13, 2022", Indian Patent Application No. 202047026359, (8 pages).
"FS_XR5G: Permanent document, v0.4.0", Qualcomm Incorporated, 3GPP TSG-SA 4 Meeting 103 retrieved from the Internet: URL:http://www.3gpp.org/ftp/Meetings%5F3GP P%5FSYNC/SA4/Docs/S4%2DI90526% 2Ezip [retrieved on Apr. 12, 2019], Apr. 12, 2019, (98 pages).
"Non Final Office Action dated May 10, 2022", U.S. Appl. No. 17/140,921, (25 pages).
"Non Final Office Action dated May 17, 2022", U.S. Appl. No. 16/748,193, (11 pages).
"Non Final Office Action dated Sep. 19, 2022", U.S. Appl. No. 17/263,001, (14 pages).
"Second Office Action dated Jul. 13, 2022 with English Translation", Chinese Patent Application No. 201880079474.6, (10 pages).
"Second Office Action dated Jun. 20, 2022 with English Translation", Chinese Patent Application No. 201880089255.6, (14 pages).
Anonymous , "Koi Pond: Top iPhone App Store Paid App", https://web.archive.org/web/20080904061233/https://www.iphoneincanada.ca/reviews /koi-pond-top-iphone-app-store-paid-app/- [retrieved on Aug. 9, 2022], (2 pages).
Chittineni, C., et al., "Single filters for combined image geometric manipulation and enhancement", Proceedings of SPIE vol. 1903, Image and Video Processing, Apr. 8, 1993, San Jose, CA. (Year: 1993), pp. 111-121.
"Decision of Rejection dated Jan. 5, 2023 with English translation", Chinese Patent Application No. 201880079474.6, (10 pages).
"Extended European Search Report dated Dec. 14, 2022", European Patent Application No. 20886547.7, (8 pages).
"Extended European Search Report dated Nov. 3, 2022", European Patent Application No. 20770244.0, (23 pages).
"Final Office Action dated Mar. 10, 2023", U.S. Appl. No. 17/357,795, (15 pages).
"First Office Action dated Dec. 22, 2022 with English translation", Chinese Patent Application No. 201980061450.2, (11 pages).
"First Office Action dated Jan. 24, 2023 with English translation", Japanese Patent Application No. 2020-549034, (7 pages).
"First Office Action dated Jan. 30, 2023 with English translation", Chinese Patent Application No. 201980082951.9, (5 pages).
"First Office Action dated Sep. 16, 2022 with English translation", Chinese Patent Application No. 201980063642.7, (7 pages).
"Non Final Office Action dated Dec. 7, 2022", U.S. Appl. No. 17/357,795, (63 pages).
"Non Final Office Action dated Feb. 3, 2023", U.S. Appl. No. 17/429,100, (16 pages).
"Non Final Office Action dated Feb. 3, 2023", U.S. Appl. No. 17/497,965, (32 pages).
"Non Final Office Action dated Jan. 24, 2023", U.S. Appl. No. 17/497,940, (10 pages).
"Non Final Office Action dated Mar. 1, 2023", U.S. Appl. No. 18/046,739, (34 pages).
"Notice of Reason for Rejection dated Oct. 28, 2022 with English translation", Japanese Patent Application No. 2020-531452, (3 pages).
"Office Action dated Nov. 24, 2022 with English Translation", Japanese Patent Application No. 2020-533730, (11 pages).
"Extended European Search Report dated Apr. 5, 2023", European Patent Application No. 20888716.6, (11 pages).
"First Office Action dated Apr. 21, 2023 with English translation", Japanese Patent Application No. 2021-509779, (26 pages).
"First Office Action dated Apr. 13, 2023 with English Translation", Japanese Patent Application No. 2020-567766, (7 pages).
"First Office Action dated Mar. 27, 2023 with English translation", Japanese Patent Application No. 2020-566617, (6 pages).
"Non Final Office Action dated Apr. 13, 2023", U.S. Appl. No. 17/098,043, (7 pages).
"Non Final Office Action dated May 11, 2023", U.S. Appl. No. 17/822,279, (24 pages).
"Office Action dated Apr. 13, 2023 with English translation", Japanese Patent Application No. 2020-533730, (13 pages).
"Office Action dated Mar. 30, 2023 with English translation", Japanese Patent Application No. 2020-566620, (10 pages).
"Second Office Action dated May 2, 2023 with English Translation", Japanese Patent Application No. 2020-549034, (6 pages).
Li, Yujia , et al., "Graph Matching Networks for Learning the Similarity of Graph Structured Objects", arxiv.org, Cornell University Library, 201 Olin Library Cornell University Ithaca, NY 14853, XP081268608, Apr. 29, 2019.
Luo, Zixin , et al., "ContextDesc: Local Descriptor Augmentation With Cross-Modality Context", 2019 IEEE/CVF Conference On Computer Vision and Pattern Recognition (CVPR), IEEE, XP033686823, DOI: 10.1109/CVPR.2019.00263 [retrieved on Jan. 8, 2020], Jun. 15, 2019, pp. 2522-2531.
Zhang, Zen , et al., "Deep Graphical Feature Learning for the Feature Matching Problem", 2019 IEEE/CVF International Conference On Computer Vision (ICCV), IEEE, XP033723985, DOI: 10.1109/ICCV.2019.00519 [retrieved on Feb. 24, 2020], Oct. 27, 2019, pp. 5086-5095.
"First Office Action dated Jun. 13, 2023 with English translation", Japanese Patent Application No. 2020-567853, (7 pages).
"Office Action dated Jun. 8, 2023 with English translation", Japanese Patent Application No. 2021-503762, (6 pages).
"First Office Action dated May 30, 2023 with English translation", Japanese Patent Application No. 2021-519873, (8 pages).
"First Office Action dated May 26, 2023 with English translation", Japanese Patent Application No. 2021-500607, (6 pages).
"Non Final Office Action dated Jun. 14, 2023", U.S. Appl. No. 17/516,483, (10 pages).

\* cited by examiner

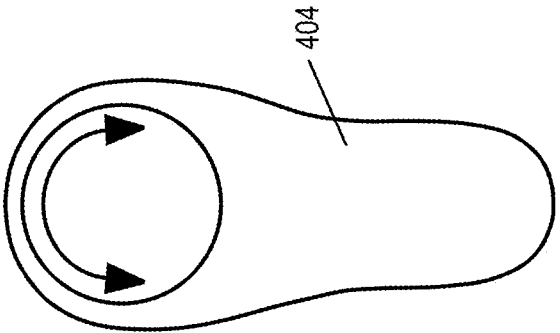

Touch the controller touchpad and rotate clockwise or counterclockwise to rotate the selected implant.

Half clockwise: +0.5 deg
Half counterclockwise: -0.5 deg
Full clockwise: 1 deg
Full counterclockwise: -1 deg

FIG. 58C

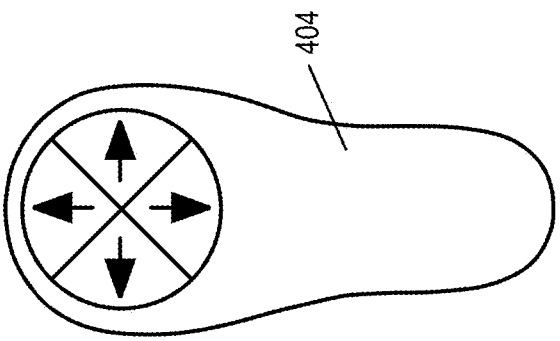

Swipe controller touchpad's top, down, left or right sections to translate the selected implant by 0.5mm.

FIG. 58B

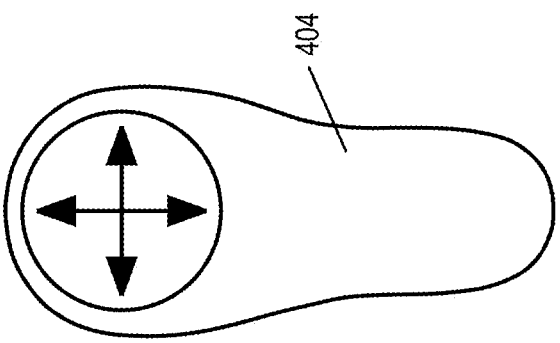

Swipe the controller touch up, down, left or right top translate the selected implant by 1mm.

FIG. 58A

VIEWING SYSTEM FOR USE IN A SURGICAL ENVIRONMENT

CROSS-REFERENCE TO RELATED APPLICATIONS

This application claims priority from U.S. Provisional Patent Application No. 62/936,383, filed on Nov. 15, 2019, all of which is incorporated herein by reference in its entirety.

BACKGROUND OF THE INVENTION

1). Field of the Invention

This invention relates generally to a viewing system and more specifically to a viewing system that functions within a surgical environment.

2). Discussion of Related Art

To execute a surgery within surgical environments such as a hospital or a clinic requires disparate contributions from various people, including personnel that are responsible for setting a room up for surgery, radiology personnel responsible for recording radiology data of body parts of a patient, surgeons and other experts who collaborate to plan a surgery using visualizations of the radiology data, surgeons and other surgical staff who execute surgeries, and personnel responsible for airing the room up and replenishing disposable items.

The visualizations of the radiology data are static visualizations based on radiology data that was previously collected. Solutions do not typically exist to interact with the visualizations to plan the surgery. After the planning phase is completed, the radiology data is typically not used to execute the surgery. Robots are frequently used to execute surgeries. These robots are digitally connected over long distances to operators such as remote surgeons who can steer these robots to execute surgeries, including make a cut into a human body and placing an implant into the human body. These remote operators rely on visuals of both the robot and the human body to steer the robot.

Without a digital twin of the real environment, it is very difficult to attain any repeatability or to attain a high degree of accuracy in setting a room up, anatomy registration, surgical planning, and surgical execution.

SUMMARY OF THE INVENTION

The invention provides a viewing system including a real object detection device positioned to detect locations of real objects in a real environment, at least one processor, a computer-readable medium connected to the processor, a data store on the computer-readable medium; and a set of instructions stored on the computer-readable medium and executable by the processor. The set of instructions may include a map generator connected to the real object detection device to receive data of the real environment including the real objects and executable to create a map that forms a digital representation of the real environment including the real objects, a map storing routine executable to store the map on the data store and a guiding module connected to the data store to retrieve the map and executable to guide at least one of a virtual object and a real object based on the digital representation.

The invention also provides a viewing method including detecting, with a real object detection device, locations of real objects in a real environment, executing, with a processor, a map generator connected to the real object detection device to receive data of the real environment including the real objects and create a map that forms a digital representation of the real environment including the real objects, executing, with the processor, a map storing routine to store the map on the data store, and executing, with the processor, a guiding module connected to the data store to retrieve the map and guide at least one of a virtual object and a real object based on the digital representation.

The invention further provides a viewing system including a real object detection device positioned to detect locations of real objects in a real environment, at least one processor, a computer-readable medium connected to the processor, a data store on the computer-readable medium and a set of instructions stored on the computer-readable medium and executable by the processor. The set of instructions may include a map generator connected to the real object detection device to receive data of the real environment including the real objects and executable to create a map that forms a digital representation of the real environment including the real objects, a map storing routine executable to store the map on the data store, and a plurality of guiding modules connected to the data store to retrieve the map and executable to guide at least one of a virtual object and a real object based on the digital representation, wherein the guiding modules include at least two of: a. a room setup module that is executable by the processor to set a room up based on the digital representation and may include storing a desired room layout, and providing an output that superimposes the desired room layout digitally relative to the real environment; b. an anatomy registration module that is executable by the processor to execute anatomy registration based on the digital representation that may include storing a location of a body part of a patient, wherein the location of the body part is based on a location of a real object by the real object detection device; c. a surgical planning module that is executable by the processor to plan a surgery based on the digital representation, that may include storing a digital representation of a body part of a patient, displaying the digital representation of the body part of the patient together with the virtual object to a user, receiving input from the user to guide the virtual object relative to the digital representation of the body part and moving, in a view of the user, the virtual object relative to the digital representation of the body part in response to the input from the user; and d. a surgical execution module that is executable by the processor to assist in executing a surgery based on the digital representation, that may include storing a digital representation of a body part of a patient, receiving input from the user to guide the virtual object relative to the digital representation of the body part, and in response to the input from the user, moving, in a view of the user, the virtual object relative to the digital representation of the body part, and moving, in the real environment, a respective one of the real objects relative to the body part of the patient.

The invention also provides a viewing method including detecting, with a real object detection device, locations of real objects in a real environment, executing, with a processor, a map generator connected to the real object detection device to receive data of the real environment including the real objects and create a map that forms a digital representation of the real environment including the real objects, executing, with the processor, a map storing routine to store the map on the data store, and executing, with the processor, a plurality of guiding module connected to the data store to retrieve the map and guide at least one of a virtual object and a real object based on the digital representation, wherein the guiding modules include at least two of: a. a room setup module that is executable by the processor to set a room up based on the digital representation that may include storing a desired room layout, and providing an output that superimposes the desired room layout digitally relative to the real environment; b. wherein the guiding module is an anatomy registration module that is executable by the processor to execute anatomy registration based on the digital representation that may include storing a location of a body part of a patient, wherein the location of the body part is based on a location of a real object by the real object detection device; c. a surgical planning module that is executable by the processor to plan a surgery based on the digital representation, that may include storing a digital representation of a body part of a patient, displaying the digital representation of the body part of the patient together with the virtual object to a user, receiving input from the user to guide the virtual object relative to the digital representation of the body part, and moving, in a view of the user, the virtual object relative to the digital representation of the body part in response to the input from the user; and d. a surgical execution module that is executable by the processor to assist in executing a surgery based on the digital representation that may include storing a digital representation of a body part of a patient, receiving input from the user to guide the virtual object relative to the digital representation of the body part, and in response to the input from the user, moving, in a view of the user, the virtual object relative to the digital representation of the body part, and moving, in the real environment, a respective one of the real objects relative to the body part of the patient.

Forward and return waves are used in the field of radiology for purposes of imaging patients. For example, x-ray machines and computer tomography (CT) machines use x-ray waves, ultrasound machines use ultrasound waves, and magnetic resonance imaging (MRI) machines use alternating magnetic fields or waves and radio waves in a forward and return fashion to detect an internal structure of a patient.

In the context of radiology data, the invention further provides a viewing system including a real object detection device positioned to detect locations of real objects in a real environment, at least one processor, a computer-readable medium connected to the processor, a data store on the computer-readable medium and a set of instructions stored on the computer-readable medium and executable by the processor. The set of instructions may include a map generator connected to the real object detection device to receive data of the real environment including the real objects and executable to create a map that forms a digital representation of the real environment including the real objects, a map storing routine executable to store the map on the data store, a head-mountable frame, the light wave guide being secured to the head-mountable frame, a raw data reception unit that receives raw data of a return wave, an image generation unit connected to the data store to process the raw data of the return wave to create image data representing an image and store the image data in the data store, an image data reception unit that receives the image data from the data store, at least one projector connected to the image data reception unit to receive the image data, the projector generating light in a pattern representative of the image data and based on the map, and at least one light wave guide connected to the projector and secured to the head-mountable frame to guide the light to a retina of an eye of a user so that the user sees a rendering of the image data.

The invention also provides a viewing method including detecting, with a real object detection device, locations of real objects in a real environment, executing, with a processor, a map generator connected to the real object detection device to receive data of the real environment including the real objects and create a map that forms a digital representation of the real environment including the real objects, executing, with the processor, a map storing routine to store the map on the data store, mounting a head-mountable frame to a head of a viewer, storing the raw data of a return wave in a data store, processing the raw data of the return wave to create image data, storing the image data in the data store, receiving the image data from the data store, generating light in a pattern representative of the image data and based on the map, and guiding, with a light wave guide secured to the head-mountable frame, the light to a retina of an eye of a viewer so that the viewer sees a rendering of the image data.

The invention further provides a viewing system including a real object detection device positioned to detect locations of real objects in a real environment, at least one processor, a computer-readable medium connected to the processor, a data store on the computer-readable medium and a set of instructions stored on the computer-readable medium and executable by the processor. The set of instructions may include a map generator connected to the real object detection device to receive data of the real environment including the real objects and executable to create a map that forms a digital representation of the real environment including the real objects, a map storing routine to store a first map having a plurality of anchors, each anchor of the first map having a set of coordinates, an anchor identification system connected to the real object detection device to detect, based on the locations of the real objects, anchors of a second map, each anchor of the second map having a set of coordinates, and a localization module connected to the first map and the second map and executable to localize the second map to the first map by matching a first anchor of the second map to a first anchor of the first map and matching a second anchor of the second map to a second anchor of the first map.

The invention also provides a viewing method including detecting, with a real object detection device, locations of real objects in a real environment, executing, with a processor, a map generator connected to the real object detection device to receive data of the real environment including the real objects and create a map that forms a digital representation of the real environment including the real objects, storing a first map having a plurality of anchors, each anchor of the first map having a set of coordinates, detecting, based on the locations of the real objects, anchors of a second map, each anchor of the second map having a set of coordinates, and localizing the second map to the first map by matching a first anchor of the second map to a first anchor of the first map and matching a second anchor of the second map to a second anchor of the first map.

BRIEF DESCRIPTION OF THE DRAWINGS

The invention is further described by way of example with reference to the accompanying drawings, wherein:

FIGS. 58a, 58b and 58c illustrate how a finger input surface of a handheld controller component is used by the user to manipulate the robot;

DETAILED DESCRIPTION OF THE INVENTION

Figure 1:
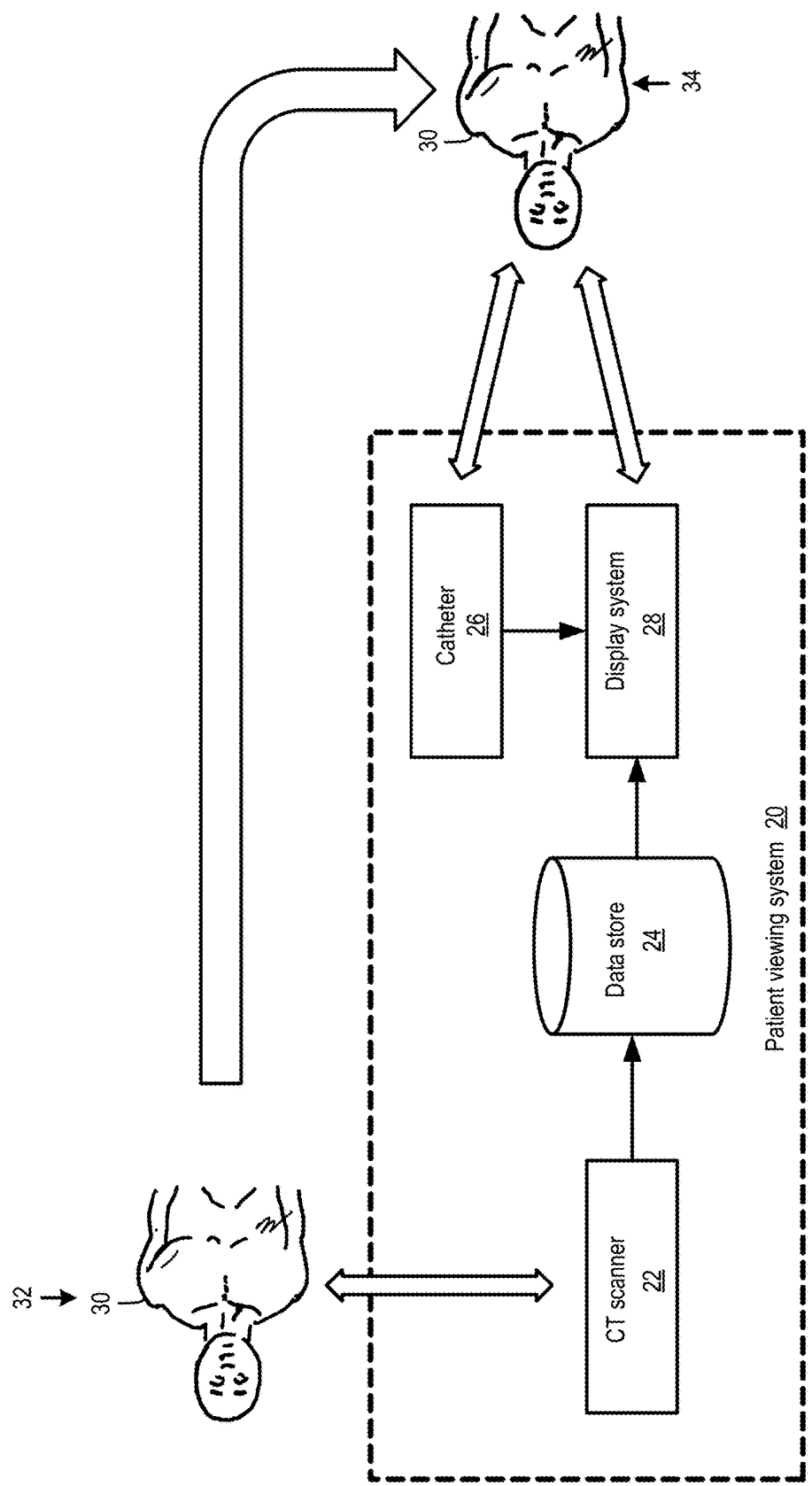
FIG. 1 is a block diagram of a patient viewing system according to an embodiment of the invention.

FIG. 1 of the accompanying drawings illustrates a viewing system 20, according to an embodiment of the invention, that includes a CT scanner 22, a data store 24, a catheter 26, and a display system 28.

The data store 24 is connected to the CT scanner 22. Raw data from the CT scanner 22 may be stored in the data store 24. The data store 24 also stores image data that is based on the raw data.

The display system 28 is connected to the data store 24 to be able to retrieve the image data from the data store 24. The catheter 26 is connected to the display system 28 so that the display system 28 can retrieve measurement and video data from the catheter 26 for further processing or for display to a viewer.

In use, a patient is located at a station 32 at the CT scanner 22. A body 30 of the patient is scanned with the CT scanner 22 to obtain raw data that the CT scanner 22 stores in the data store 24. The raw data is then processed to obtain 3D image data.

The patient is transferred from the station 32 at the CT scanner 22 to a station 34 at the display system 28. A viewer uses the display system 28 to view the body 30 of the patient. The display system 28 also retrieves the image data from the data store 24. The viewer uses the display system 28 to view an image in the form of a 3D rendering of the body 30 of the patient. The viewer inserts the catheter 26 into the body 30. The display system 28 retrieves data from a tip of the catheter 26 for further processing or for display to the viewer.

Figure 2:
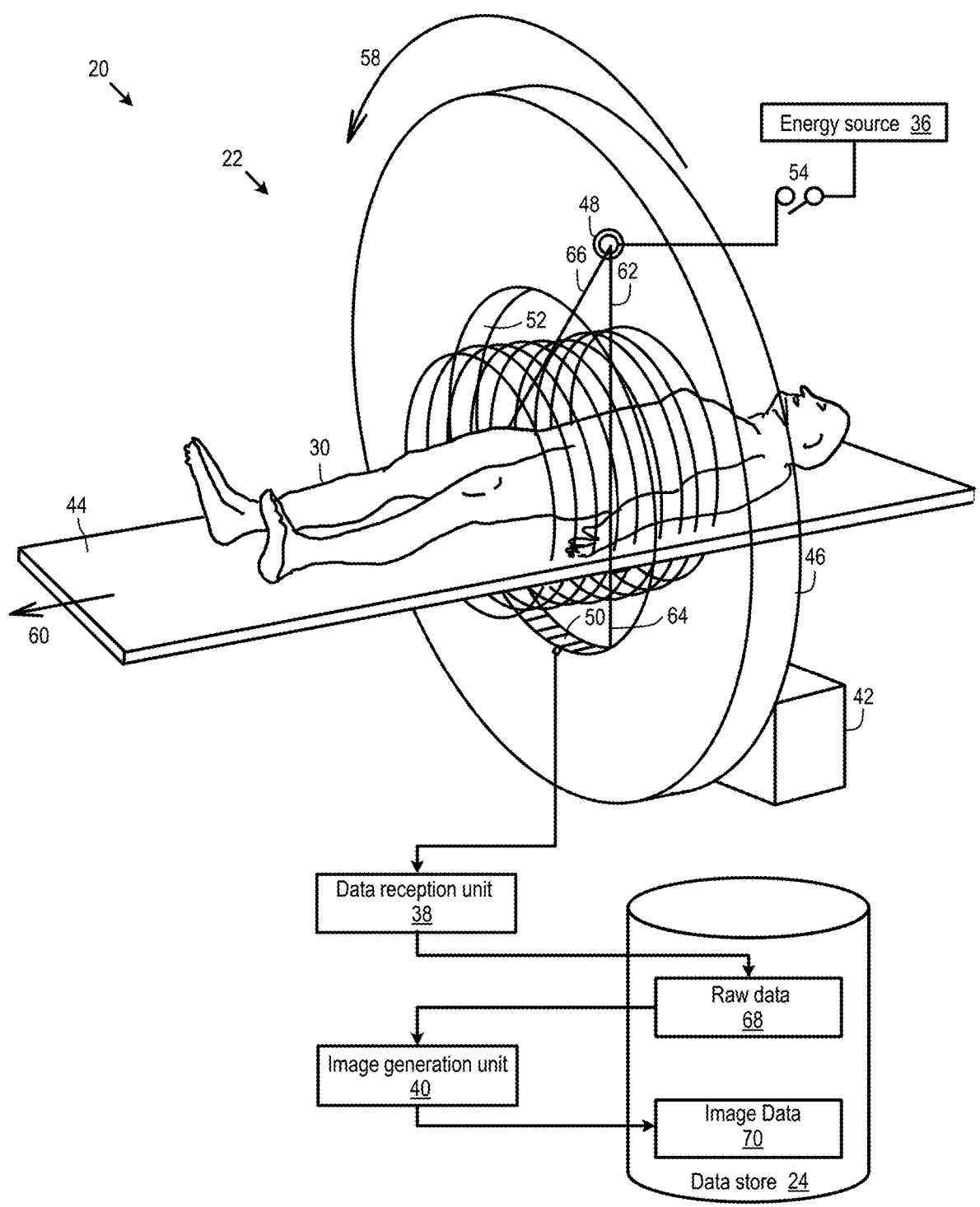
FIG. 2 is a partial perspective view and partial block diagram of a CT scanner, a data reception unit, an image generation unit, and a data store forming part of the patient viewing system.

FIG. 2 illustrates components of the viewing system 20, including the CT scanner 22, the data store 24, an energy source 36, a data reception unit 38, and an image generation unit 40.

The CT scanner 22 includes a base 42, a platform 44, a rotor 46, an x-ray transmitter 48, and a plurality of x-ray detectors 50.

The platform 44 is secured to the base 42 through a mechanism (not shown) that permits translational movement of the platform 44 relative to the base 42. An actuator such as a stepper motor (not shown) is operable to cause translational movement of the platform 44 relative to the base 42.

The rotor 46 has an opening 52. The x-ray transmitter 48 is secured to the rotor 46 on one side of the opening 52 and the x-ray detectors 50 are secured to the rotor 46 on an opposing side of the opening 52. The rotor 46 is mounted to the base 42 around the platform 44. The platform 44 moves relative to the opening 52 during its translational movement.

A motor (not shown) is connected between the base 42 and the rotor 46 and is operable to rotate the rotor 46 around the platform 44.

The energy source 36 may be connected to the x-ray transmitter 48 through a switch 54. The x-ray detectors 50 are connected to the data reception unit 38. The data reception unit 38 may be a software unit that resides on a computer-readable medium of a computer. The data store 24 resides on the computer-readable medium. The computer-readable medium may be a single computer-readable medium or may be separated within one personal computer or a number of personal computers that are connected to one another on a network. The data reception unit 38 is connected to the data store 24, either directly or over a network.

The image generation unit 40 may be a computer program that resides on the computer-readable medium. The image generation unit 40 is connected to the data store 24, either directly or over a network.

In use, an operator of the CT scanner 22 places the patient with their body 30 laying on the platform 44. The motor connected between the base 42 and the rotor 46 is then switched on so that the rotor 46 rotates in a direction 58 about the platform 44 and the body 30 of the patient. The operator also switches the motor on that moves the platform 44 in a translation direction relative to the base 42 so that the platform 44 moves in a direction 60 relative to the rotor 46. The operator then connects the switch 54 between the energy source 36 and the x-ray transmitter 48 to activate the x-ray transmitter 48. The x-ray transmitter then generates a forward x-ray wave 62.

The body 30 of the patient is positioned relative to the x-ray transmitter 48 so that the forward x-ray wave 62 penetrates the body 30 to a body part (not shown) within the body 30. For purposes of this example, the body parts that are scanned are the lungs of a patient. A lung has many bronchi through which a catheter can travel. It may also be possible for a catheter to travel though hollow passages in the heart, arteries, and veins of the blood circulation system etc. The system described herein may also find application for viewing internal body parts without the use of a catheter for vision, surgery or intervention, for example for viewing a growth within the abdomen, for analyzing the internal functioning of a knee, etc. The body part reduces the energy of the forward x-ray wave 62. Different materials within the body part reduce the energy by different amounts. One of the x-ray detectors 50 is positioned relative to the body 30 to detect a return x-ray wave 64 from the body part. The return x-ray wave 64 from the body part is being detected in response to the forward x-ray wave 62 and is essentially the forward x-ray wave 62 that has reduced power because of the reduction in the power by the body part. Further forward x-ray wave 66 is also illustrated. The further x-ray waves are generated between the forward x-ray waves 62 and 66 and are detected by respective ones of the x-ray detectors 50. In this manner, return x-ray waves are received from different parts of the body part.

The x-ray transmitter 48 and x-ray detectors 50 rotate together with the rotor 46 around the body part within the body 30 of the patient. In this manner, the body part may be scanned from different angles to create a two-dimensional "slice" of the anatomy. CT scans are capable of showing bone, organs, soft tissue. Subsequent slices are taken by moving the platform 44 in the direction 60. Each slice thus represents two-dimensional data and the slices together represent data in three-dimensions of the body part.

The data reception unit 38 receives raw data of the return x-ray wave 64 from the x-ray detectors 50. The raw data includes a time sequenced correlation between an angle of the x-ray transmitter 48 relative to the body part within the body 30 of the patient, an energy detected by each one of the x-ray detectors 50, the location of each one of the x-ray detectors 50, and a position of the platform 44. The data reception unit 38 stores the raw data as raw data 68 of the return x-ray wave detected by the x-ray detectors 50.

When enough raw data 68 of the body part is collected, the operator disconnects the switch 54 and stops the platform 44. The operator then stops the rotor 46 and removes the patient from the platform 44.

The image generation unit 40 retrieves the raw data 68 from the data store 24. The image generation unit 40 generates image data based on the raw data 68. The image data includes a three-dimensional rendering of the body part. The image generation unit 40 then stores the image data as image data 70 in the data store 24. The data store 24 may be a single data store or may be distributed between platforms, and as such, the raw data 68 and the image data 70 can be located within a single data store within a personal computer or within several data stores within several personal computers.

Figure 3:
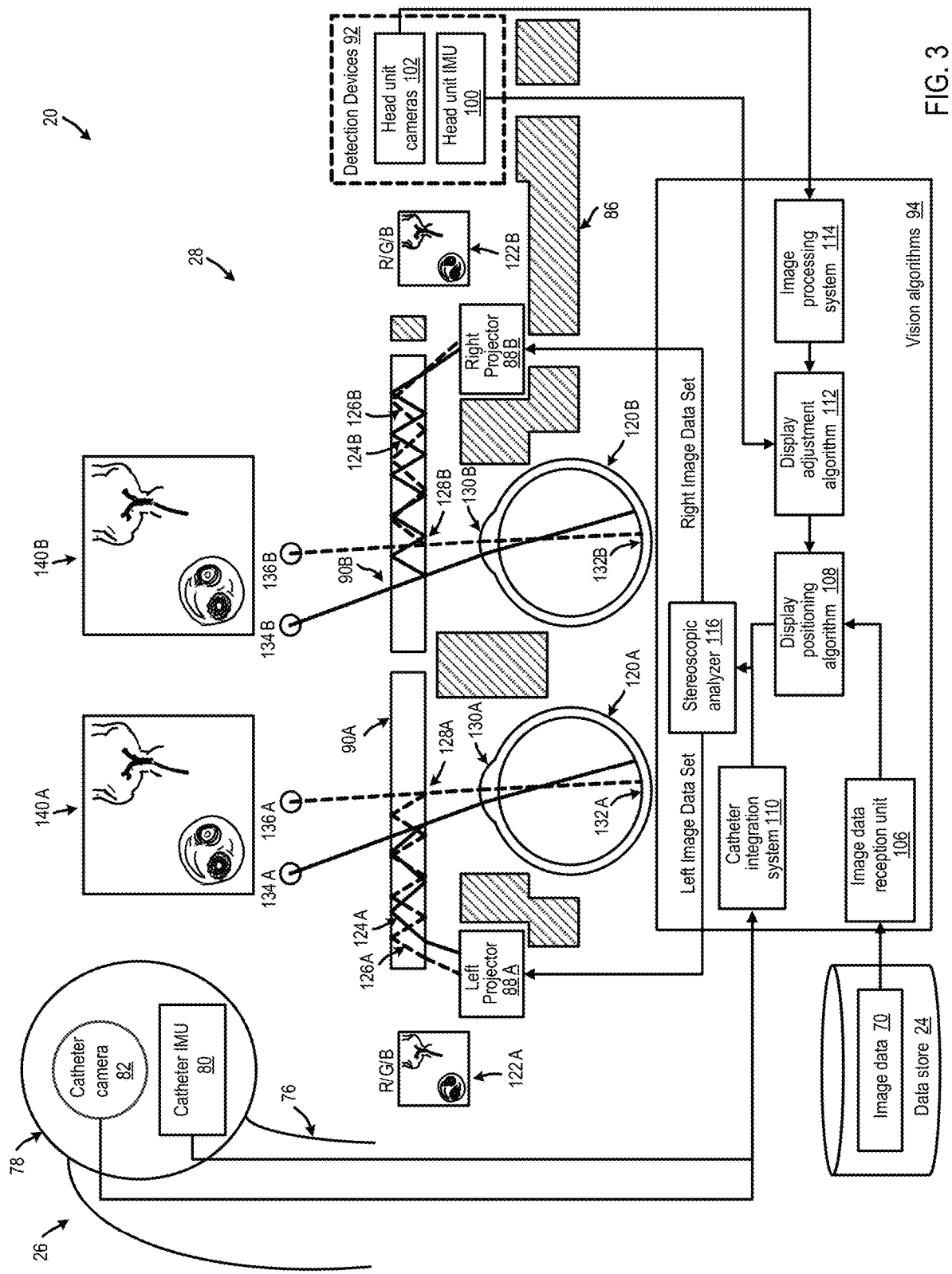
FIG. 3 is a partial perspective view and partial block diagram of a display system, a catheter and a data store forming part of the patient viewing system.

FIG. 3 illustrates components of the viewing system 20 in more detail, and shows the data store 24 (holding the image data 70), the catheter 26, and the display system 28.

The catheter 26 includes a lumen 76 and a tip 78 attached to an end of the lumen 76. The lumen is an elongate member (e.g., the cavity of a tubular part) that forms most of the length of the catheter 26. The lumen 76 includes a mechanism (not shown) that is operable to move the tip 78 in at least four orthogonal directions and all directions in between the orthogonal directions. The tip 78 is thus steerable with the mechanism in the lumen 76. The lumen has a hollow bore that is sufficiently large to hold the mechanism that is used to steer the tip together with any electrical cables and/or an optic fiber that may be required for relaying signals from the tip through the lumen 76 to the display system 28.

The catheter 26 further includes a catheter inertial measurement unit (IMU) 80 and a catheter camera 82 secured to the tip 78. The catheter IMU 80 may for example be a semiconductor chip that has a number of measurement devices formed therein. The measurement devices include one or more gyroscopes and one or more accelerometers. Measurements from the gyroscopes and accelerometers, individually or in combination, provide data that indicates movement of the tip 78. Such movement can be tracked in six degrees of freedom, for example translation in x-, y- and z-directions and rotation about x-, y-, and z-axes.

The catheter camera 82 has a lens (not shown) on the side of the tip 78 opposing the lumen 76. The catheter camera 82 is positioned to capture images in the form of live video data in an area in front of the tip 78, i.e., on a side opposing the lumen 76. There may be multiple light sources and multiple cameras on different sides of the tip of the camera, although for ease of discussion it will be assumed that there is only a single camera, for example a built-in camera and light source on a distal end of the catheter.

The display system 28 includes a head-mountable frame 86, left and right projectors 88A and 88B, left and right wave guides 90A and 90B, detection devices 92, and vision algorithms 94. The left and right projectors 88A and 88B, left and right wave guides 90A and 90B and the detection devices 92 are secured to the head-mountable frame 86. The head-mountable frame 86 is shaped to be mounted to a head of a viewer. Components of the head-mountable frame 86 may, for example, include a strap (not shown) that wraps around the back of a head of a viewer.

The left and right projectors 88A and 88B are connected to power supplies. Each projector 88A or 88B has a respective input for image data to be provided to the respective projector 88A or 88B. The respective projector 88A or 88B, when powered, generates light in a two-dimensional pattern and emanates the light therefrom. The left and right wave guides 90A and 90B are positioned to receive the light from the left and right projectors 88A and 88B, respectively. The left and right wave guides 90A and 90B are transparent wave guides.

The detection devices 92 include a head unit IMU 100 (or more than one IMU) and one or more head unit cameras 102. The head unit IMU 100 includes one or more gyroscopes and one or more accelerometers. The gyroscopes and accelerometers are typically formed in a semiconductor chip and are capable of detecting movement of the head unit IMU 100 and the head-mountable frame 86, including movement along three orthogonal axes and rotation about three orthogonal axes.

The head unit cameras 102 continually capture images from an environment around the head-mountable frame 86. The images can be compared to one another to detect movement of the head-mountable frame 86 and the head of the viewer.

The vision algorithms 94 include an image data reception unit 106, a display positioning algorithm 108, a catheter integration system 110, a display adjustment algorithm 112, an image processing system 114, and a stereoscopic analyzer 116. The image data reception unit 106 is connected to the data store 24 through a direct connection or over a network. The components of the vision algorithm 94 are linked to one another through subroutines or calls. Through such subroutines and calls, the image data reception unit 106 is linked via the display positioning algorithm 108 to the stereoscopic analyzer 116.

The catheter integration system 110 may be connected to the catheter IMU 80 and the catheter camera 82 through conductors in the lumen 76. One of ordinary skill in the art will appreciate that the vision algorithms 94 reside on a computing system and that the catheter integration system 110 receives signals from the catheter camera 82 and the catheter IMU 80 and that such signals may convert from analog or digital data to computer software data. The catheter integration system 110 may be connected through subroutines or calls to the stereoscopic analyzer 116.

The display adjustment algorithm 112 and the image processing system 114 are connected to the head unit IMU 100 and the head unit cameras 102, respectively. Such connections are through conductors and, where applicable, through inverters that convert analog or digital data to computer software data. The display adjustment algorithm 112 may be connected through subroutines and calls to the display positioning algorithm 108. The image processing system 114 may be connected though calls and subroutines to the display adjustment algorithm 112.

In use, a viewer mounts the head-mountable frame 86 to their head. The left and right wave guides 90A and 90B are then located in front of left and right eyes 120A and 120B of the viewer.

The image data reception unit 106 retrieves the image data 70 from the data store 24 and provides the image data 70 to the display positioning algorithm 108. The display positioning algorithm 108 enters the image data 70 into the stereoscopic analyzer 116. The image data 70 is three-dimensional image data of the body part as described above. The stereoscopic analyzer 116 analyzes the image data 70 to determine left and right image data sets based on the image data 70. The left and right image data sets are data sets that represent two-dimensional images that differ slightly from one another for purposes of giving the viewer a perception of a three-dimensional rendering. The image data 70 is a static data set which does not change over time.

The stereoscopic analyzer 116 enters the left and right image data sets in to the left and right projectors 88A and 88B. The left and right projectors 88A and 88B then create left and right light patterns 122A and 122B. The components of the display system 28 are shown in plan view and the left and right light patterns 122A and 122B are shown in front elevation views. Each light pattern 122A and 122B includes a plurality of pixels. For purposes of illustration, light rays 124A and 126A from two of the pixels are shown leaving the left projector 88A and entering the left wave guide 90A. The light rays 124A and 126A reflect from sides of the left wave guide 90A. It is shown that the light rays 124A and 126A propagate through internal reflection from left to right within the left wave guide 90A, although it should be understood that the light rays 124A and 126A also propagate in a direction into the paper using refractory and reflective systems. The light rays 124A and 126A exit the left light wave guide 90A through a pupil 128A and then enter the left eye 120A through a pupil 130A of the left eye. The light rays 124A and 126A then fall on a retina 132A of the left eye 120A. In this manner, the left light pattern 122A falls on the retina 132A of the left eye 120A. The viewer is given the perception that the pixels that are formed on the retina 132A are pixels 134A and 136A that the viewer perceives to be at some distance on a side of the left wave guide 90A opposing the left eye 120A.

In a similar manner, the stereoscopic analyzer 116 enters the right image data set into the right projector 88B. The right projector 88B transmits the right light pattern 122B, which is represented by pixels in the form of light rays 124B and 126B. The light rays 124B and 126B reflect within the right wave guide 90B and exit through a pupil 128B. The light rays 124B and 126B then enter through a pupil 130B of the right eye 120B and fall on a retina 132B of the right eye 120B. The pixels of the light rays 124B and 126B are perceived as pixels 134B and 136B behind the right light wave guide 90B.

The patterns that are created on the retinas 132A and 132B are individually perceived as left and right images 140A and 140B that are shown in front elevation view. The left and right images 140A and 140B differ slightly from one another due to the functioning of the stereoscopic analyzer 116. The left and right images 140A and 140B are perceived in a mind of the viewer as a three-dimensional rendering.

As mentioned, the left and right wave guides 90A and 90B are transparent. Light from a real-life object on a side of the left and right wave guides 90A and 90B opposing the eyes 120A and 120B can project through the left and right wave guides 90A and 90B and fall on the retinas 132A and 132B. In particular, light from a surface of the body 30 of the patient falls on the retinas 132A and 132B so that the viewer can see the surface of the body 30 of the patient. An augmented reality is created wherein the surface of the body 30 of the patient that the viewer sees is augmented with a three-dimensional rendering that is perceived by the viewer due to the left and right images 140A and 140B that are, in combination, perceived by the viewer.

The head unit IMU 100 detects every movement of the head of the viewer. Should the viewer, for example, move counterclockwise around the body 30 of the patient and simultaneously rotate their head counterclockwise to continue to see the body 30 of the patient, such movement will be detected by the gyroscopes and accelerometers in the head unit IMU 100. The head unit IMU 100 provides the measurement from the gyroscopes and accelerometers to the display adjustment algorithm 112. The display adjustment algorithm 112 calculates a placement value and provides the placement value to the display positioning algorithm 108. The display positioning algorithm 108 modifies the image data 70 to compensate for movement of the head of the viewer. The display positioning algorithm 108 provides the modified image data 70 to the stereoscopic analyzer 116 for display to the viewer.

The head unit cameras 102 continually capture images as the viewer moves their head. The image processing system 114 analyzes the images by identifying images of objects within the image. The image processing system 114 analyzes movement of the objects to determine a pose position of the head-mountable frame 86. The image processing system 114 provides the pose position to the display adjustment algorithm 112. The display adjustment algorithm 112 uses the pose position to further refine the placement value that the display adjustment algorithm 112 provides to the display positioning algorithm 108. The display positioning algorithm 108 thus modifies the image data 70 based on a combination of motion sensors in the head unit IMU 100 and images taken by the head unit cameras 102.

The catheter integration system 110 may detect a location of the tip 78 of the catheter 26 before the viewer inserts the tip 78 into the body 30 of the patient. The viewer subsequently inserts the tip 78 into the body 30 of the patient. The tip 78 is then not visible to the viewer. The catheter IMU 80 provides signals to the catheter integration system 110 that indicate every movement of the tip 78. The catheter integration system 110 can thus track the position of the tip 78 using the motion sensors in the catheter IMU 80. Unlike the image data 70 that is static, the position of the tip 78 changes over time. The catheter integration system 110 provides the position of the tip 78 to the stereoscopic analyzer 116. The position of the tip 78 may be dynamic in that it changes over time and moves in three-dimensions. The stereoscopic analyzer 116 positions the tip 78 within the left and right image data sets that are inserted into the left and right projectors 88A and 88B. The viewer can thus see the location in the tip 78 within the left and right images 140A and 140B. The location of the tip 78 varies slightly within the left and right images 140A and 140B so that the viewer perceives the location of the tip 78 in three-dimensions. The rendering of the location of the tip 78 as provided by the left and right images 140A and 140B changes over time as the tip 78 makes its way through the body 30 of the patient. Such movement of the location of tip 78 as a rendering changes in three-dimensions so that the viewer perceives the rendering of the tip 78 as moving in three-dimensions, i.e., left, right, up, down, forward, backward, etc.

The catheter camera 82 continues to capture video data and provides the video data to the catheter integration system 110. The catheter integration system 110 provides the video data to the stereoscopic analyzer 116. The stereoscopic analyzer 116 places the video data at a fixed location within the view of the viewer unless or until a user interaction event is detected indicating the location should change. The video data changes over time as different images are captured by the catheter camera 82.

The vision algorithms 94 are a set of instructions that are stored together with the data store 24 on a computer-readable medium. The set of instructions are executable by a processor to carry out the method described above. The computer-readable medium that stores the vision algorithms 94 may be located on a belt pack worn by the viewer.

Figure 4:
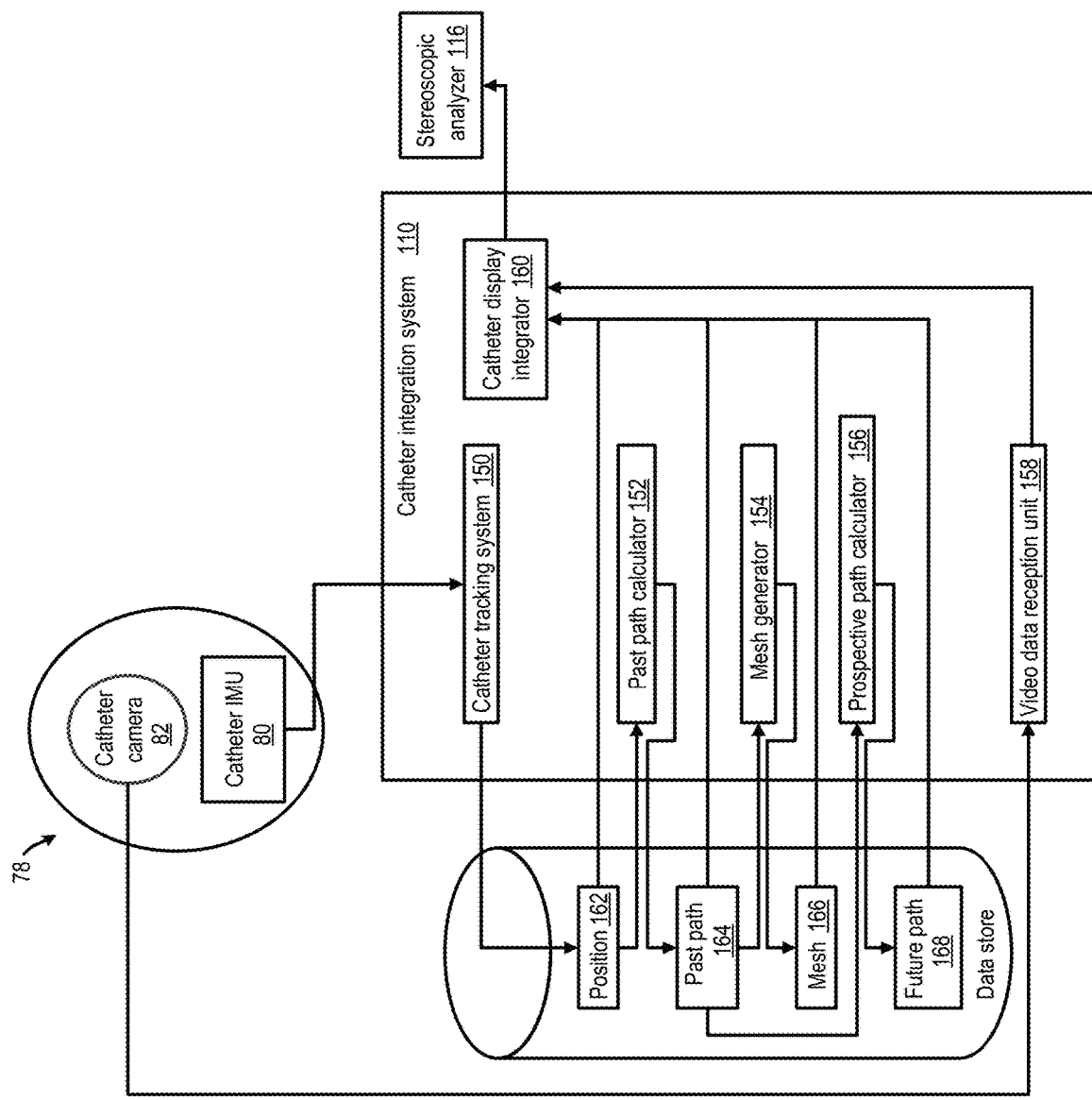
FIG. 4 is a block diagram illustrating a catheter integration system forming part of the display system in FIG. 3 and further illustrates the catheter.

FIG. 4 illustrates components of the viewing system 20 in more detail, in particular, components of the catheter integration system 110 and their relationship with the catheter IMU 80 and the catheter camera 82 in the tip 78 and the stereoscopic analyzer 116.

The catheter integration system 110 includes a catheter tracking system 150, a past path calculator 152, a mesh generator 154, a prospective path calculator 156, a video data reception unit 158, and a catheter display integrator 160. The catheter tracking system 150 is connected to the catheter IMU 80. The catheter tracking system 150 calculates a position of the tip 78 based on movement detected by the catheter IMU 80. The catheter IMU 80 includes a number of tip tracking devices, including a number of gyroscopes and accelerometer to track its movement in six degrees of freedom. The catheter tracking system 150 stores a current position of the tip 78 as a position 162 in the data store 24. The catheter tracking system 150 continues to monitor the catheter IMU 80, continues to calculate a current position of the tip 78, and continues to store a current position of the tip 78 as a current position 162 in the data store 24.

The catheter display integrator 160 receives the current position 162 from the data store 24 and provides the current position 162 to the stereoscopic analyzer 116. The stereoscopic analyzer 116 displays the current position 162 of the tip 78 as a rendering to the viewer so that the viewer can see the position of the tip 78 as a rendering in three-dimensions.

Past path calculator 152 retrieves every position 162 at every moment in time from the data store 24. The past path calculator 152 calculates a past path of the tip 78 in three-dimensions and stores the past path as a past path 164 in the data store 24. The catheter display integrator 160 receives the past path 164 from the data store 24 and provides the past path 164 to the stereoscopic analyzer 116. The stereoscopic analyzer 116 displays the past path 164 to the viewer as a three-dimensional rendering.

The mesh generator 154 retrieves the past path 164 from the data store and generates a three-dimensional mesh around the past path 164. The mesh generator 154 then stores the mesh as a mesh 166 in the data store 24. The catheter display integrator 160 retrieves the mesh 166 from the data store 24 and provides the mesh 166 to the stereoscopic analyzer 116. The stereoscopic analyzer 116 displays the mesh 166 to the viewer. The stereoscopic analyzer 116 creates a three-dimensional rendering of the mesh 166 that, in some embodiments, overlays the past path 164.

The prospective path calculator 156 retrieves every position 162 of the tip 78 from the data store 24 and calculates a future path of the tip 78 based on the position 162 and past positions retrieved from the data store 24. The prospective path calculator 156 then stores the future path as a future path 168 in the data store 24. The catheter display integrator 160 retrieves the future path 168 from the data store 24 and provides the future path 168 to the stereoscopic analyzer 116. The stereoscopic analyzer 116 displays the future path 168 to the viewer as a three-dimensional rendering.

The video data reception unit 158 receives live video from the catheter camera 82. The video data reception unit 158 provides the live video data to the catheter display integrator 160. The catheter display integrator 160 provides the live video data to the stereoscopic analyzer 116. The stereoscopic analyzer 116 displays the live video data to the viewer. The live video data is a two-dimensional display that is displayed to the viewer at a certain predetermined distance in three-dimensional space. The catheter display integrator also integrates the mesh 166 with the video data from the video data reception unit 158 so that the mesh 166 is displayed on the video data. As the video data changes, with a changing position of the catheter 26 within the body 30 of the patient, the mesh 166 also changes accordingly.

Figure 5:
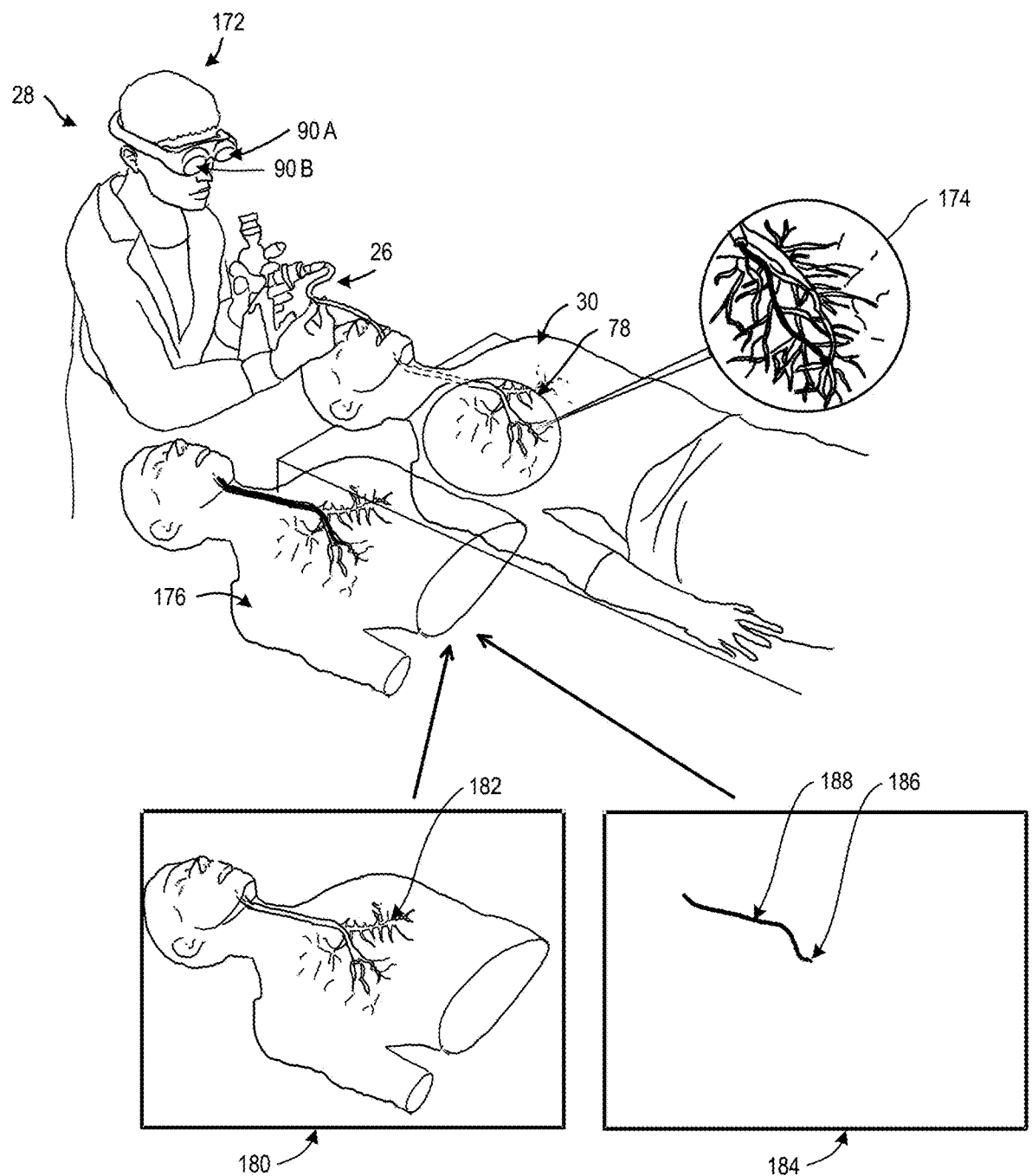
FIG. 5 is a perspective view illustrating a viewer in the form of a surgeon, the viewer seeing a body of a patient and a rendering of a body part inside the patient and further seeing a rendering of a tip of a catheter and a past path of the tip.

FIG. 5 illustrates the use of the viewing system 20 as hereinbefore described by a viewer 172 in the form of a surgeon who uses the catheter 26 as a bronchoscope for purposes of examining a body part 174 comprising segmental bronchi in lungs of a patient.

The viewer 172 can see the body 30 of the patient through the left and right wave guides 90A and 90B. The body part 174 is inside the body 30 of the patient, thus the viewer cannot see the real (i.e., physical) body part 174.

The viewer 172 also sees a three-dimensional rendering 176 which is based on the image data 70 as hereinbefore described. In the particular embodiment, the rendering 176 is located next to the body 30 of the patient. The rendering 176 is included in the figure to show the location where the viewer 172 perceives the rendering 176 relative to the body 30 of the patient, although it will be understood that, from the viewpoint of the reader of this document, the rendering 176 does not exist in the real world. The insert 180 shows that the viewer 172 can see a three-dimensional rendering 182 of the body part 174 as part of the rendering 176.

The viewer 172 inserts the tip 78 of the catheter 26 into a mouth of the patient. The viewer 172 then progresses the tip 78 into the body part 174. The locations of the tip 78 are monitored at instances that are closely spaced in time as hereinbefore described, and its past path is stored in three-dimensions. Sampling times may vary depending on the use case, and optimizations are possible, such as only capturing data while the endoscope is inside the patient's body, or after the user activates a "start recording/sampling" feature. The insert 184 shows that the rendering 176 includes a rendering 186 of the location of the tip 78 in three-dimensions and a rendering 188 of the past path of the tip 78 in three-dimensions. The renderings 182, 186, and 188 may be displayed to the viewer 172 simultaneously so that the viewer sees the renderings 186 and 188 within the rendering 182.

Figure 6:
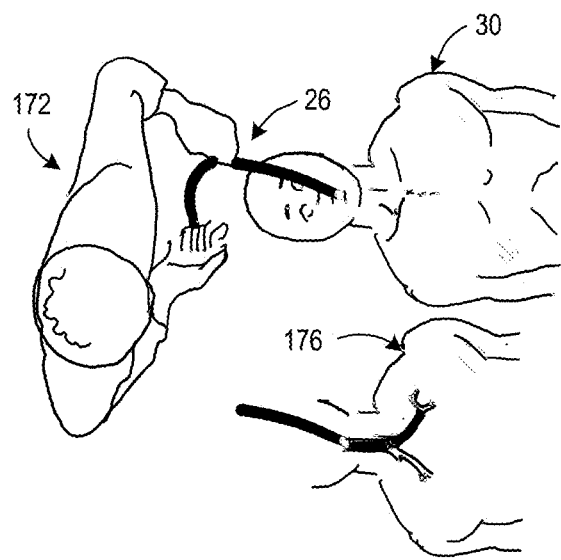
FIG. 6 is top plan view of FIG. 5.

FIG. 6 is a top plan view showing a location of the viewer 172 relative to the body 30 of the patient and further illustrates the location of the rendering 176 within the view of the viewer 172. The rendering 176 may be placed in any position relative to the body 30 of the patient, based on user preference, pre-programmed default settings, or any other suitable means. The particular relative location of body 30 of the patient to the rendering 176 in FIG. 6 is for illustration purposes only and should in no way be considered limiting.

Figure 7:
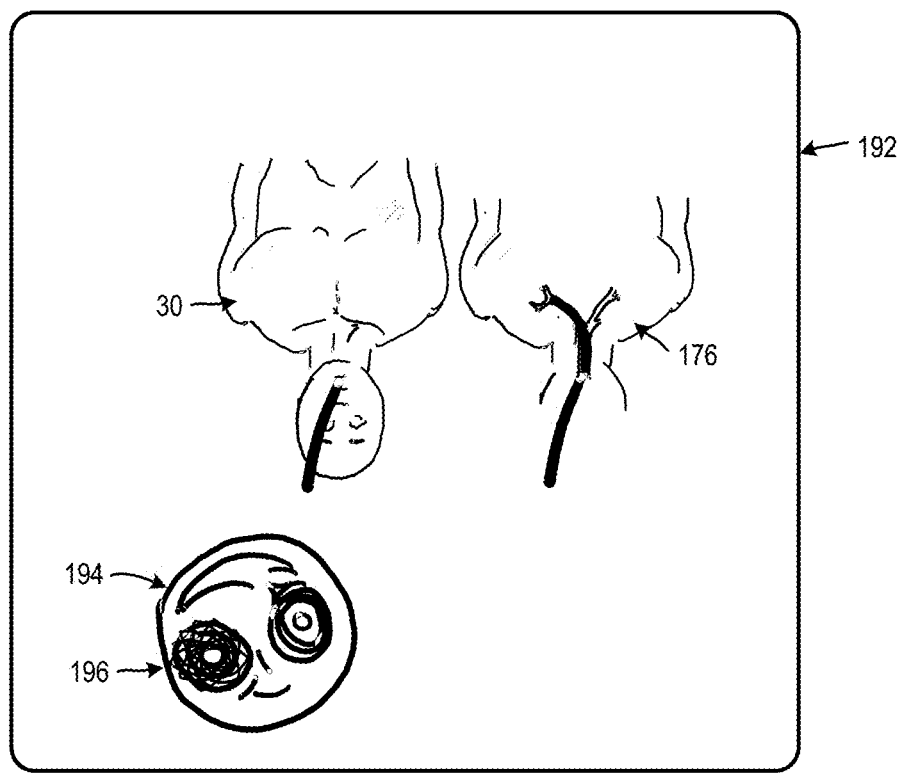
FIG. 7 is a view as seen by the viewer.

FIG. 7 illustrates a view 192 as seen by the viewer 172 in FIG. 6. The viewer 172 can see the actual body 30 of the patient and the rendering 176. The view 192 further includes a live video based on the video data that is captured by the catheter camera 82 in FIG. 4. The view 192 further shows a mesh 196 that overlays the video 194. The mesh 196 is a display of the mesh 166 in FIG. 4.

Figure 8:
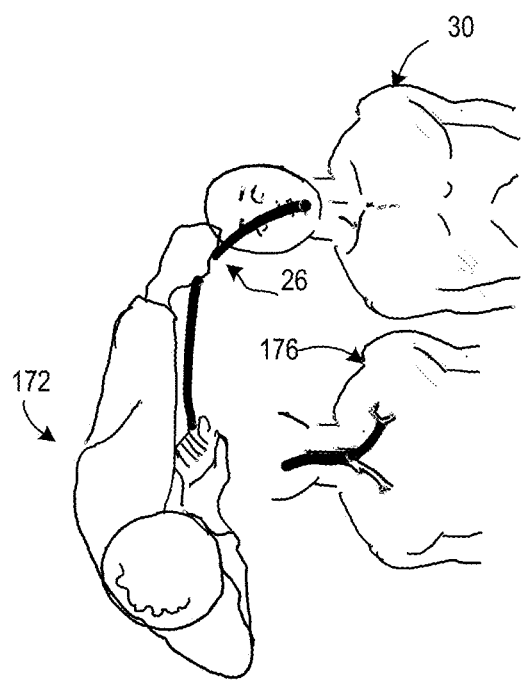
FIG. 8 is a view similar to FIG. 6 after the viewer has moved counterclockwise around the body of the patient and has moved their head counterclockwise to keep sight of the body of the patient.

In FIG. 8, the viewer 172 has moved counterclockwise around the body 30 of the patient and has also rotated their head counterclockwise to continue to see the body 30 of the patient. The display adjustment algorithm 112 detects the movement of the head of the viewer 172 and adjusts a positioning of the rendering 176 accordingly so that the rendering 176 appears to remain stationary relative to the body 30 of the patient within the view of the viewer 172.

Figure 9:
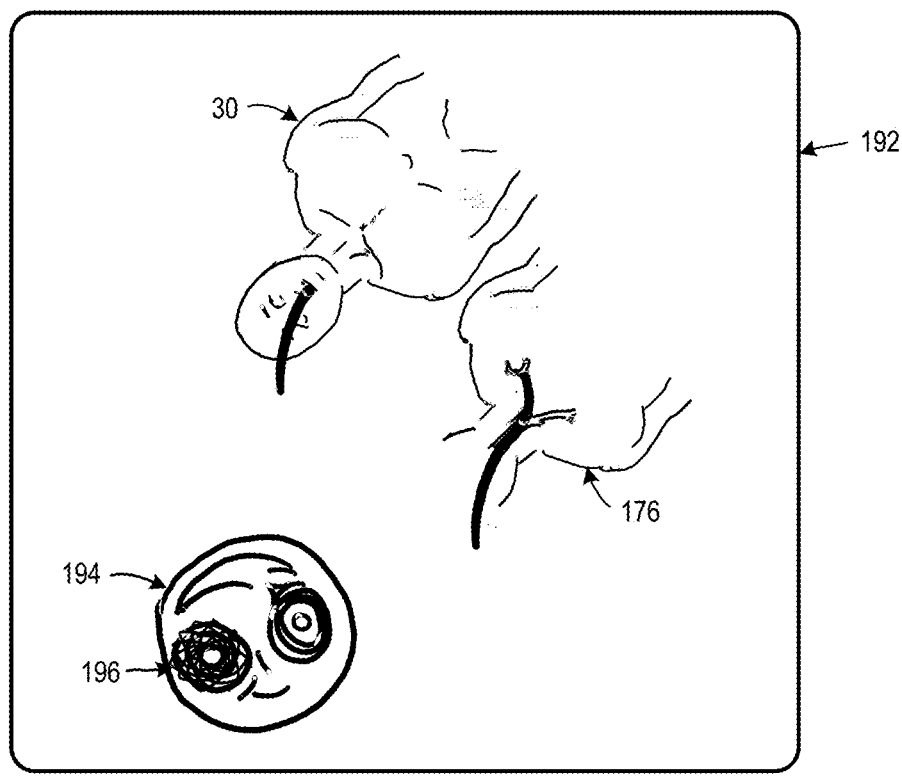
FIG. 9 is a view similar to FIG. 7 showing how the body of the patient and a rendering is modified within the view.

In FIG. 9, the body 30 of the patient has rotated clockwise relative to FIG. 7. The rendering 176 has also rotated clockwise so that it remains stationary relative to the body 30 of the patient. The location of the live video 194 has however not changed from the view 192 in FIG. 7 to the view 192 in FIG. 9. The viewer 172 thus sees the live video 194 and the mesh 196 in the same location and these components do not move upon movement of the head of the viewer 172. The viewer 172 can thus view the body 30 of the patient and the rendering 176 from different sides and angles without losing sight of the live video 194 and the mesh 196. The purpose of the mesh 196 may be to assist the viewer in guiding the tip 78 of the catheter 26 when the viewer 172 inserts the tip 78 into a passage in the body part 174 a second time after the mesh has been created, or during removal of the catheter as the catheter moves through the same path in the opposite direction. Some embodiments may have different viewing configurations for the virtual content (e.g., mesh 196, live video 194, rendering 176), in which some or all of the virtual content is fixed relative to real world coordinates, or are fixed relative to the viewer.

Figure 10:
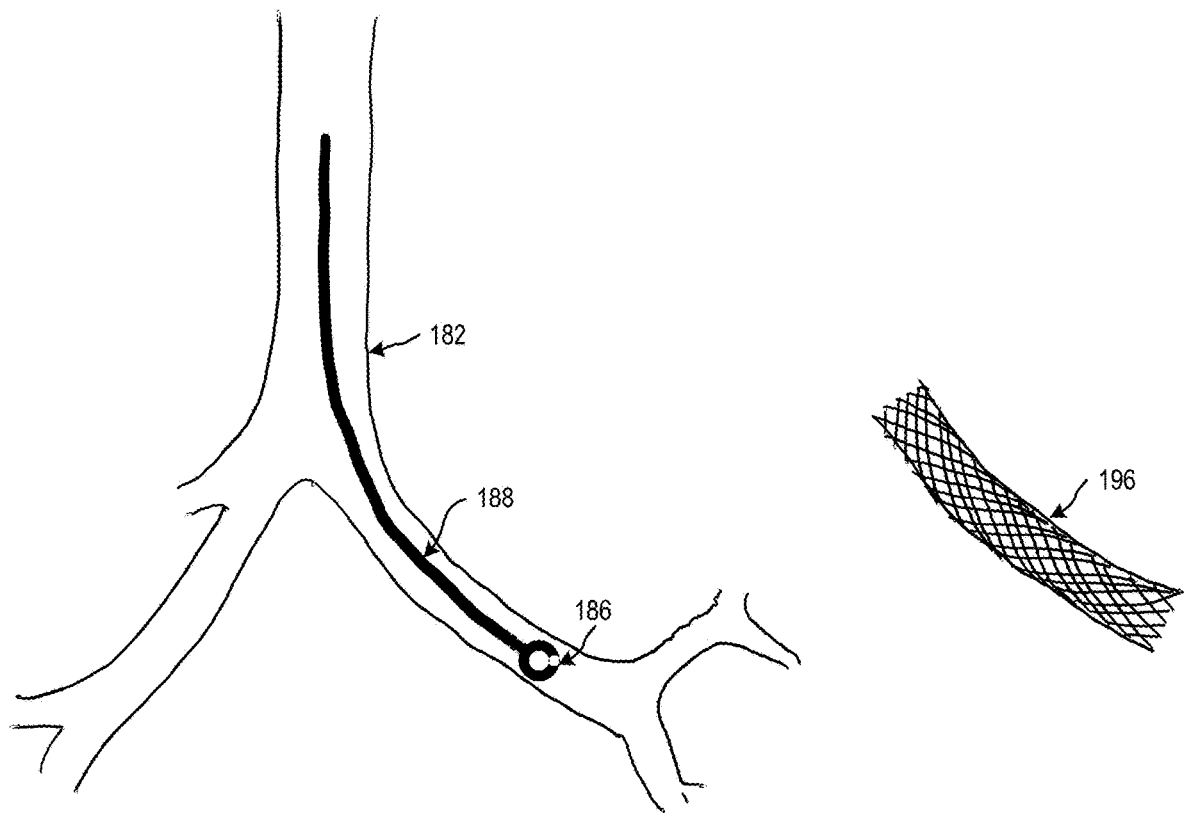
FIG. 10 illustrates renderings that are shown to the viewer in FIGS. 7 and 9 in enlarged detail.

FIG. 10 shows components of the rendering 176 that are displayed to the viewer that are too small to be seen in the views of FIGS. 7 and 9. The viewer 172 sees the renderings 182, 186 and 188 of the body part 174, the tip 78 and the past path of the tip. The viewer also sees a three-dimensional rendering of the mesh 196. The mesh 196 is shown separated from the renderings 182, 186 and 188 for purposes of illustration, although it should be understood that the mesh 196 may overlay the rendering 182 of the body part 174.

The implementation described above uses a CT scanner 22 to scan the body part 174. A CT scanner has transmitter in the form of an x-ray transmitter, a receiver in the form of an x-ray detector, and transmits and receives waves in the form of x-ray waves. It may be possible to use other scanning devices that use other transmitters and receivers and transmit and detect different waves. For example, a sonar system uses a sound transmitter to transmit a sound wave and a sound receiver to receive a sound wave. A visual system may include a light source that is inserted into the body part that transmits a light wave and have a camera that is located within the body part that captures a light wave reflected from the body part.

CT scanners are, however, preferred over other scanning devices because CT scanners provide very highly detailed raw data of the body part in three-dimensions and such data can readily be converted with an image generation unit to create three-dimensional image data. CT data also as the advantage that it can include data with respect to particular substances, materials, and densities of materials. The implementation described shows a rendering 176 placed next to the body 30 of a patient in the view 192 of the viewer 172. It may also be possible to match the rendering with the body 30 of the patient so that the rendering of the body part be where the actual body part is and the rendering of the tip of the catheter is where the actual position of the tip of the catheter is.

Aspects of the invention can also be implemented without a catheter. For example, it may be possible to scan a body of a patient to determine a growth and for a viewer to use a display system to overlay a rendering of the growth in three-dimensions on the actual body of the patient. In this manner, the viewer can "see" the growth "within' the actual body of the patient.

Figure 11:
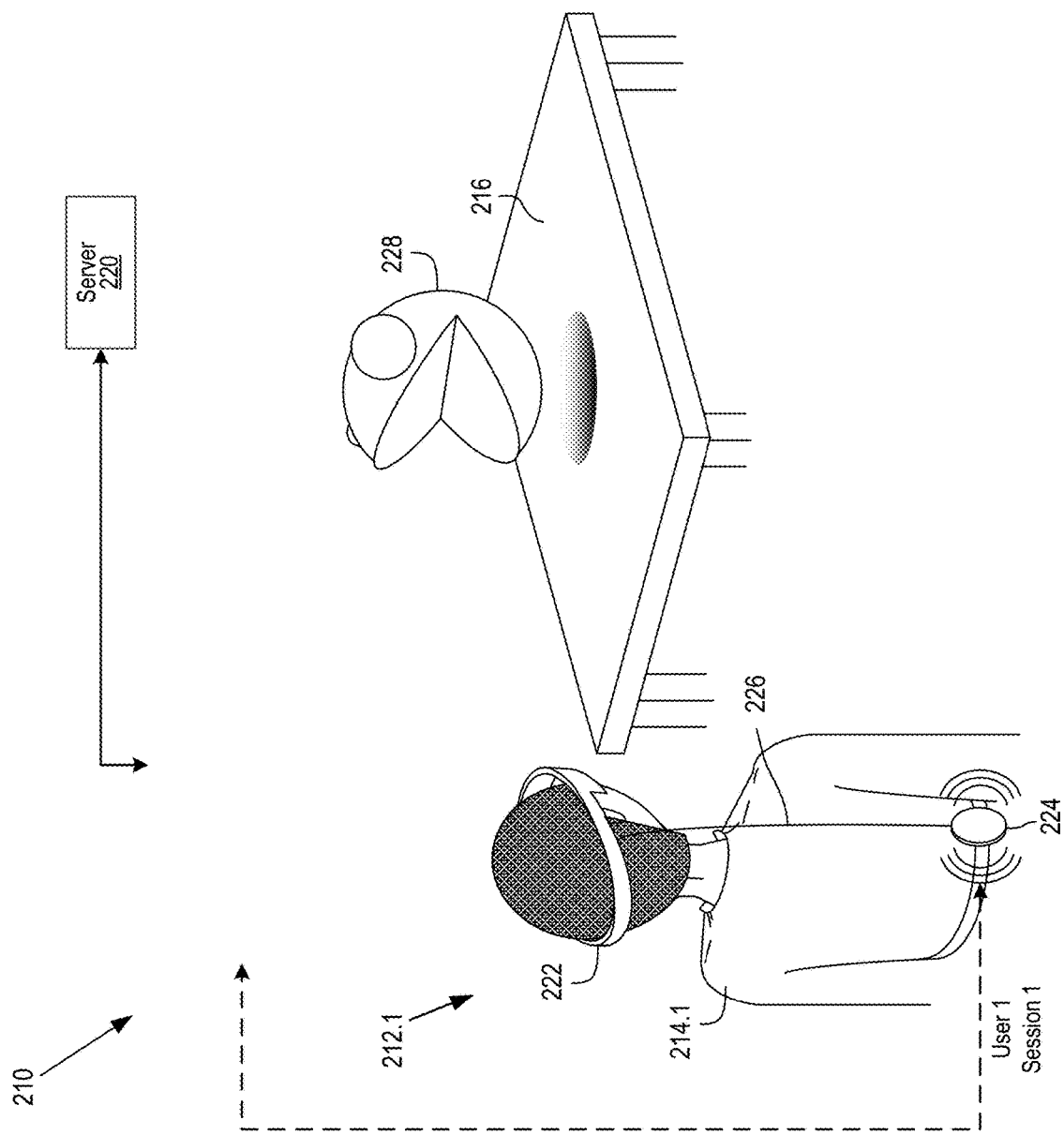
FIG. 11 is a partial perspective view and a partial block diagram illustrating a viewing system, according to an embodiment of the invention, a real-world object in the form of a table, and a first user interacting with the viewing system.

FIG. 11 of the accompanying drawings illustrates a viewing system 210, according to another embodiment of the invention, including a first viewing device 212.1 that is worn by a first user 214.1, a real object in the form of a table 216, a network 218 and a server 220.

The first viewing device 212.1 includes a head unit 222, a belt pack 224 and a cable connection 226. The first user 214.1 secures the head unit 222 to their head and the belt pack 224 remotely from the head unit 222 on their waist. The cable connection 226 connects the head unit 222 to the belt pack 224. The head unit 222 includes technologies that are used to display a virtual object or objects to the first user 214.1 while the first user 214.1 is permitted to see real objects such as the table 216. The belt pack 224 includes primarily processing and communications capabilities of the first viewing device 212.1. In another embodiment, the processing and communication capabilities may reside entirely in the head unit 222, thus dispensing the need for the belt pack 224, or may be located in another device such as a backpack.

The belt pack 224 is connected via a wireless connection to the network 218. The server 220 is connected to the network 218 and holds data representative of local content. The belt pack 224 downloads the data representing the local content from the server 220 via the network 218. The belt pack 224 provides the data via the cable connection 226 to the head unit 222. The head unit 222 typically includes a display that has a light source, for example a laser light source or a light emitting diode (LED) light source, and a waveguide that guides the light In use, the first user 214.1 mounts the head unit 222 to their head and the belt pack 224 to their waist. The belt pack 224 downloads image data over the network 218 from the server 220. The first user 214.1 can see the table 216 through a display of the head unit 222. A projector forming part of the head unit 222 receives the image data from the belt pack 224 and generates light based on the image data. The light travels through one or more of the waveguides forming part of the display of the head unit 222. The light then leaves the waveguide and propagates onto a retina of an eye of the first user 214.1. The projector generates the light in a pattern that is replicated on a retina of the eye of the first user 214.1. The light that falls on the retina of the eye of the first user 214.1 has a selected field of depth so that the first user 214.1 perceives an image at a preselected depth behind the waveguide. In addition, both eyes of the first user 214.1 receive slightly different images so that a brain of the first user 214.1 perceives a three-dimensional image or images at selected distances from the head unit 222. In the present example, the first user 214.1 perceives the local content 228 as an augmentation to seeing the table 216. The proportions of the local content 228 and its location and distance from the first user 214.1 are determined by the data representing local content 228 and various coordinate frames that are used to display the local content 228 to the first user 214.1.

The local content 228 is not visible from the perspective of the drawing and is only visible to the first user 214.1 due to their use of the first viewing device 212.1. The local content 228 initially resides as data structures within vision data and algorithms in the belt pack 224. The data structures then manifest themselves as light when the projectors of the head unit 222 generate light based on the data structures. Although the local content 228 has no existence in three-dimensional space in front of the first user 214.1, the local content 228 is still represented in FIG. 1 in three-dimensional space. The visualization of computer data in three-dimensional space is used throughout this description to illustrate how the data structures that facilitate the renderings that are perceived by one or more users relate to one another within the data structures in the belt pack 224.

Figure 12:
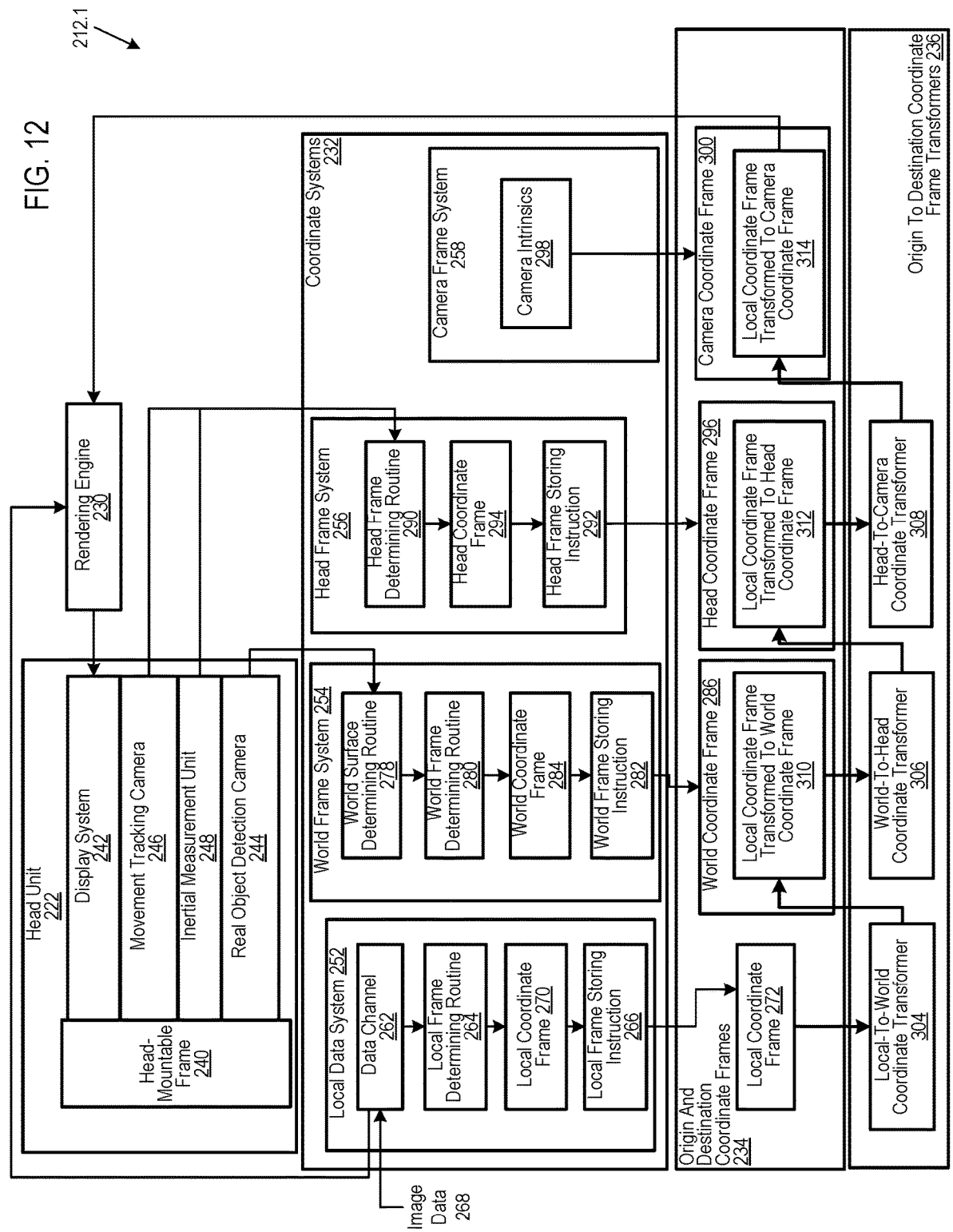
FIG. 12 is a block diagram of a first viewing device forming part of the viewing system.

FIG. 12 illustrates components of the first viewing device 12.1 in more detail, including the head unit 222, and various components forming part of the vision data and algorithms, including a rendering engine 230, various coordinate systems 232, various origin and destination coordinate frames 234, and various origin to destination coordinate frame transformers 236.

The head unit 222 includes a head-mountable frame 240, a display system 242, a real object detection camera 244, a movement tracking camera 246, and an inertial measurement unit 248.

The head-mountable frame 240 has a shape that is securable to the head of the first user 214.1 in FIG. 11. The display system 242, real object detection camera 244, movement tracking camera 246, and inertial measurement unit 248 are mounted to the head-mountable frame 240 and therefore move together with the head-mountable frame 240.

The coordinate systems 232 include a local data system 252, a world frame system 254, a head frame system 256, and a camera frame system 258.

The local data system 252 includes a data channel 262, a local frame determining routine 264 and a local frame storing instruction 266. The data channel 262 can be an internal software routine, a hardware component such as an external cable or a radio frequency receiver, or a hybrid component such as a port that is opened up. The data channel 262 is capable of receiving image data 268 representing local content.

The local frame determining routine 264 is connected to the data channel 262. The local frame determining routine 264 determines a local coordinate frame 270. The local coordinate frame may, for example, be based on a top edge relative to a bottom edge of a browser window, head and feet of a character, etc. The local frame storing instruction 266 is connected to the local frame determining routine 264. One skilled in the art will understand that software modules and routines are "connected" to one another through subroutines, calls, etc. The local frame storing instruction 266 stores the local coordinate frame 270 as a local coordinate frame 272 within the origin and destination coordinate frames 234.

The rendering engine 230 is connected to the data channel 262. The rendering engine 230 receives the image data 268 from the data channel 262.

The display system 242 is connected to the rendering engine 230. The display system 242 includes components that transform the image data 268 into visible light. The visible light forms two patterns, one for each eye. The visible light enters eyes of the first user 214.1 in FIG. 11 and is detected on retinas of the eyes of the first user 214.1.

The real object detection camera 244 is representative of one or more cameras that capture images from different sides of the head-mountable frame 240. The movement tracking camera 246 is also representative of one or more cameras that capture images on sides of the head-mountable frame 240. One camera may be used instead of the two cameras representing the real object detection camera 244 and the movement tracking camera 246.

The inertial measurement unit 248 includes a number of devices that are used to detect movement of the head unit 222. The inertial measurement unit 248 may include a gravitation sensor, one or more accelerometers and one or more gyroscopes. The sensors of the inertial measurement unit 248, in combination, track movement of the head unit 222 in at least three orthogonal directions and about at least three orthogonal axes.

The world frame system 254 includes a world surface determining routine 278, a world frame determining routine 280, and a world frame storing instruction 282. The world surface determining routine 278 is connected to the real object detection camera 244. The world surface determining routine 278 receives images that are captured by the real object detection camera 244 and processes the images to identify surfaces in the images. A depth sensor (not shown) determines distances to the surfaces. The surfaces are thus represented by data in three dimensions including their sizes, shapes, and distances from the real object detection camera. The world frame determining routine 280 is connected to the world surface determining routine 278 and determines a world coordinate frame 284 based on the locations of the surfaces as determined by the world surface determining routine 278. The world frame storing instruction 282 is connected to the world frame determining routine 280 to receive the world coordinate frame 284 from the world frame determining routine 280. The world frame storing instruction 282 stores the world coordinate frame 284 as a world coordinate frame 286 within the origin and destination coordinate frames 234.

The head frame system 256 includes a head frame determining routine 290 and a head frame storing instruction 292. The head frame determining routine 290 is connected to the movement tracking camera 246 and the inertial measurement unit 248. The head frame determining routine 290 uses data from the movement tracking camera 246 and the inertial measurement unit 248 to calculate a head coordinate frame 294. For example, the inertial measurement unit 248 has a gravitation sensor that determines the direction of gravitational force relative to the head unit 222. The movement tracking camera 246 continually captures images that are used by the head frame determining routine 290 to refine the head coordinate frame 294. The head unit 222 moves when the first user 214.1 in FIG. 11 moves their head. The movement tracking camera 246 and the inertial measurement unit 248 continuously provide data to the head frame determining routine 290 so that the head frame determining routine 290 can update the head coordinate frame 294.

The head frame storing instruction 292 is connected to the head frame determining routine 290 to receive the head coordinate frame 294 from the head frame determining routine 290. The head frame storing instruction 292 stores the head coordinate frame 294 as a head coordinate frame 296 among the origin and destination coordinate frames 234. The head frame storing instruction 292 repeatedly stores the updated head coordinate frame 294 as the head coordinate frame 296 when the head frame determining routine 290 recalculates the head coordinate frame 294.

The camera frame system 258 includes camera intrinsics 298. The camera intrinsics 298 are dimensions of the head unit 222 that are features of its design and manufacture. The camera intrinsics 298 are used to calculate a camera coordinate frame 300 that is stored within the origin and destination coordinate frames 234.

The camera coordinate frame 300 includes all pupil positions of a left eye of the first user 214.1 in FIG. 11. When the left eye moves from left to right or up and down, the pupil positions of the left eye are located within the camera coordinate frame 300. In addition, the pupil positions of a right eye are located within a camera coordinate frame 300 for the right eye.

The origin to destination coordinate frame transformers 236 include a local-to-world coordinate transformer 304, a world-to-head coordinate transformer 306, and a head-to-camera coordinate transformer 308. The local-to-world coordinate transformer 304 receives the local coordinate frame 272 and transforms the local coordinate frame 272 to the world coordinate frame 286. The transformation of the local coordinate frame 272 to the world coordinate frame 286 is represented as a local coordinate frame transformed to world coordinate frame 310 within the world coordinate frame 286.

The world-to-head coordinate transformer 306 transforms from the world coordinate frame 286 to the head coordinate frame 296. The world-to-head coordinate transformer 306 transforms the local coordinate frame transformed to world coordinate frame 310 to the head coordinate frame 296 and the transformation is represented as a local coordinate frame transformed to head coordinate frame 312 within the head coordinate frame 296.

The head-to-camera coordinate transformer 308 transforms from the head coordinate frame 296 to the camera coordinate frame 300. The head-to-camera coordinate transformer 308 transforms the local coordinate frame transformed to head coordinate frame 312 to a local coordinate frame transformed to camera coordinate frame 314 within the camera coordinate frame 300. The local coordinate frame transformed to camera coordinate frame 314 is entered into the rendering engine 230. The rendering engine 230 displays the image data 268 representing the local content 228 based on the local coordinate frame transformed to camera coordinate frame 314.

Figure 13:
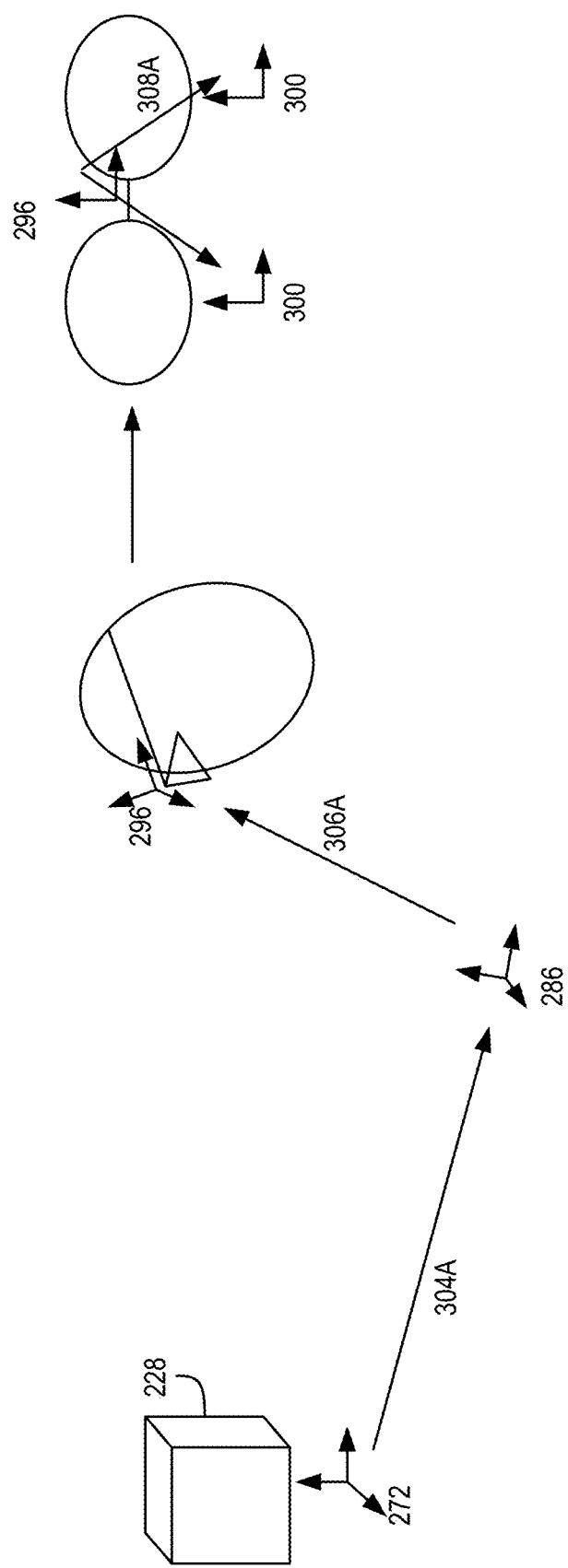
FIG. 13 is a schematic diagram illustrating how origin coordinate frames are transformed into destination coordinate frames for purposes of correct rendering of local content.

FIG. 13 is a spatial representation of the various origin and destination coordinate frames 234. The local coordinate frame 272, world coordinate frame 286, head coordinate frame 296, and camera coordinate frame 300 are represented in the figure. Each camera has its own camera coordinate frame 300 encompassing all pupil positions of one eye. Reference numerals 304A and 306A represent the transformations that are made by the local-to-world coordinate transformer 304, world-to-head coordinate transformer 306 and head-to-camera coordinate transformer 308 in FIG. 12, respectively.

By giving the virtual content its own coordinate frame, as opposed to being measured directly to the world coordinate frame, the virtual content may be given a more persistent frame position. For example, if a virtual lamp is placed on a table, there could be a plurality of data points on the table to provide placement input for relative positioning of the virtual lamp that does not substantially change over time. By contrast, if a world map is created as a function of a certain orientation and position, and the user changes position or orientation, thus necessitating a new world coordinate frame, the virtual lamp may continue to utilize the same local coordinate frame rather than adjust to a new world frame which may introduce jitter or positional shifts in the appearance of the lamp.

Figure 14:
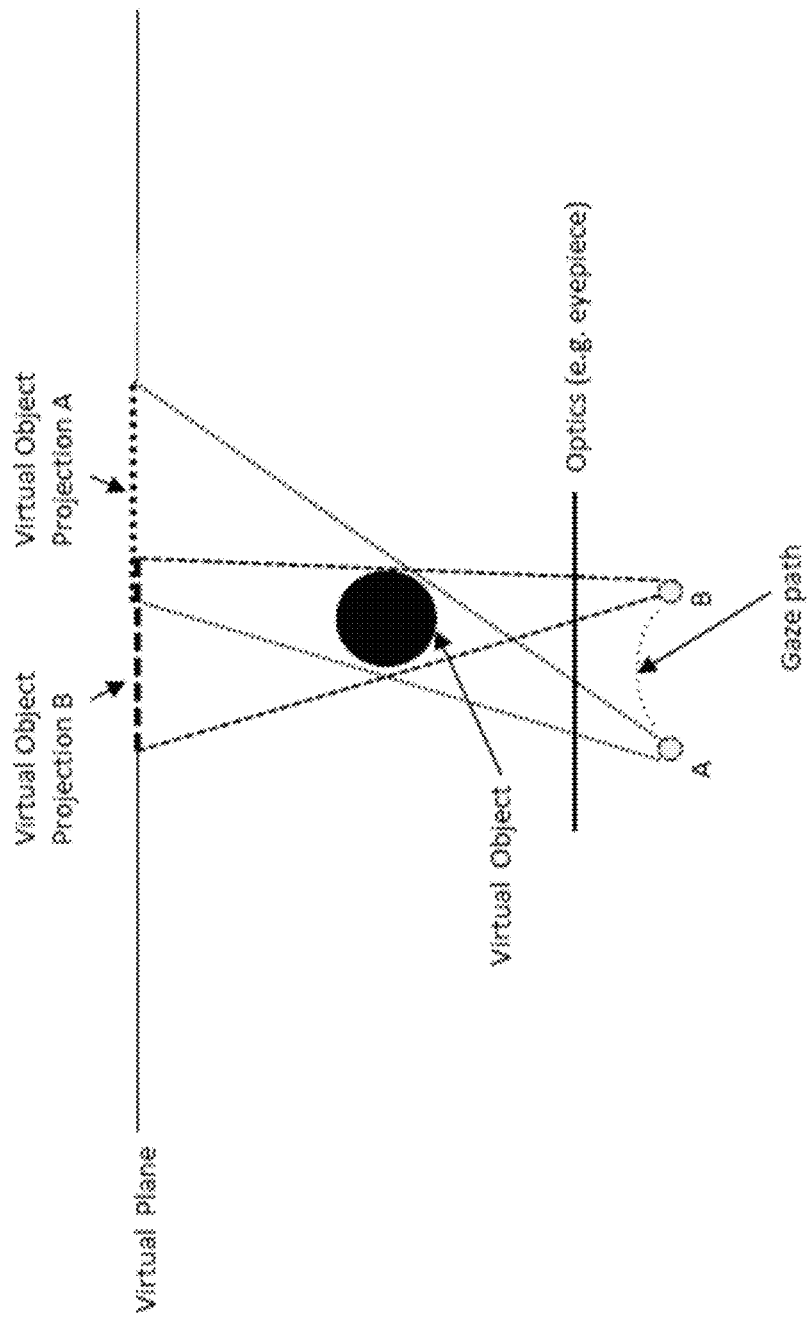
FIG. 14 is a top plan view illustrating pupil-based coordinate frames.

FIG. 14 depicts a camera render protocol for transforming from a head coordinate frame to a camera coordinate frame. A pupil for a single eye moves from position A to B. A virtual object that is meant to appear stationary will project onto a depth plane at one of the two positions A or B depending on the position of the pupil (assuming that the camera is configured to use a pupil as its coordinate frame). As a result, using a pupil coordinate frame transformed to a head coordinate frame will cause jitter in a stationary virtual object as the eye moves from position A to position B. This situation is referred to as view dependent display or projection.

Figure 15:
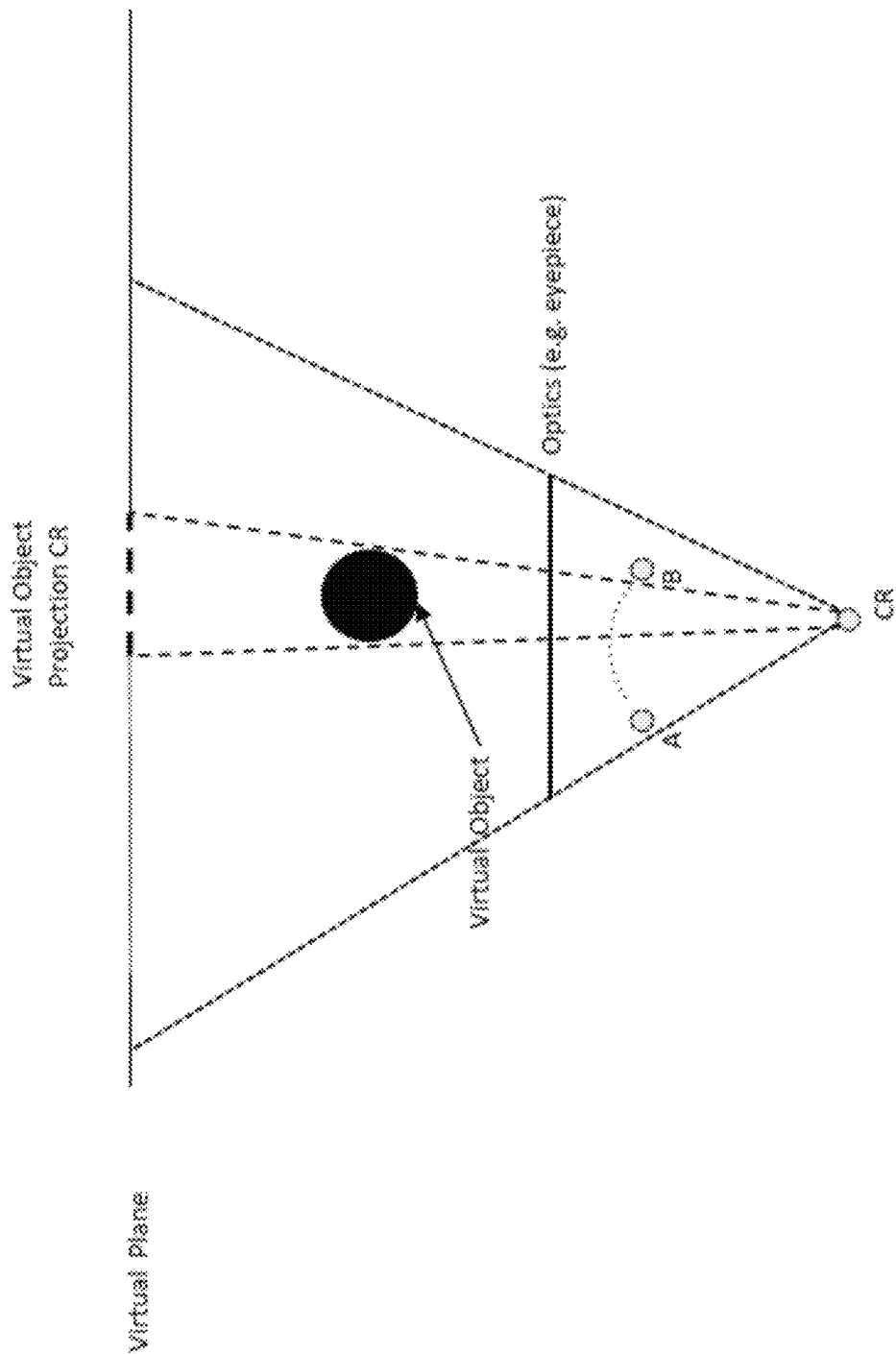
FIG. 15 is a top plan view illustrating a camera coordinate frame that includes all pupil positions.

As depicted in FIG. 15, a camera render (CR) frame is positioned and encompasses all pupil positions and object projection will now be consistent regardless of pupil positions A and B. The head coordinate frame transforms to the CR frame, which is referred to as view independent display or projection. An image reprojection may be applied to the virtual content to account for a change in eye position, however, as the rendering is still in the same position, jitter is minimized.

Figure 16:
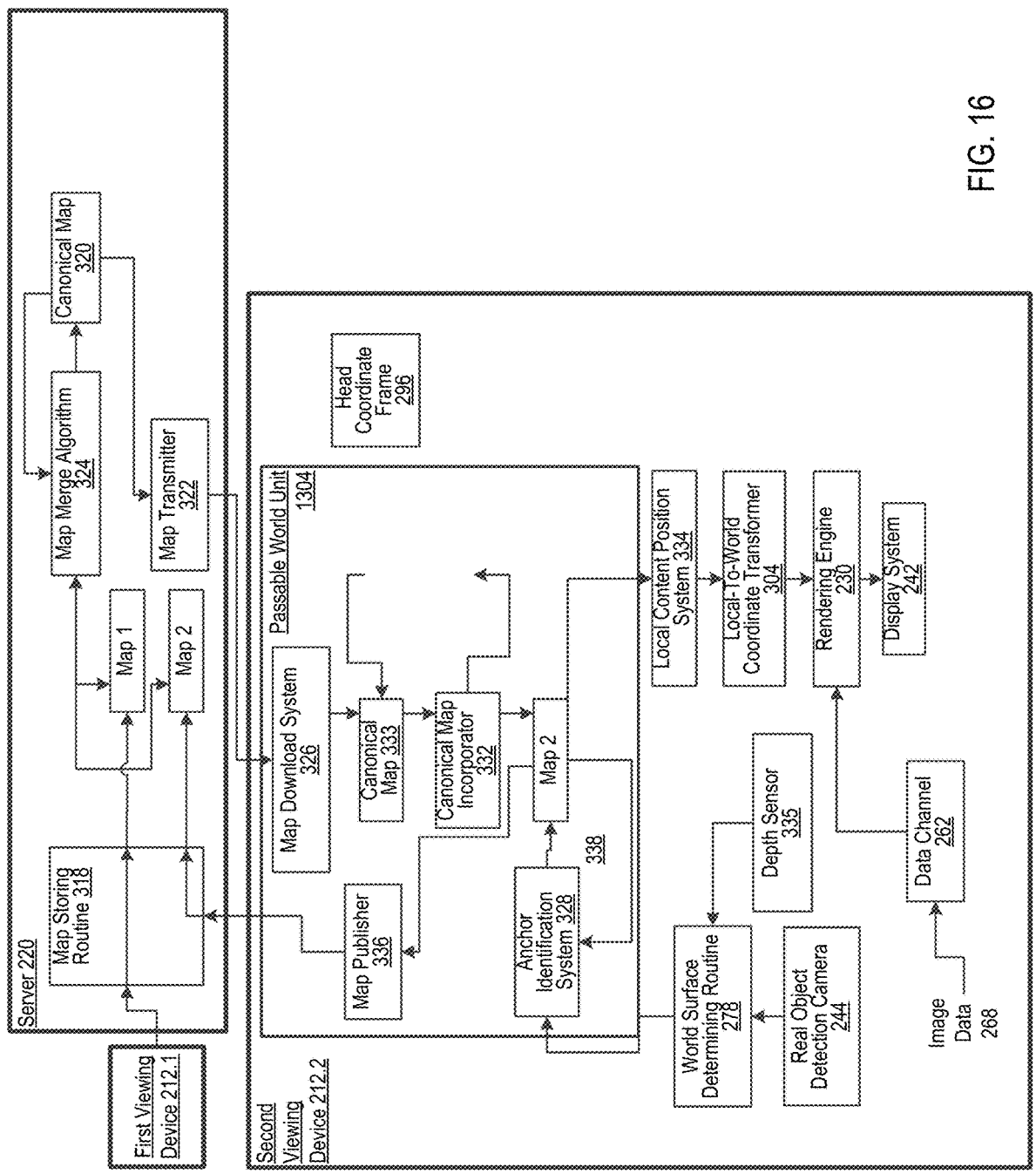
FIG. 16 is a block diagram of vision data and algorithms of a server, and first and second viewing devices of the viewing system.

FIG. 16 illustrates the first viewing device 212.1 and vision data and algorithms of a second viewing device 212.2 and the server 220 in more detail. Although not illustrated, the first viewing device 212.1 is configured the same as the second viewing device 212.2.

The server 220 has a map storing routine 318, a canonical map 320, a map transmitter 322, and a map merge algorithm 324 serving as a central server-side map generator.

In use, the first viewing device 212.1 generates a local tracking map (referred to hereinafter as "Map 1") and the map storing routine 318 receives Map 1 from the first viewing device 212.1. The map storing routine 318 then stores Map 1 on a storage device of the server 220 as the canonical map 320.

The second viewing device 212.2 includes a map download system 326, an anchor identification system 328, a localization module 330, a canonical map incorporator 332, a local content position system 334, and a map publisher 336.

In use, the map transmitter 322 sends the canonical map 320 to the second viewing device 212.2 and the map download system 326 downloads and stores the canonical map 320 as a canonical map 333 from the server 220.

The anchor identification system 328 is connected to the world surface determining routine 278. The anchor identification system 328 identifies anchors based on objects detected by the world surface determining routine 278. The anchor identification system 328 generates a second map (Map 2) using the anchors. As indicated by the cycle 338, the anchor identification system 328 continues to identify anchors and continues to update Map 2. The locations of the anchors are recorded as three-dimensional data based on data provided by the world surface determining routing 278. The world surface determining routine 278 receives images from the real object detection camera 244 and depth data from depth sensors 335 to determine the locations of surfaces and their relative distance from the depth sensors 335

The localization module 330 is connected to the canonical map 333 and Map 2. The localization module 330 repeatedly attempts to localize Map 2 to the canonical map 333. The canonical map incorporator 332 is connected to the canonical map 333 and Map 2. When the localization module 330 localizes Map 2 to the canonical map 333, the canonical map incorporator 332 incorporates the canonical map 333 into anchors of Map 2. Map 2 is then updated with missing data that is included in the canonical map.

The local content position system 334 is connected to Map 2. The local content position system 334 may, for example, be a system wherein a user can locate local content in a particular location within a world coordinate frame. The local content then attaches itself to one anchor of Map 2. The local-to-world coordinate transformer 304 transforms the local coordinate frame to the world coordinate frame based on the settings of the local content position system 334. The functioning of the rendering engine 230, display system 242, and data channel 262 have been described with reference to FIG. 12.

The map publisher 336 uploads Map 2 to the server 220. The map storing routine 318 of the server 220 then stores Map 2 within a storage medium of the server 220.

The map merge algorithm 324 merges Map 2 with the canonical map 320. When more than two maps, for example three or four maps, have been stored, the map merge algorithm 324 merges all the maps into the canonical map 320 to render a new canonical map 320. The map transmitter 322 then transmits the new canonical map 320 to any and all devices 212.1 and 212.2 that are in an area represented by the new canonical map 320. When the devices 212.1 and 212.2 localize their respective maps to the canonical map 320, the canonical map 320 becomes the promoted map.

Figure 17:
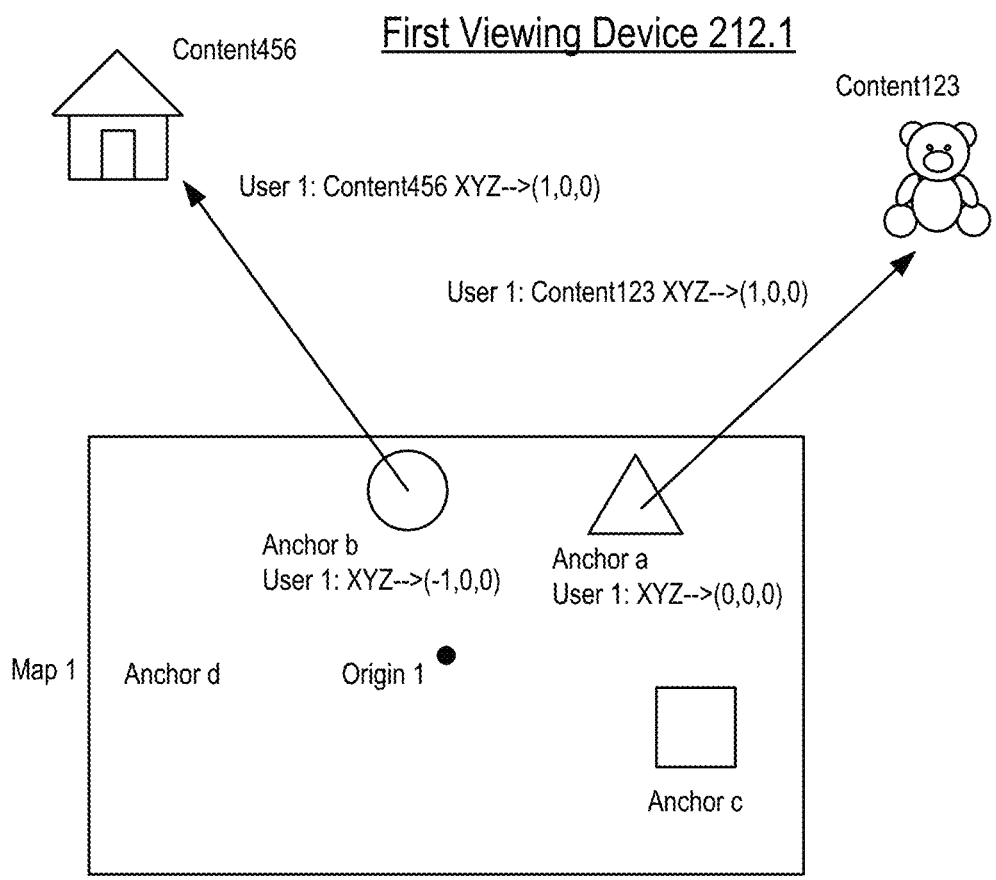
FIG. 17 is a two-dimensional representation of a three-dimensional first local tracking map (Map 1) that is generated by the first viewing device.

FIG. 17 illustrates Map 1 and local content (Content123 and Content456) on the first viewing device 212.1. Map 1 includes a number of anchors (Anchor a to Anchor d). From the perspective of the first viewing device 212.1, Anchor a, by way of example, has X, Y, and Z coordinates of (0,0,0) and Anchor b has X, Y, and Z coordinates (−1,0,0). Content123 is associated with Anchor a. Content123 may for example be a virtual object such as a virtual implant that has to be related to Anchor a so that all users will see the virtual implant in the same location after their respective systems have localized to a canonical map. In the present example, Content123 has an X, Y, and Z relationship relative to Anchor a of (1,0,0). Content456 has a relationship relative to Anchor b. In the present example, Content456 has an X, Y, and Z relationship of (1,0,0) relative to Anchor b. Map 1 also has an origin (Origin 1).

Figure 18:
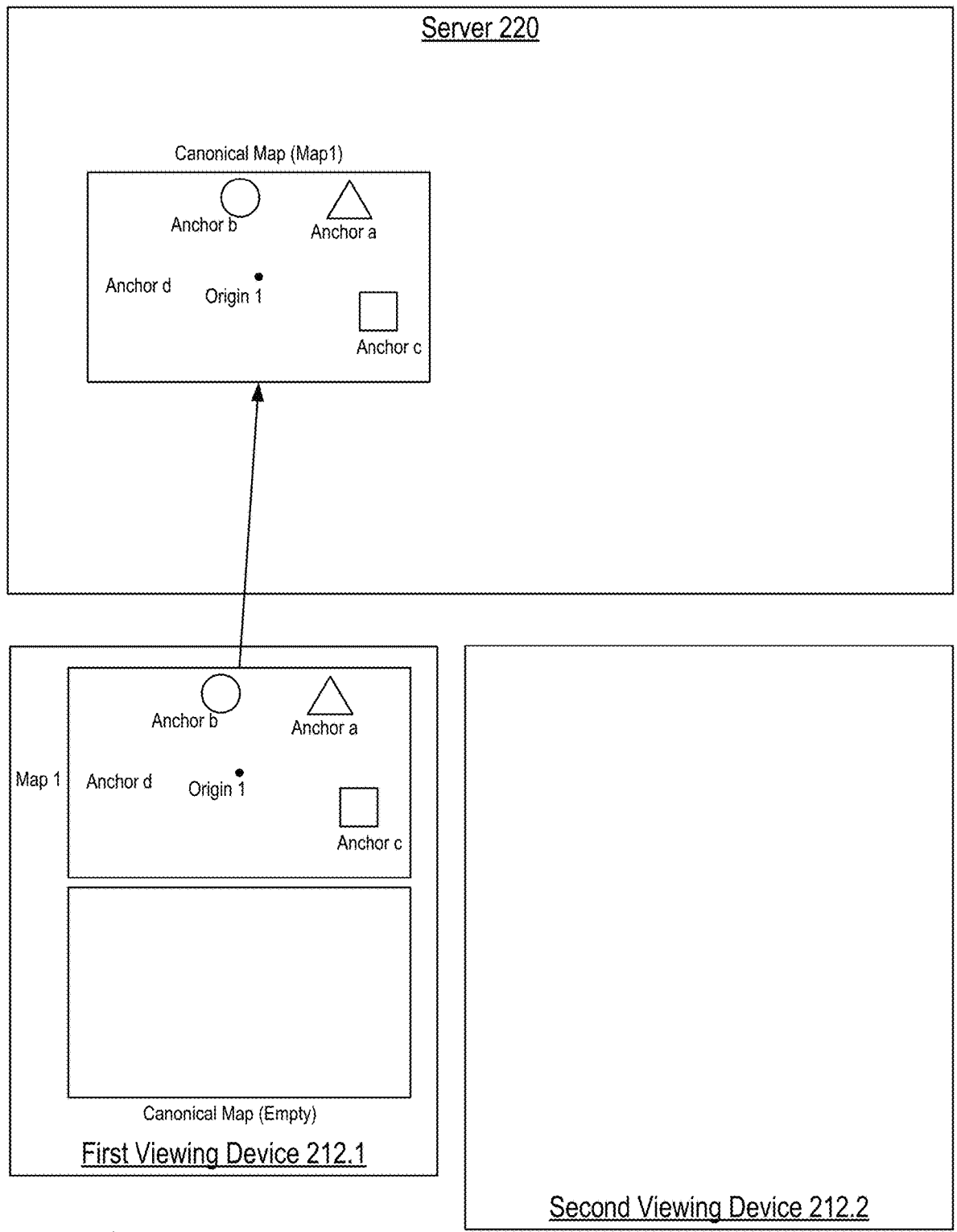
FIG. 18 is a block diagram illustrating upload of Map 1 from the first viewing device to the server.

In FIG. 18, the first viewing device 212.1 uploads Map 1 to the server 220. The server 220 now has a canonical map based on Map 1. The first viewing device 212.1 has a canonical map that is empty at this stage. The server 220, for purposes of discussion, includes no other maps other than Map 1. No maps are stored on the second viewing device 212.2.

The first viewing device 212.1 also transmits its Wi-Fi signature data to the server 220. The server 220 may use the Wi-Fi signature data to determine a rough location of the first viewing device 212.1 based on intelligence gathered from other devices that have, in the past, connected to the server 220 or other servers together with the GPS locations of such other devices that have been recorded.

The first viewing device 212.1 may now end the first session (See FIG. 11) and may disconnect from the server 220.

Figure 19:
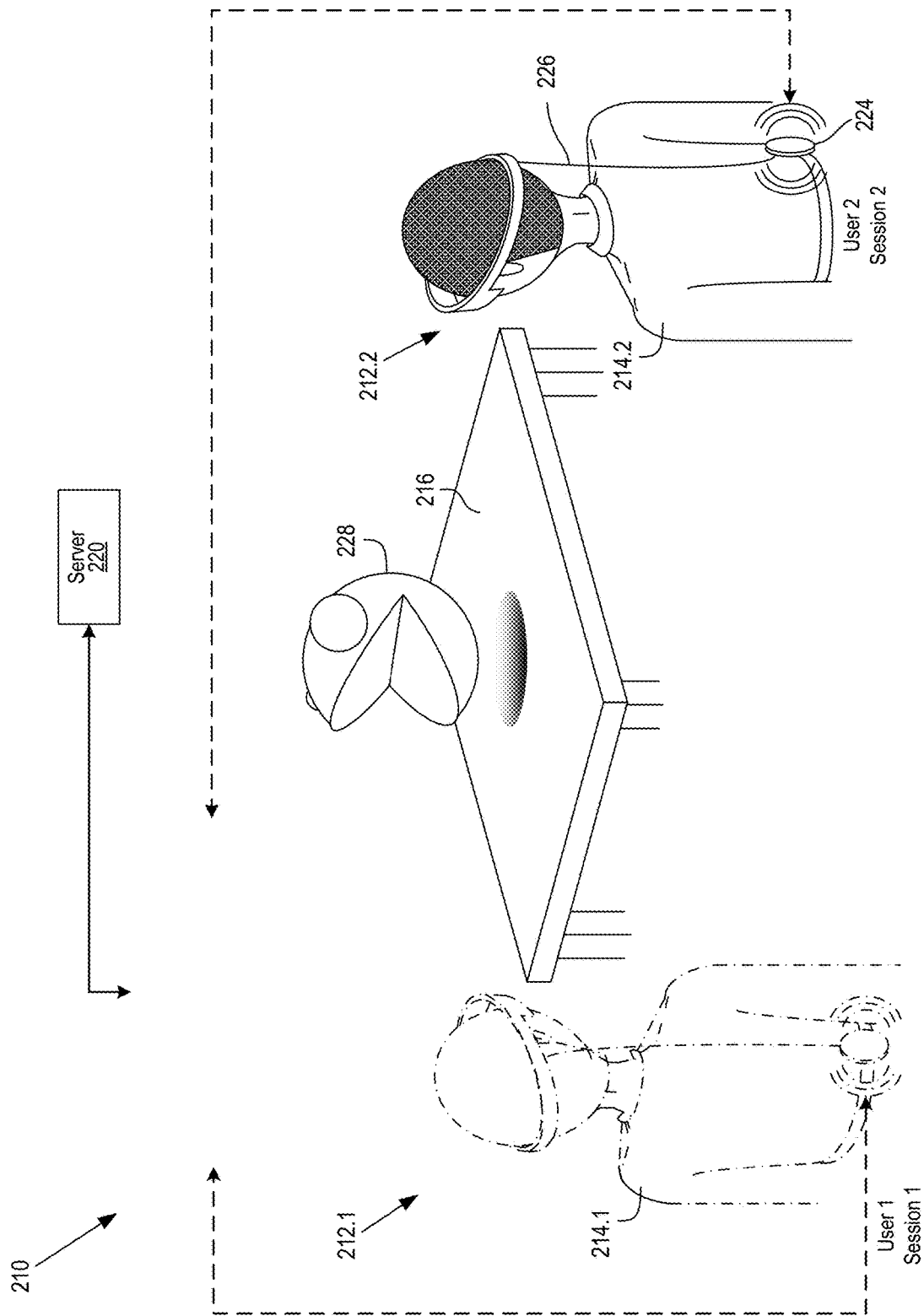
FIG. 19 is a view similar to FIG. 11 after the first user has terminated a first session and a second user has initiated a second session using a second viewing device forming part of the viewing system.

FIG. 19 shows the initiation of a second session by a second user 214.2. The first user 214.1 is shown in phantom lines because the first session by the first user 214.1 has ended. The second viewing device 212.2 begins to record objects. Various systems with varying degrees of granulation may be used by the server 220 to determine that the second session by the second viewing device 212.2 is in the same vicinity of the first session by the first viewing device 212.1. For example, Wi-Fi signature data, global positioning system (GPS) positioning data, GPS data based on Wi-Fi signature data or any other data that indicates a location may be included in the first and second viewing devices 212.1 and 212.2 to record their locations. Alternatively, the anchors that are identified by the second viewing device 212.2 may show a similarity to the anchors of Map 1.

Figure 20:
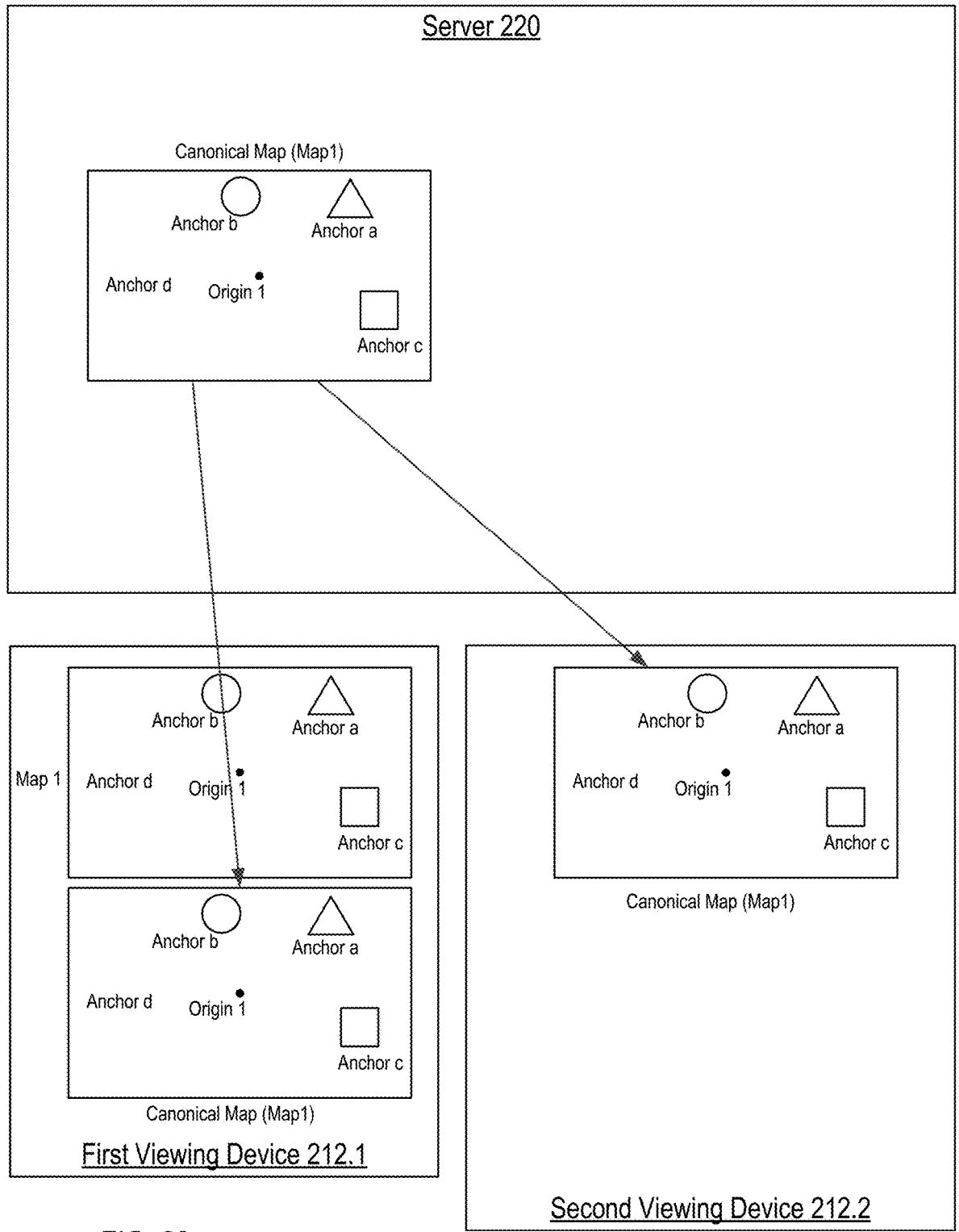
FIG. 20 is a block diagram illustrating download of a canonical map from the server to the second viewing device.

As shown in FIG. 20, the first and second viewing devices 212.1 and 212.2 download the canonical map 320 from the server 220. Map 1 on the second viewing device 212.2 includes anchors a to d and Origin 1. The server 220 may have multiple canonical maps for various locations and determines that the second viewing device 212.2 is in the same vicinity as the vicinity of the first viewing device 212.1 during the first session and sends the second viewing device 212.2 the canonical map for that vicinity.

Figure 21:
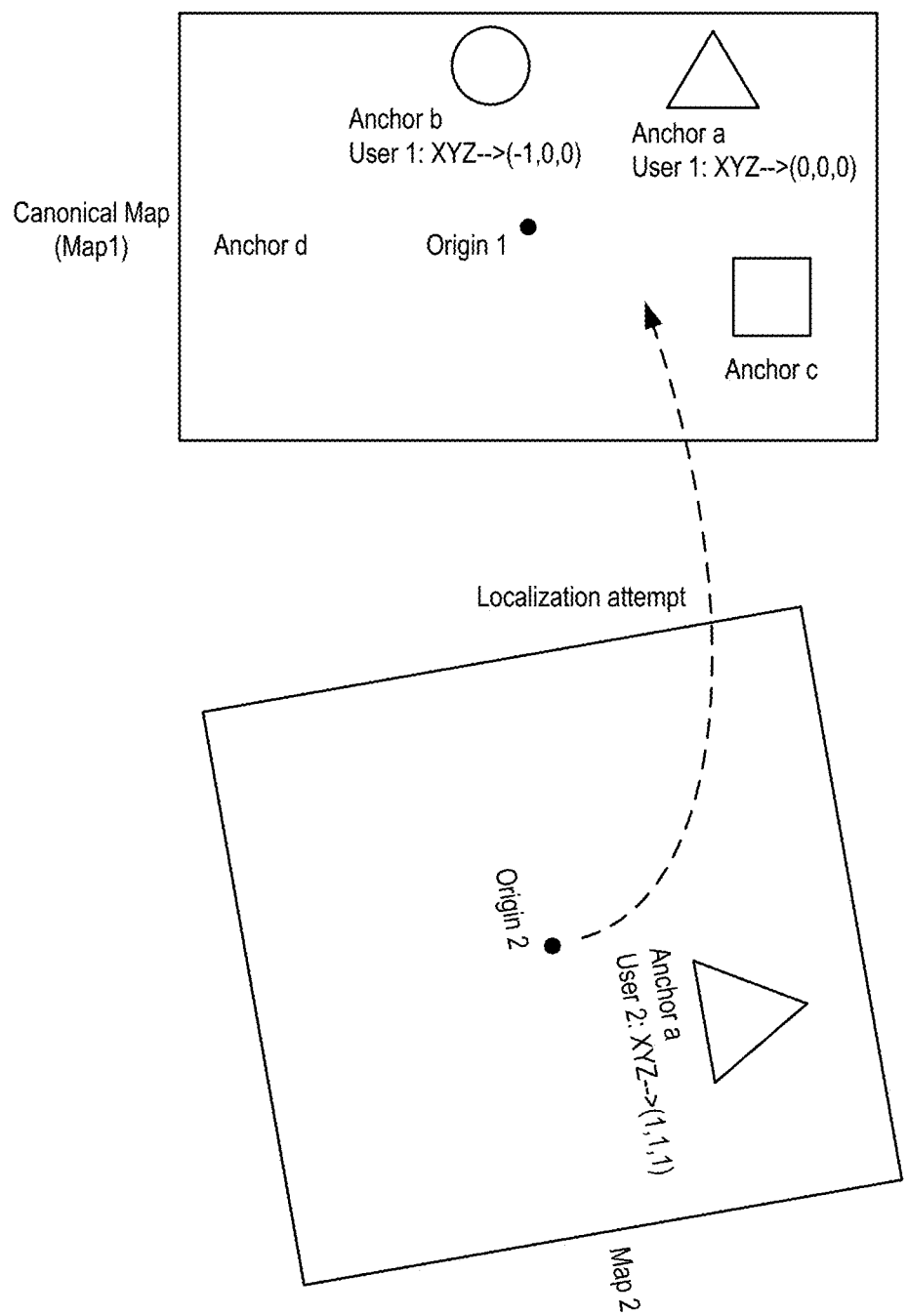
FIG. 21 is a two-dimensional representation of a second tracking map (Map 2) that is generated by the second viewing device and further illustrates a localization attempt that is made to localize Map 2 to the canonical map.

FIG. 21 shows the second viewing device 212.2 beginning to identify anchors for purposes of generating Map 2. The second viewing device 212.2 has only identified a single anchor, namely Anchor a. The X, Y, and Z coordinates of Anchor a for the second viewing device 212.2 are (1,1,1). The X, Y, and Z coordinates of Anchor a are thus different for Map 2 of the second viewing device 212.2 than what was determined for Map 1 of the first viewing device 212.1 and the canonical map. Map 2 also has its own origin (Origin 2). The second viewing device 212.2 immediately attempts to localize Map 2 to the canonical map. Because Map 2 has an insufficient number of anchors for purposes of localizing to the canonical map, the localization attempt fails.

Figure 22:
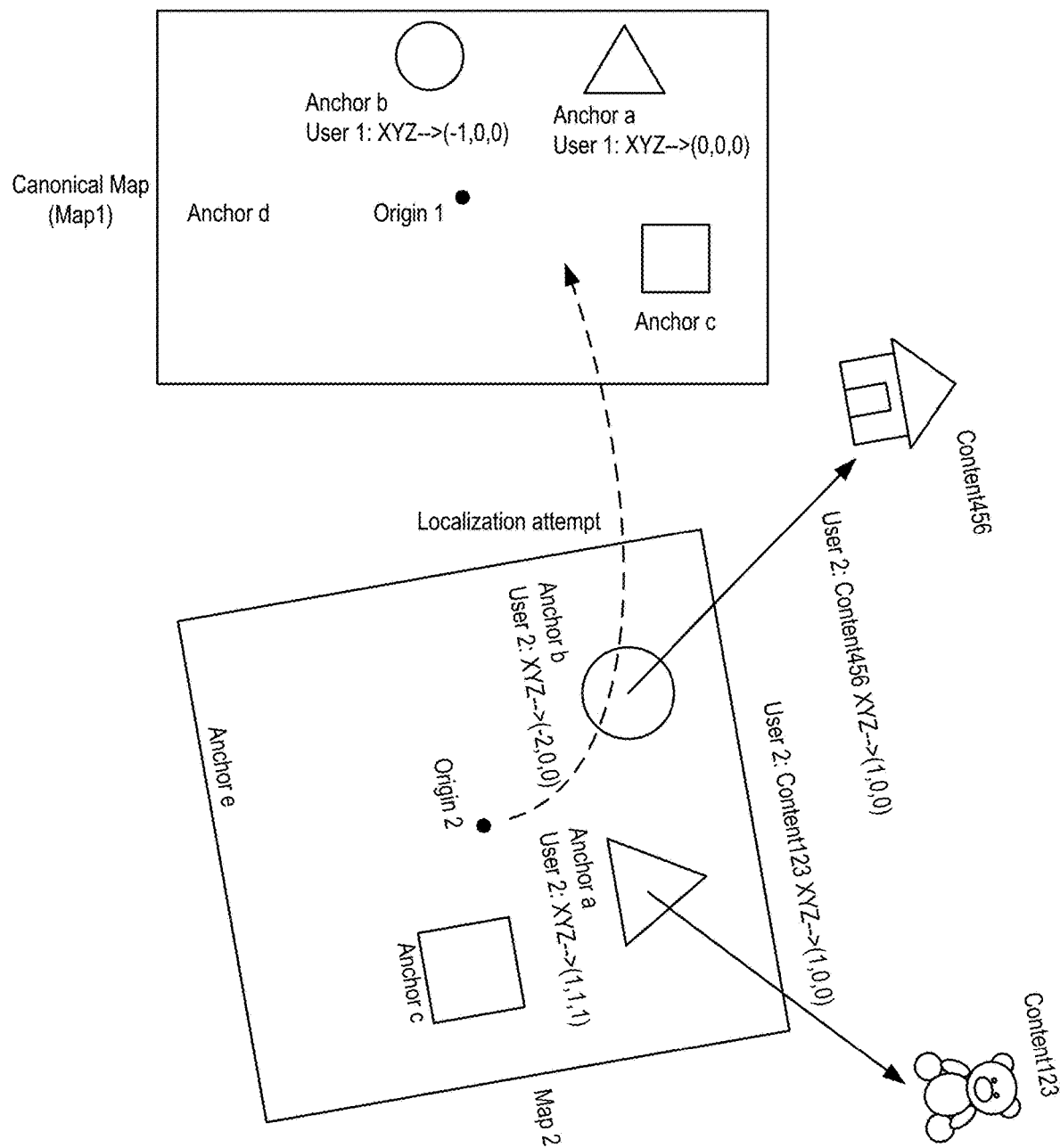
FIG. 22 is a view similar to FIG. 21 after Map 2 is further developed and local content is associated with anchors of Map 2.

FIG. 22 shows Map 2 after the second viewing device 212.2 has identified further anchors (Anchor b, Anchor c, and Anchor e) of Map 2. The second viewing device 212.2 again attempts to localize Map 2 to the canonical map. Because Map 2 has at least two anchors (Anchor a and Anchor b) that match two anchors of the canonical map, the localization attempt will succeed.

Furthermore, the second viewing device 212.2 has associated Content123 and Content456 to Anchors a and b of Map 2. Content123 has X, Y, and Z coordinates relative to Anchor a of (1,0,0). The coordinates of Content 123 relative to Anchor a are thus the same for the second viewing device 212.2 and for the first viewing device 212.1.

Similarly, the X, Y, and Z coordinates of Content456 relative to Anchor b in Map 2 are (1,0,0). The X, Y, and Z coordinates of Content456 relative to Anchor b for the second viewing device 212.2 are thus the same as for the first viewing device 212.1 in FIG. 17.

Figure 23:
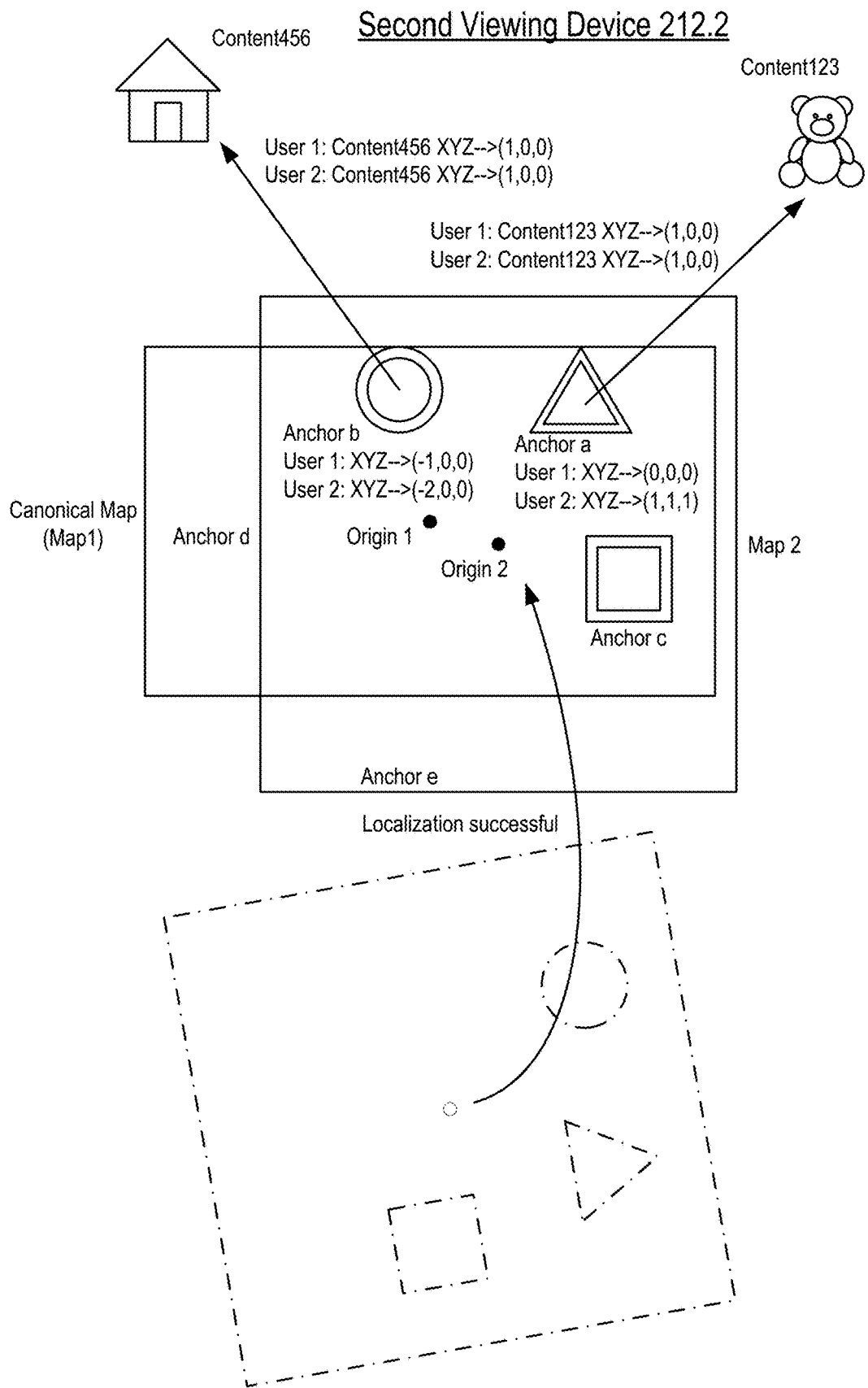
FIG. 23 is a view similar to FIG. 22 after a successful localization of Map 2 to the canonical map.

FIG. 23 illustrates a successful localization of Map 2 to the canonical map. Anchors a, b, and c are common to Map 1 and the canonical map. The canonical map also has Anchor d that is not included in Map 2, and Map 2 has Anchor e that is not included in the canonical map. What should be noted is that, for the second viewing device 212.2, Content 123 is in the same location relative to Anchor a for the second viewing device 212.2 as illustrated in FIG. 23 than for the first viewing device 212.1 as illustrated in FIG. 17. Content456 is also in the same location relative to Anchor b for the second viewing device 212.2 and for the first viewing device 212.1. The first and second users 214.1 and 214.2 thus perceive Content123 and Content456 in the same locations in the real world.

Figure 24:
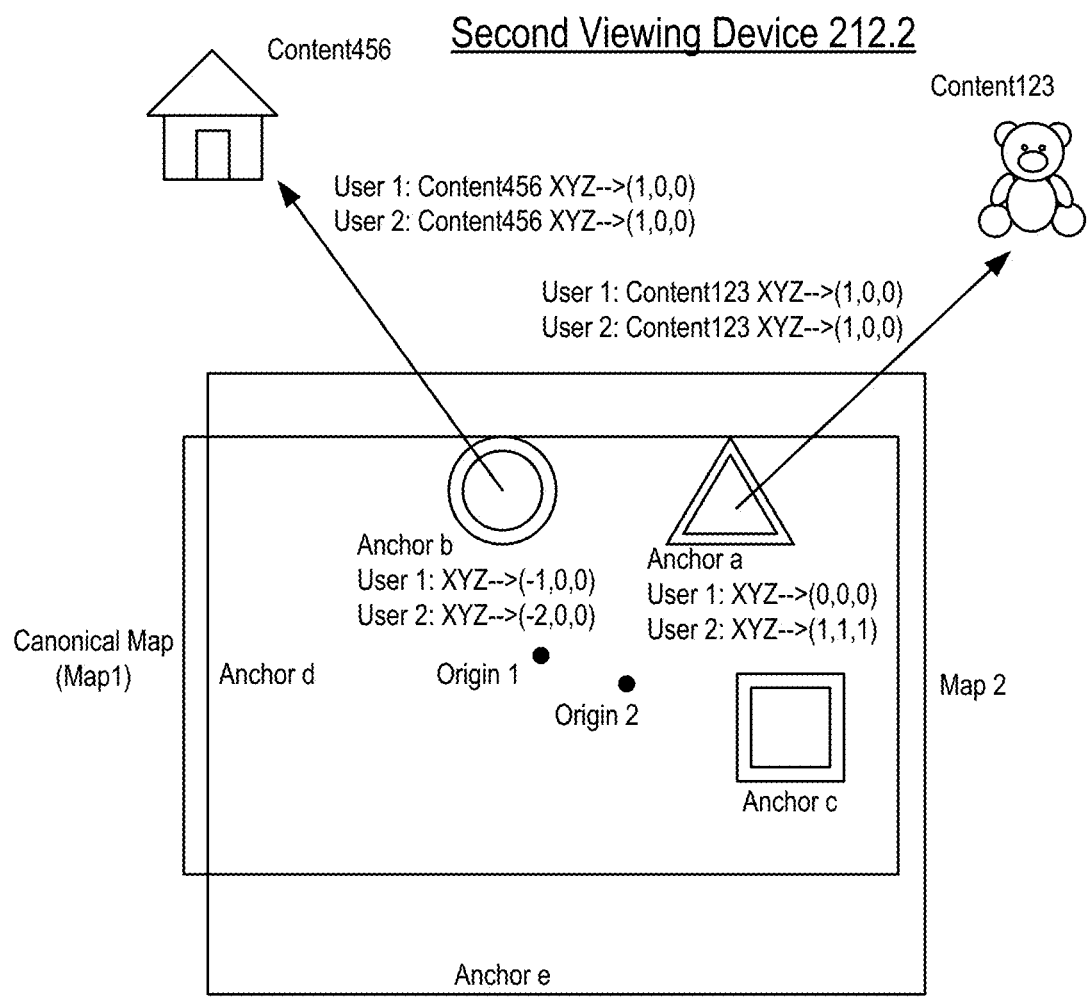
FIG. 24 is a view similar to FIG. 23 after an anchor or anchors from the canonical map are included into Map 2 to generate a canonical map.

As shown in FIG. 24, the second viewing device 212.2 expands Map 2 to include Anchor d in Map 1. The inclusion of Anchor d represents the beginning of an expansion of Map 2.

Figure 25:
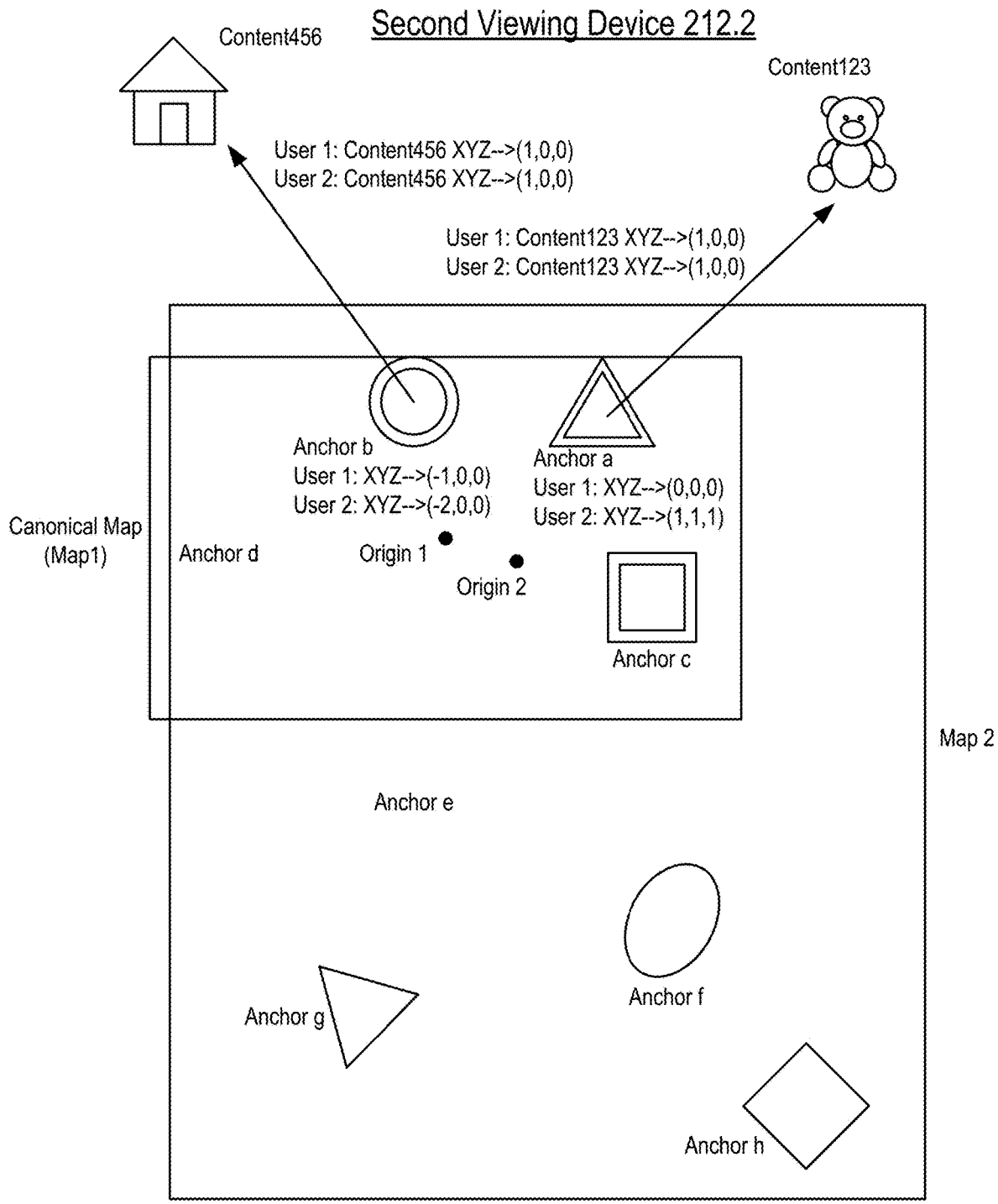
FIG. 25 is a view similar to FIG. 24 illustrating further expansion of Map 2 on the second viewing device.

As shown in FIG. 25, the second viewing device 212.2 continues to expand Map 2 as further anchors (Anchors f, g, and h) are identified by the second viewing device 212.2, for example as the user walks around the real world. It can also be noted that Map 1 has not expanded in FIGS. 24 and 25.

Figure 26:
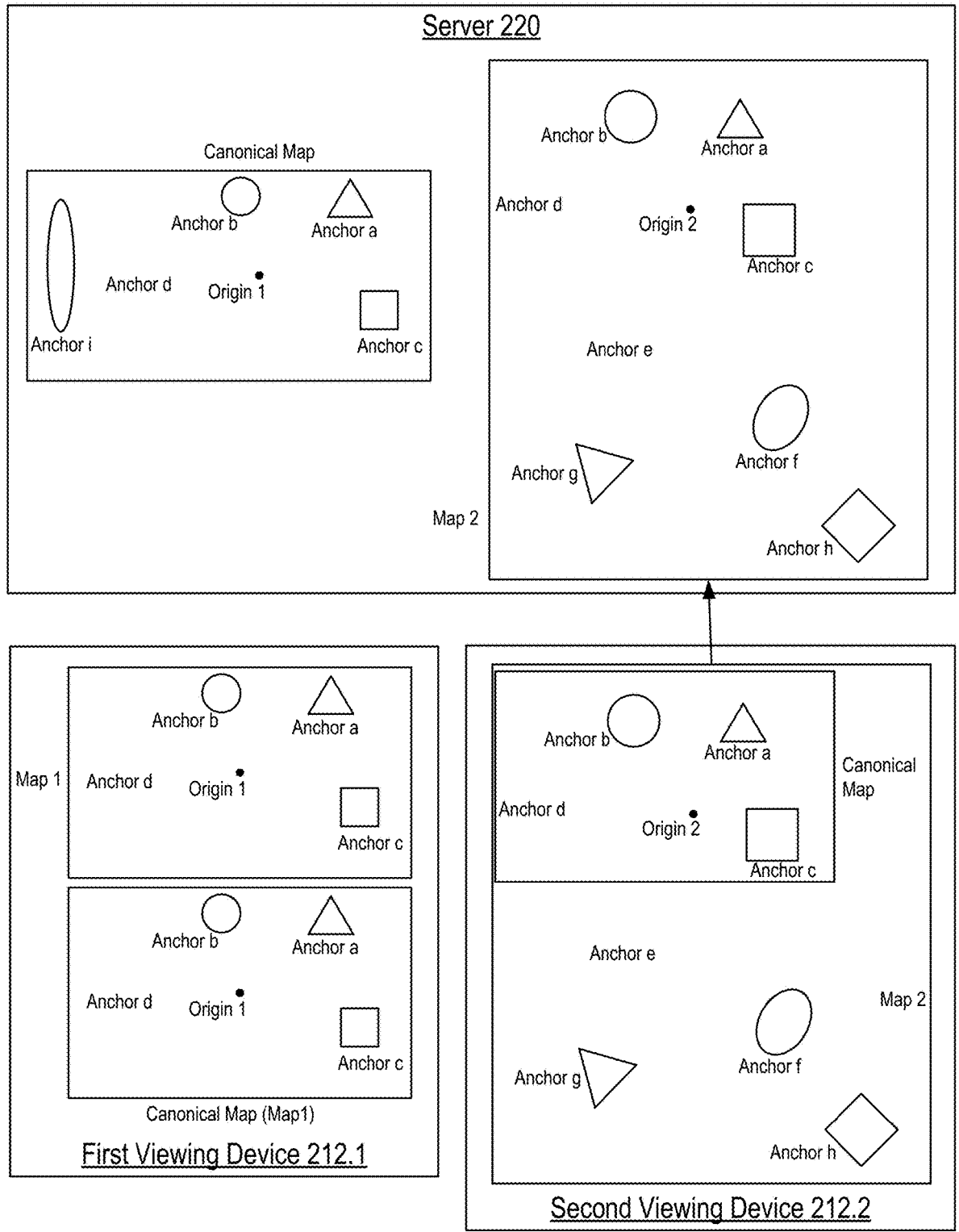
FIG. 26 is a similar view to FIG. 25 illustrating upload of Map 2 from the second viewing device to the server.

Referring to FIG. 26, the second viewing device 212.2 uploads Map 2 to the server 220. The server 220 stores Map 2 together with the canonical map.

The canonical map within the server 220 now includes anchor i which is not included in Map 1 on the first viewing device 212.1. The canonical map on the server 220 may have expanded to include anchor i when a third viewing device (not shown) uploaded a map to the server 220 and such a map included anchor i.

Figure 27:
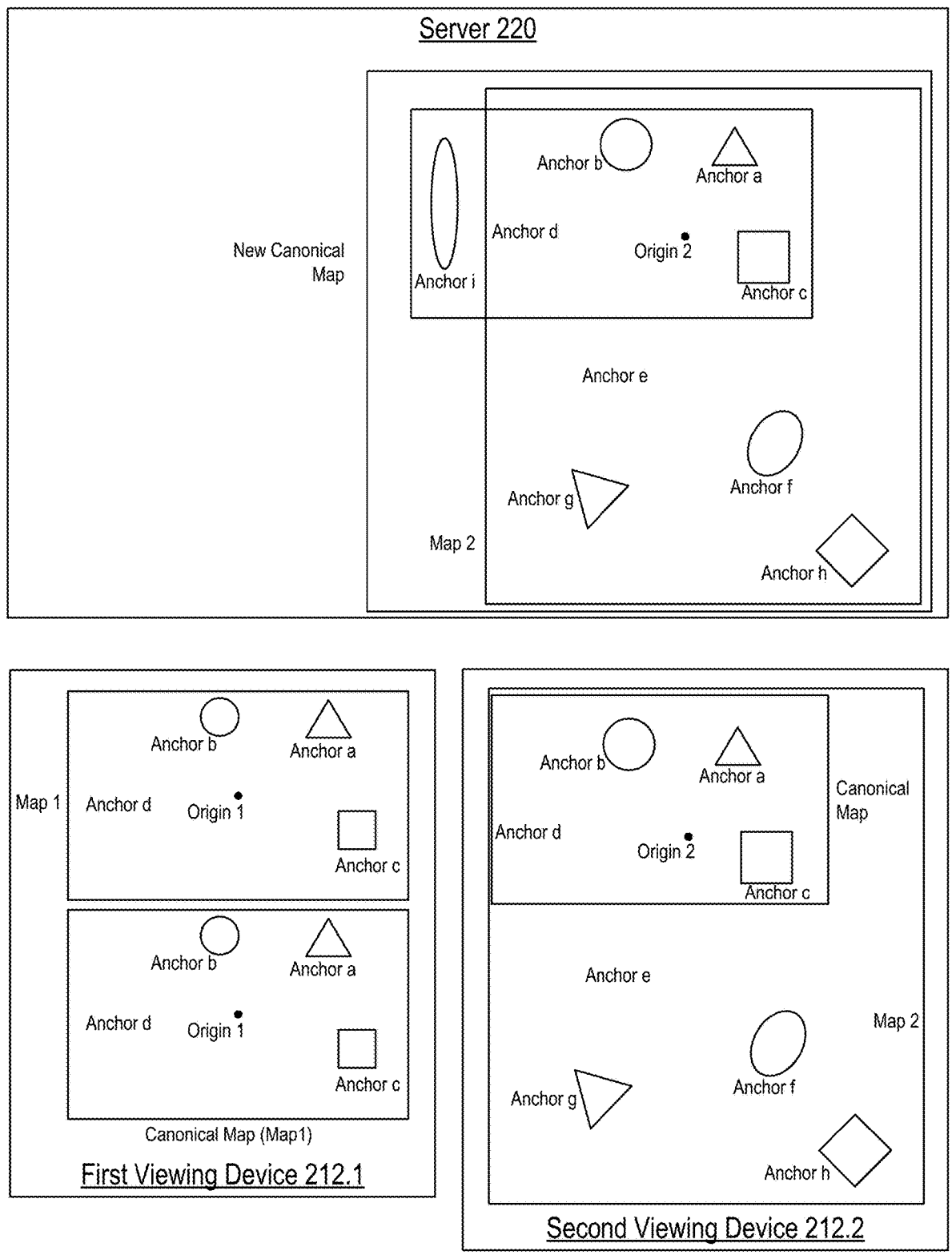
FIG. 27 is a view similar to FIG. 26 merging of Map 2 with the canonical map.

In FIG. 27, the server 220 merges Map 2 with the canonical map. The server 220 determines that anchors a to d are common to the canonical map and Map 2. The server 220 expands the canonical map to include anchors e to h from Map 2 form a new canonical map. The canonical maps on the first and second viewing devices 212.1 and 212.2 are based on Map 1 and are outdated.

Figure 28:
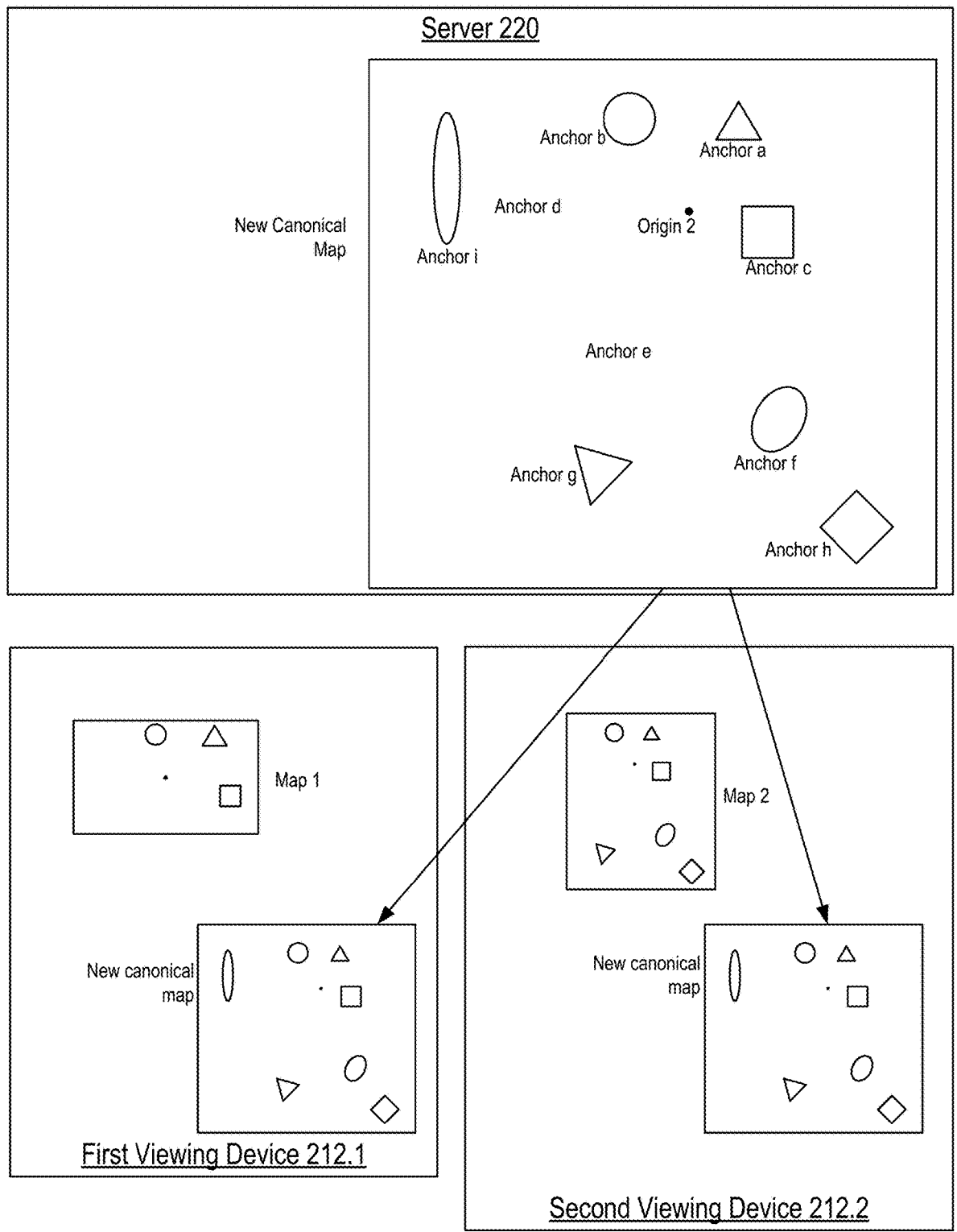
FIG. 28 is a view similar to FIG. 27 illustrating transmission of a new canonical map from the server to the first and second viewing devices.

In FIG. 28, the server 220 transmits the new canonical map to the first and second viewing devices 212.1 and 212.2. The first and second viewing devices 212.1 and 212.2 proceed as described above to localize their respective local maps (Map1 and Map 2 respectively) to the new canonical map.

Figure 29:
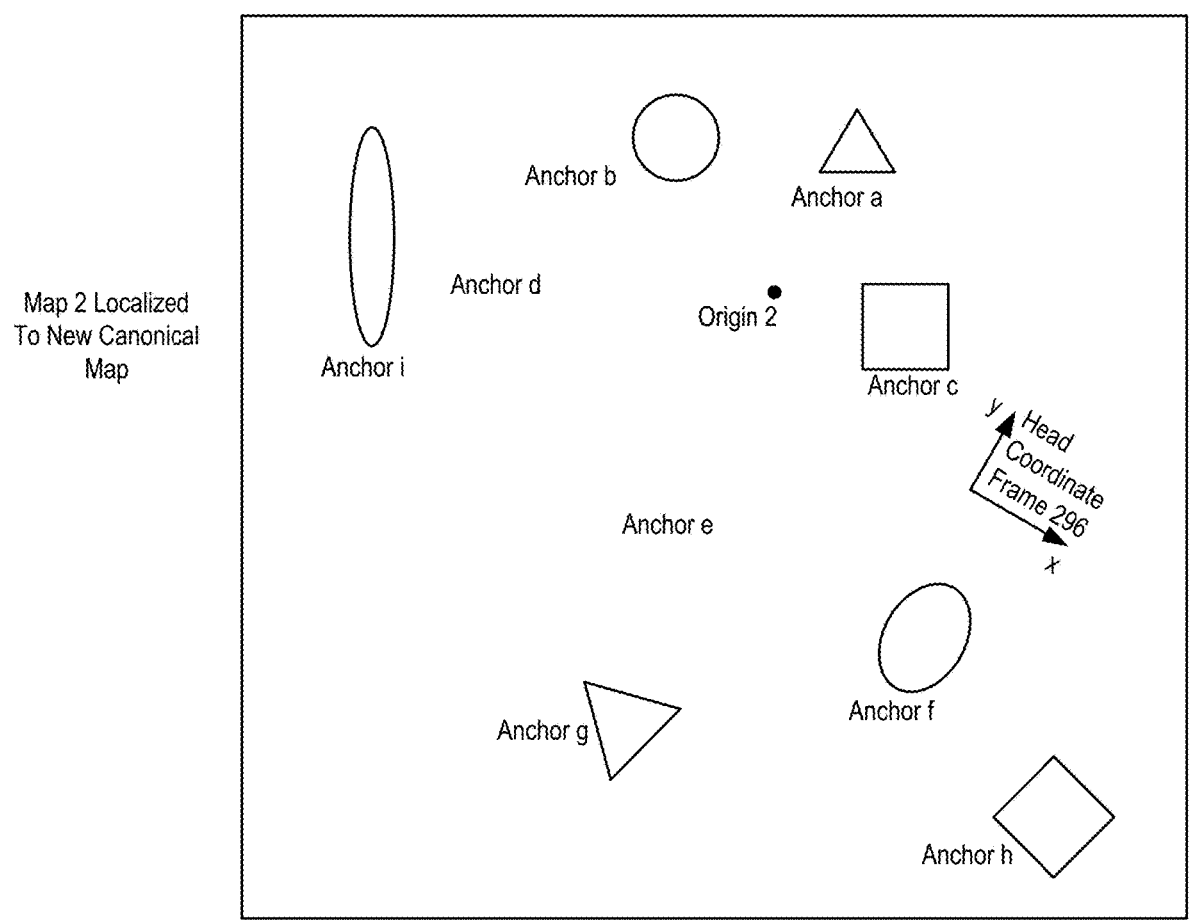
FIG. 29 is a two-dimensional representation of Map 2 and a head coordinate frame of the second viewing device that is referenced to Map 2.

As shown in FIG. 29, the head coordinate frame 296 or "head pose" is related to the anchors in Map 2. The anchors of Map 2 serve as a world coordinate frame and the transformation from the world coordinate frame to the head coordinate frame 296 has been previously discussed with reference to FIG. 22. The head coordinate frame 296 shown in FIG. 29 only has two orthogonal axes that are in a particular coordinate position relative to the anchors of Map 2, and at particular angles relative to Map 2. It should however be understood that the head coordinate frame 296 is in a three-dimensional location relative to the anchors of Map 2 and has three orthogonal axes within three-dimensional space.

Figure 30:
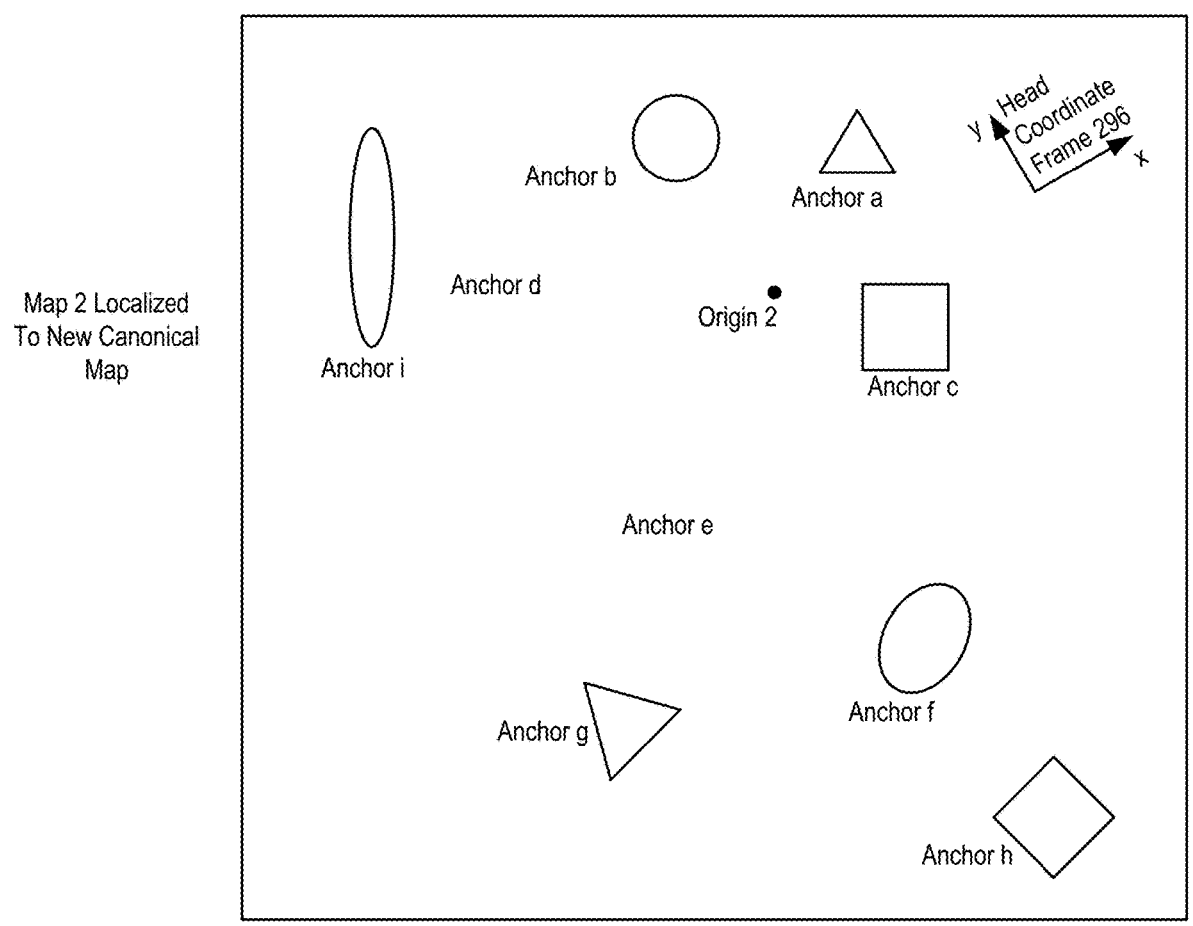
FIG. 30 is a view similar to FIG. 29 illustrating, in two-dimensions, adjustment of the head coordinate frame which can occur in six degrees of freedom.

In FIG. 30, the head coordinate frame 296 has moved relative to the anchors of Map 2. The head coordinate frame 296 has moved because the second user 214.2 has moved their head. The user can move their head in six degrees of freedom (6dof). The head coordinate frame 296 can thus moves in 6dof, namely in three-dimensions from its original location in FIG. 29 and about three orthogonal axes relative to the anchors of Map 2. The head coordinate frame 296 is adjusted when the real object detection camera 244 and inertial measurement unit 248 in FIG. 12 respectively detect real objects and motion of the head unit 222.

Figure 31:
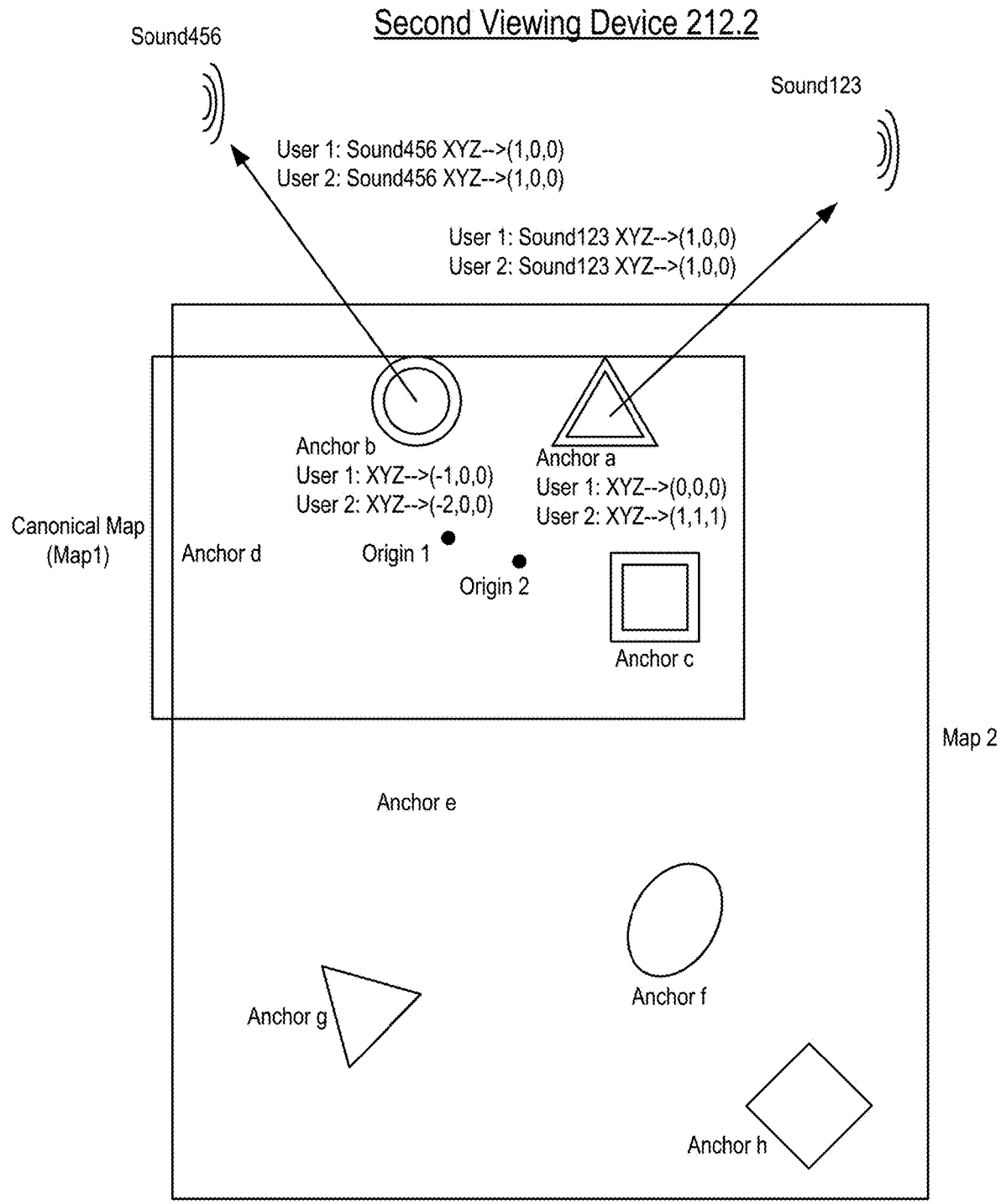
FIG. 31 illustrates a canonical map on the second viewing device wherein sound is localized relative to anchors of Map 2.

FIG. 31 shows that sound may be associated with one or more anchors. A user may, for example, wear headphones or earphones with stereoscopic sound. The location of sound through headphones can be simulated using conventional techniques. The location of sound may be located in a stationary position so that, when the user rotates their head to the left, the location of sound rotates to the right so that the user perceives the sound coming from the same location in the real world. In the present example, location of sound is represented by Sound123 and Sound456. For purposes of discussion, FIG. 31 is similar to FIG. 25 in its analysis. When the first and second users 214.1 and 214.2 are located in the same room at the same or different times, they perceive Sound123 and Sound456 coming from the same locations within the real world.

Figure 32:
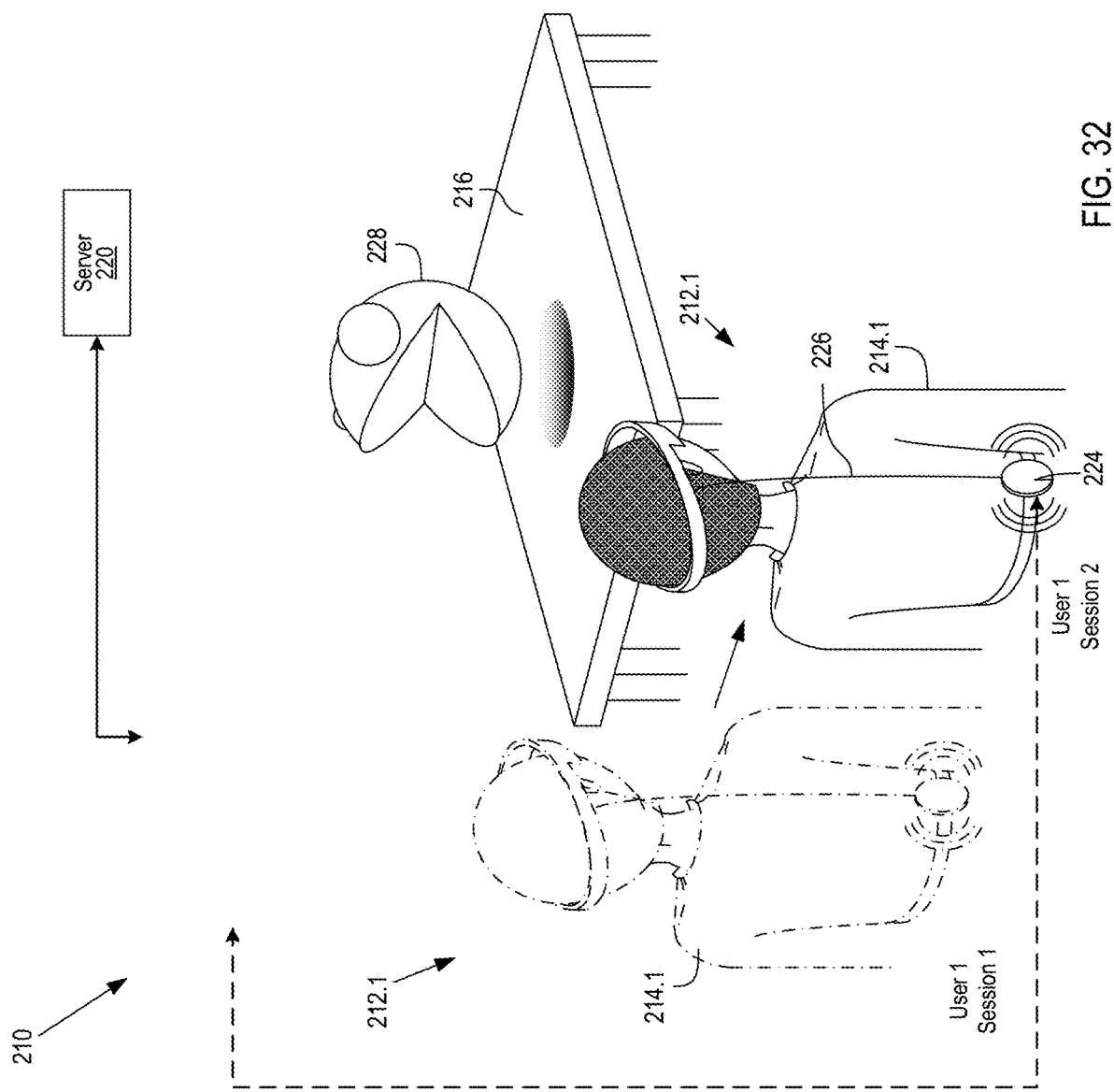
FIGS. 32 and 33 are a perspective view and a block diagram illustrating use of the viewing system according to another embodiment wherein the first user has terminated a first session and the first user has initiated a second session using the viewing system.
Figure 33:
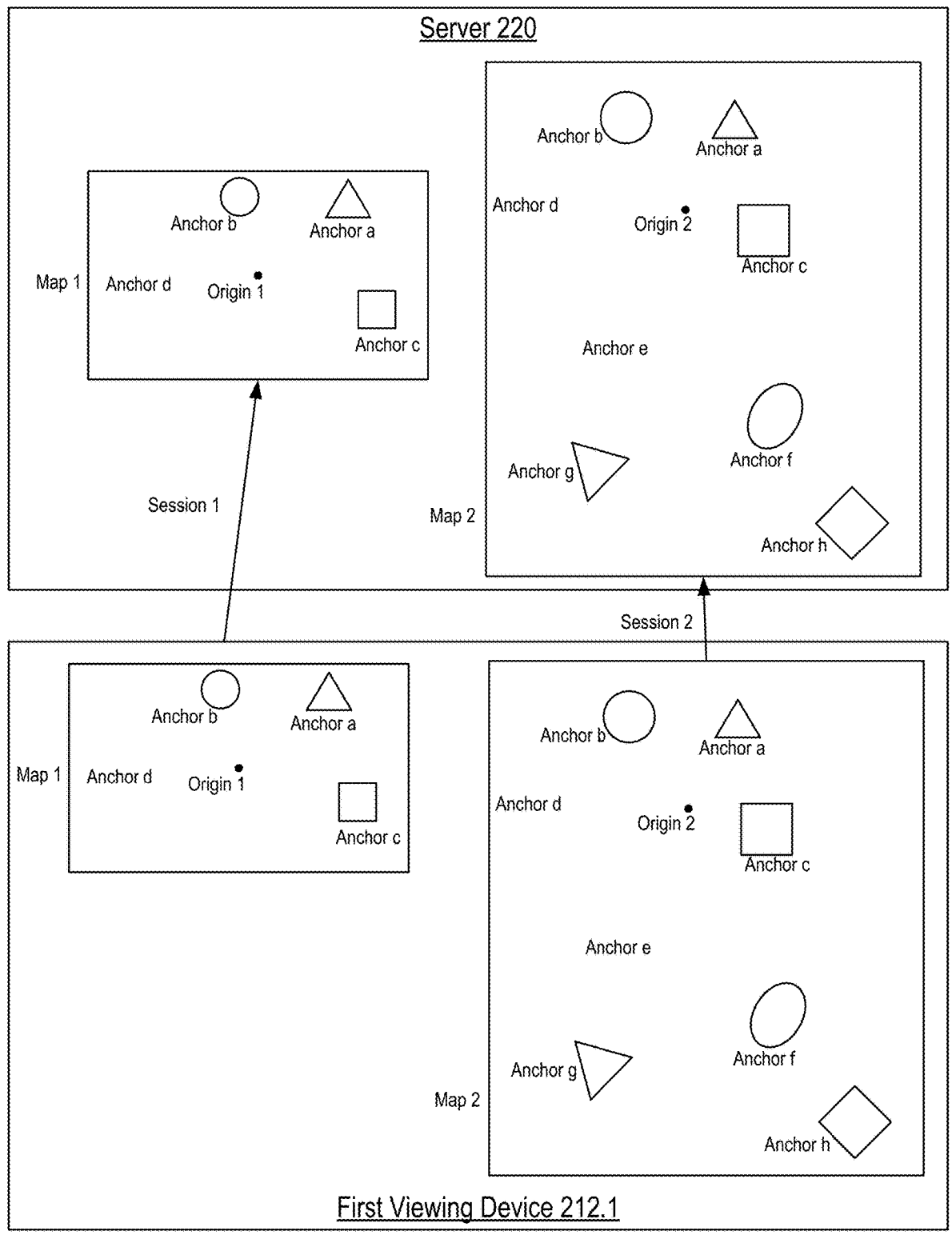

FIGS. 32 and 33 illustrates a further implementation of the technology described above. The first user 214.1 has initiated a first session as described with reference to FIG. 11. As shown in FIG. 32, the first user 214.1 has terminated the first session as indicated by the phantom lines. At the end of the first session, the first viewing device 212.1 uploaded Map 1 to the server 220. The first user 214.1 has now initiated a second session at a later time than the first session. The first viewing device 212.1 does not download Map 1 from the server 220 because Map 1 is already stored on the first viewing device 212.1. If Map 1 is lost, then the first viewing device 212.1 downloads Map 1 from the server 220. The first viewing device 212.1 then proceeds to build anchors for Map 2, localizes to Map 1 and further develops a canonical map as described above. Map 2 is then used for relating local content, a head coordinate frame, local sound, etc. as described above.

Figure 34:
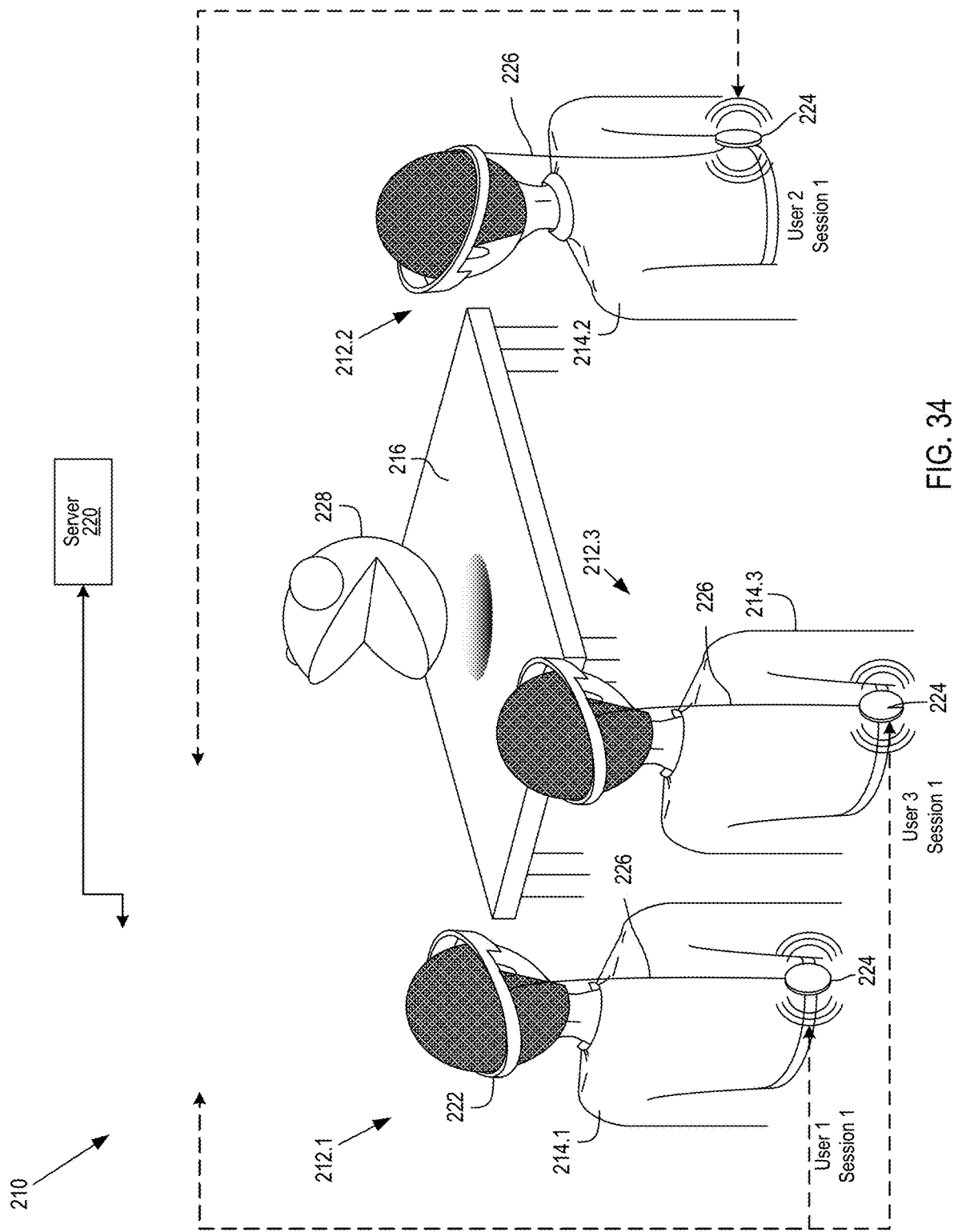
FIGS. 34 and 35 are a perspective view and a block diagram illustrating use of the viewing system according to a further embodiment of the invention wherein three users are simultaneously using the viewing system in the same session.
Figure 35:
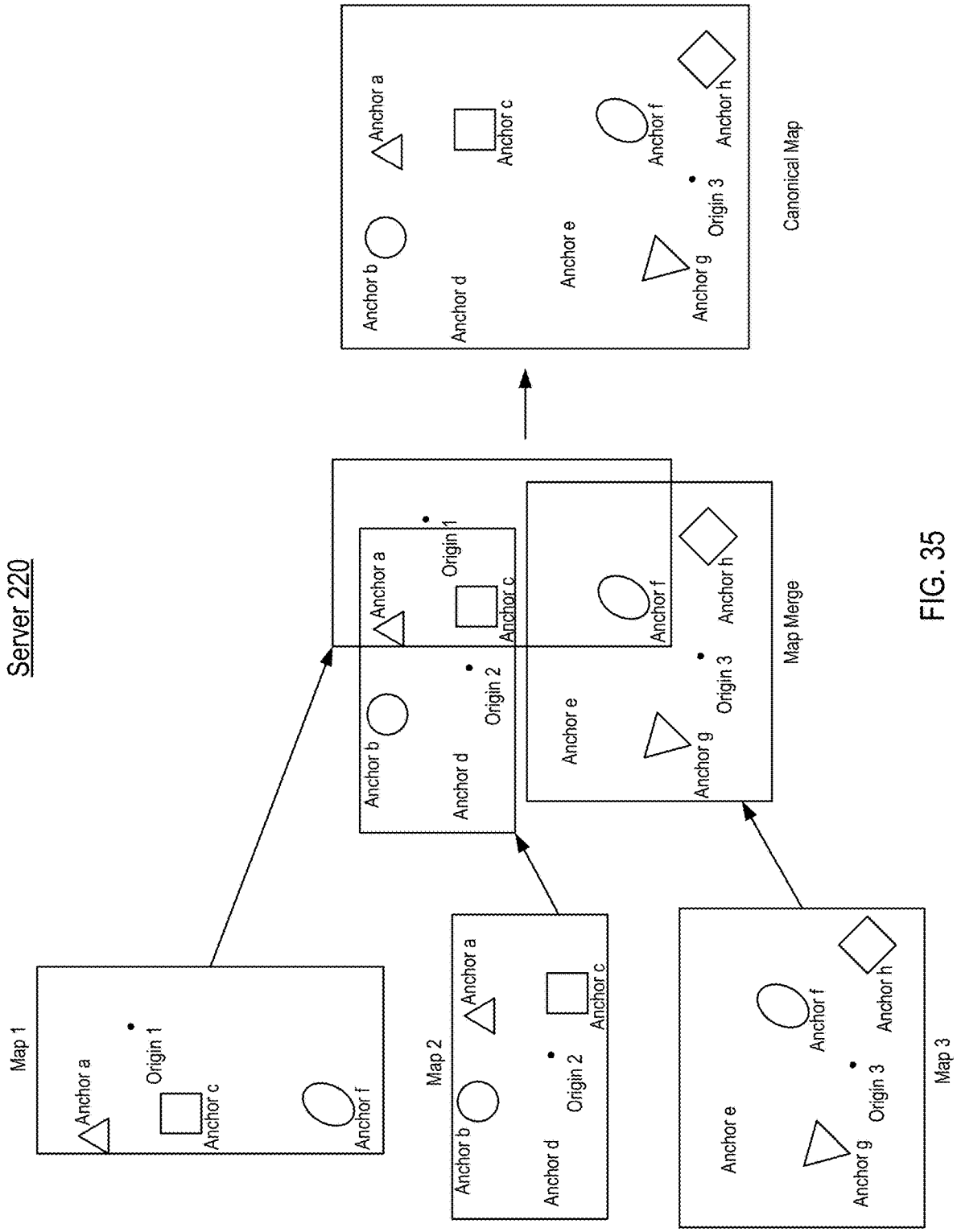

Referring to FIGS. 34 and 35, it may also be possible that more than one user interacts with the server 220 in the same session. Multiple users in the same location have the additional benefit that it leads to more accurate anchors relative to a head coordinate frame. Multiple systems tend to detect more anchors and more anchors lead to more cross-checking and better scoring of maps. In the present example, the first user 214.1 and the second user 214.2 are joined by a third user 214.3 with a third viewing device 212.3. Each viewing device 212.1, 212.2 and 212.3 begins to generate its own map, namely Map 1, Map 2 and Map 3, respectively. As the viewing devices 212.1, 212.2 and 212.3 continue to develop Maps 1, 2 and 3, the maps are incrementally uploaded to the server 220. The server 220 merges Maps 1, 2 and 3 to form a canonical map. The canonical map is then transmitted from the server 220 to each one of the viewing devices 212.1, 212.2 and 212.3.

Figure 36:
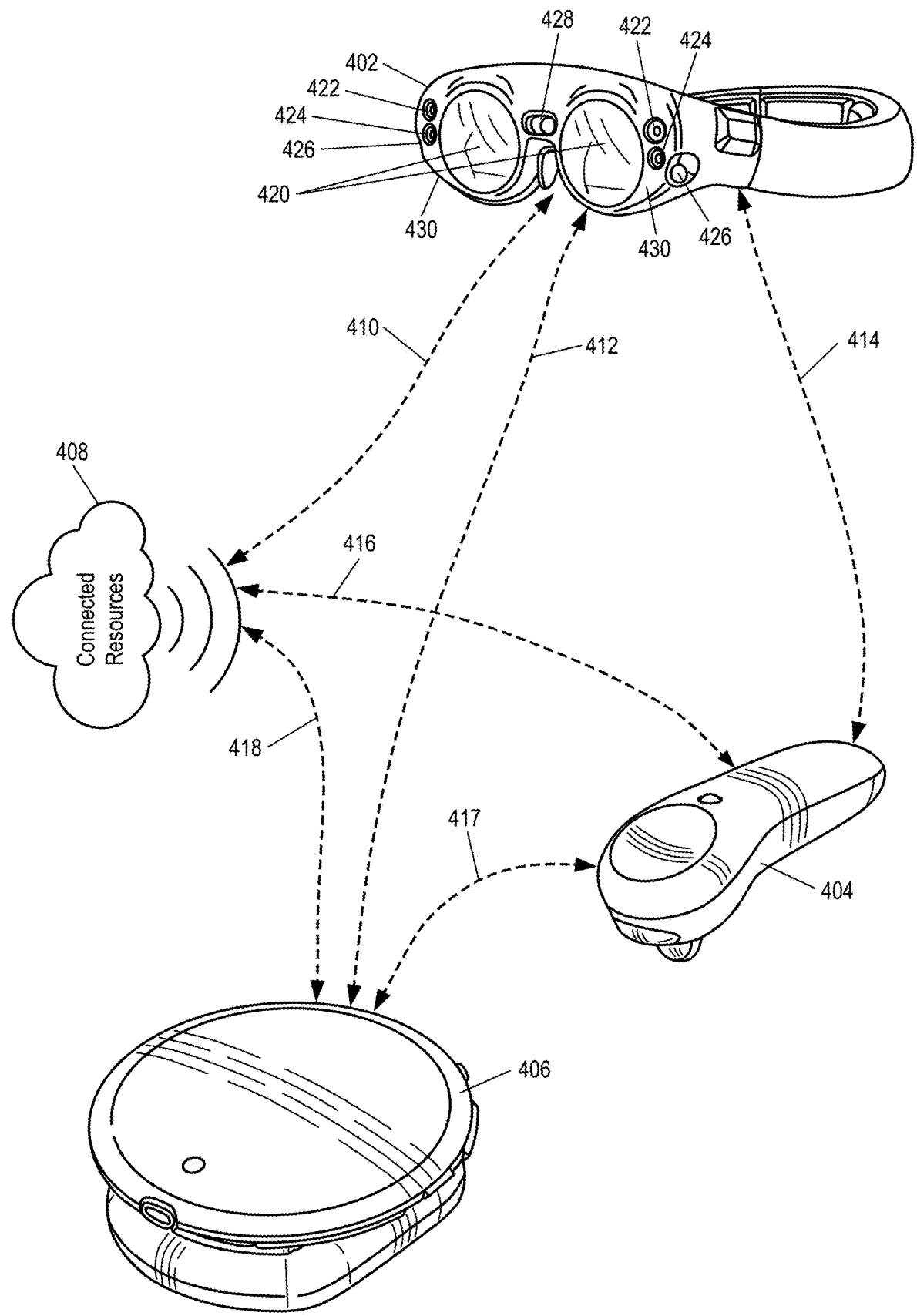
FIG. 36 is a perspective view of a viewing system that may be used by various users within a surgical environment.

Referring to FIG. 36, a viewing system is illustrated featuring a head unit 402, a handheld controller component 404, and an interconnected auxiliary computing or controller component 406 which may be configured to be worn as a belt pack or the like on the user. Each of these components may be operatively coupled 410, 412, 414, 416, 417, 418 to each other and to other connected resources 408 such as cloud computing or cloud storage resources via wired or wireless communication configurations, such as those specified by IEEE 802.11, Bluetooth®, and other connectivity standards and configurations. As described, for example, in U.S. patent application Ser. Nos. 14/555,585, 14/690,401, 14/331,218, 15/481,255, 62/627,155, 62/518,539, 16/229,532, 16/155,564, 15/413,284, 16/020,541, 62/702,322, 62/206,765, 15/597,694, 16/221,065, 15/968,673, 62/682,788, and 62/899,678 each of which is incorporated by reference herein in its entirety, various aspects of such components are described, such as various embodiments of the two depicted optical elements 420 through which the user may see the world around them along with visual components which may be produced by the associated system components, for an augmented reality experience. Such a system may also comprise various sensors configured to provide information pertaining to the environment around the user, including but not limited to various camera type sensors (such as monochrome, color/RGB, and/or thermal imaging components) 422, 424, 426, depth camera sensors 428, and/or sound sensors 430 such as microphones.

Figure 37:
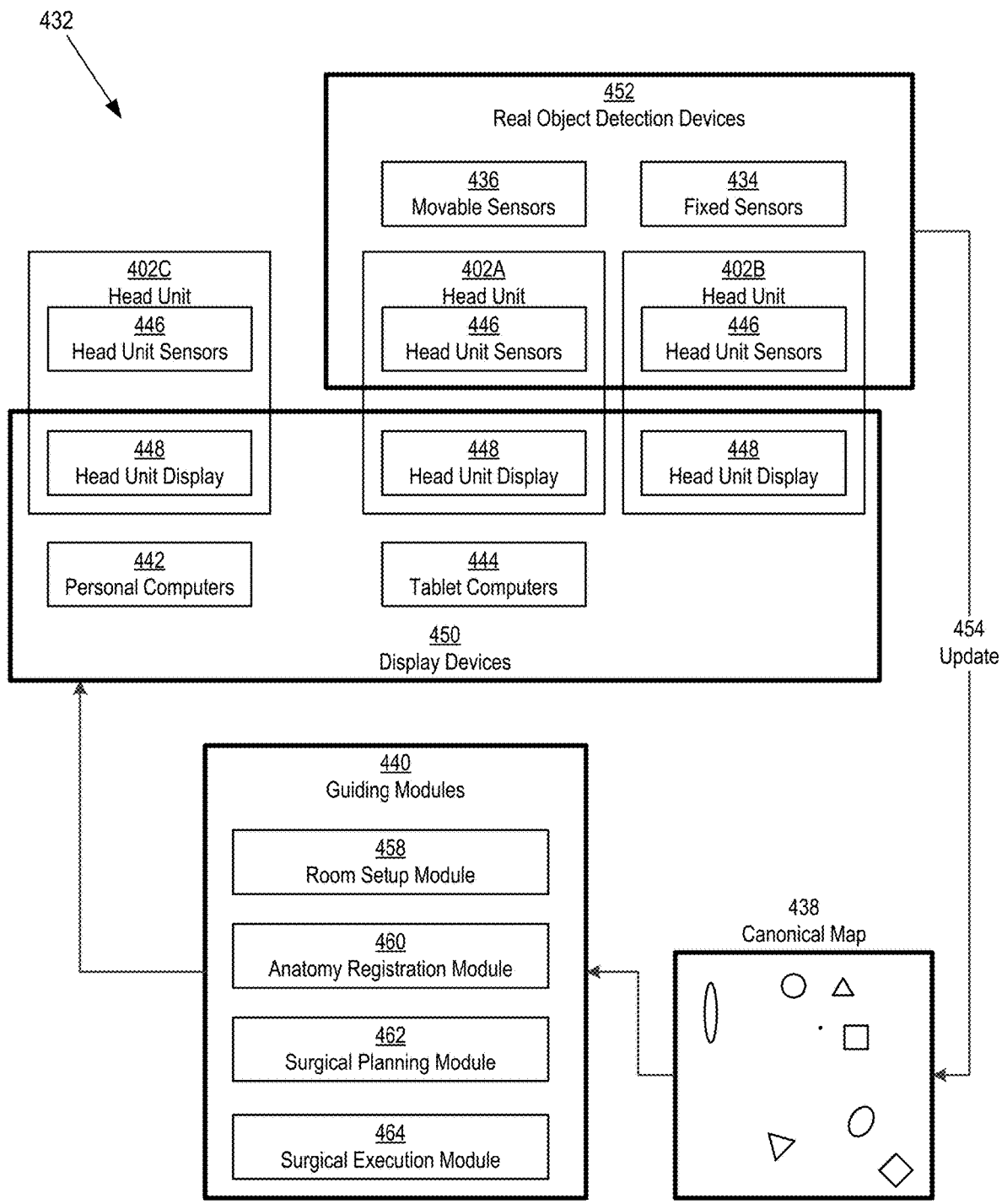
FIG. 37 is a block diagram of a more encompassing viewing system that includes multiple head units, sensors, guiding modules and computers.

FIG. 37 illustrates a more encompassing viewing system 432 that includes a head unit 402A, a head unit 402B, a head unit 402C, fixed sensors 434, movable sensors 436, a canonical map 438, guiding modules 440, personal computers 442, and tablet computers 444.

Each one of the head units 402A, 402B and 402C includes a respective set of head unit sensors 446 and a respective head unit display 448. The head units 402A and 402B may be located in the same room and the head unit 402C may be located in a different room that is remotely located from the room in which the head units 402A and 402B are located. The head unit displays 448, personal computers 442, and table computers 444 represent different display devices 450 through which users may view two-dimensional or three-dimensional images as described with reference to FIG. 34 above. The head unit sensors 446 may be used to detect a head frame of each one of the head units 402A, 402B or 402C as described above. In addition, the head unit sensors 446 of the head units 402A and 402B may be used to detect objects within the room in which they are located. These sensors are particularly useful for sensing objects that the user is looking at. For example, if the user of the head unit 402A is looking at a body part of a patient, the head unit sensor 446 of the head unit 402A also detects the body part of the patient.

The fixed sensors 434 are sensors that are mounted in fixed locations in the room. The fixed sensors 434 may be used to detect stationary objects within the room or, more commonly, objects that move within the room, such as surgical personnel, a robot, a cutting tool on the robot, a surgical implant, surgical tools, disposable items, a patient, and a body part of a patient. The movable sensors 436 represent sensors that may be located on movable objects such as robots that move within the room. The fixed sensors 434, movable sensors 436 and head unit sensors 446 of the head units 402A and 402B represent real object detection devices 452. At 454, the real object detection devices 452 serve to continually update the canonical map 438 at described above, especially with reference to FIG. 35.

The guiding modules 440 include a room setup module 458, an anatomy registration module 460, a surgical planning module 462, and a surgical execution module 464. The canonical map 438 serves as a digital representation (also sometimes referred to as a "digital twin") of real objects in a real environment as detected by the real object detection devices 452. The guiding modules 440 are connected to the data store holding the canonical map 438 and can retrieve the canonical map 438. Each one of the guiding modules 440 is executable to guide at least one of a virtual object and a real object based on the digital representation. The guiding modules 440 may also provide an output to the display devices 450. Because the real object detection devices 452 continuously detect the real objects, the canonical map 438 is continually updated. The guiding modules 440 continually modify their guiding and visual output in response to changes in the canonical map 438. The guiding modules 440 typically reside on a data store of a server computer system and are executed by a processor of the server computer system. Portions or all of the guiding modules 440 may also be executed by other computer systems such as any one of the head units 402A to 402C.

Figure 38:
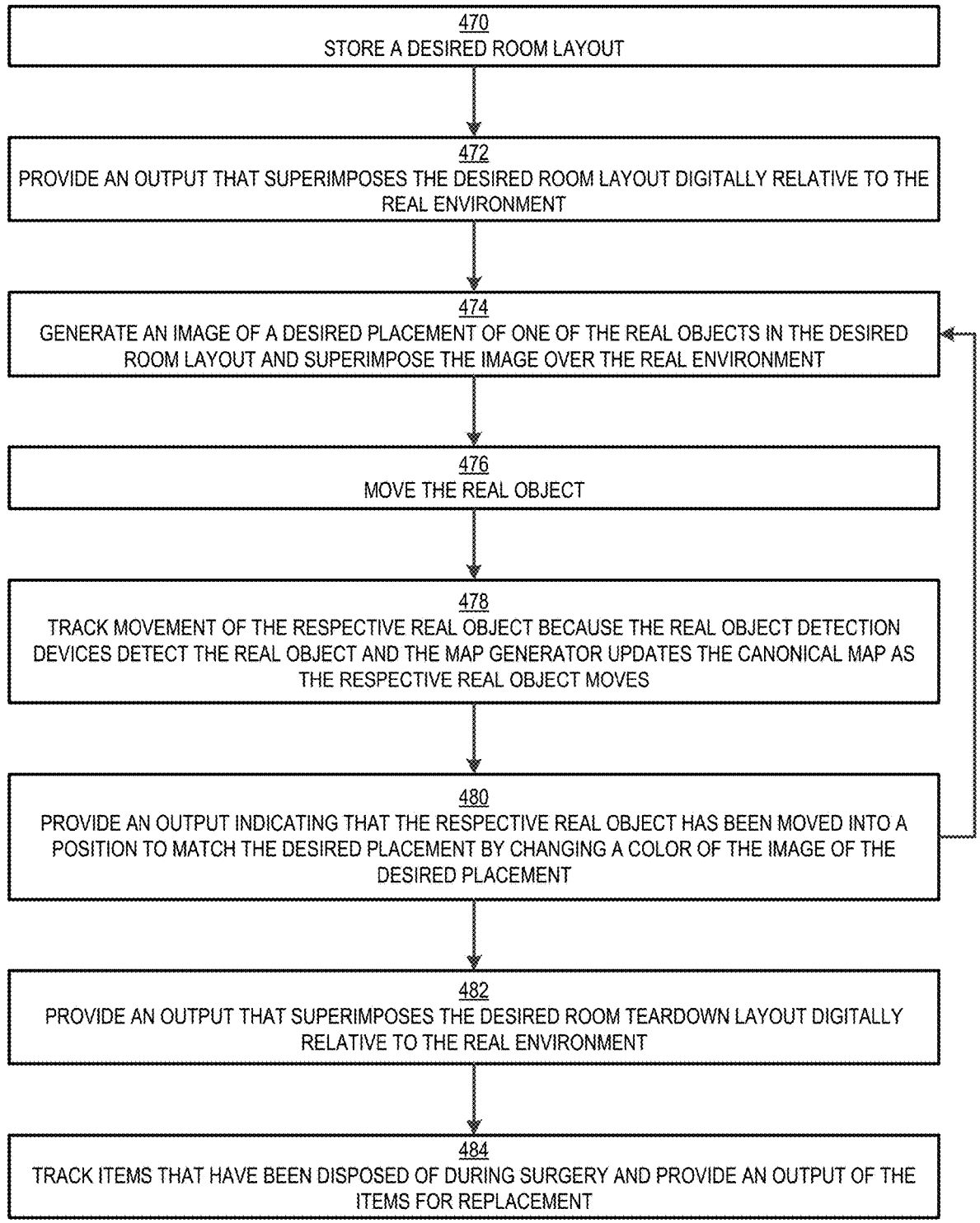
FIG. 38 is a flow chart illustrating functioning of a room setup module.

FIG. 38 illustrates the functioning of the room setup module 458 in FIG. 37. At 470, the processor of the server computer system stores a desired room layout. The desired room layout is typically configured by an operator and is dependent on the particular proportions of the room and a particular surgery for which the room is intended.

At 472, the processor provides an output that superimposes the desired room layout digitally relative to the real environment. The canonical map 438 is used to determine the existing real environment. An operator overlays the desired room layout relative to the canonical map 438.

At 474, an image is generated of a desired placement of one of the real objects in the desired room layout and the image is superimposed over the real environment. At 476, an operator moves the real object within the real environment. The operator moves the real object in a direction towards the image of the desired placement of the real object.

At 478, the movement of the respective real object is tracked. The real object is tracked because the real object detection devices 452 detect the real object and because a map generator, for example the map merge algorithm 324 in FIG. 16, updates the canonical map 438 as the respective real object moves.

At 480, the system provides an output indicating that the respective real object has been moved into a position to match the desired placement. The output may, for example, be a changing of a color of the image of the desired placement. The operator may repeat steps 474 to 480 to move further real objects to continue to match the real objects to the desired room layout. The room may then be used to execute a surgery on a patient.

Following the surgery of the patient, a user may again use the system to tear down the room. At 482, the system provides an output that superimposes the desired room tear down layout digitally relative to the real environment. The operator may then move the real objects in a reverse order. Element 484 represents that the system tracks items that have been disposed of during surgery and provides an output of items for replacement. By way of example, if the desired room outlet requires 100 cotton balls and 30 cotton balls were used during the surgery, the system provides an output indicating that 30 cotton balls should be replaced.

Figure 39:
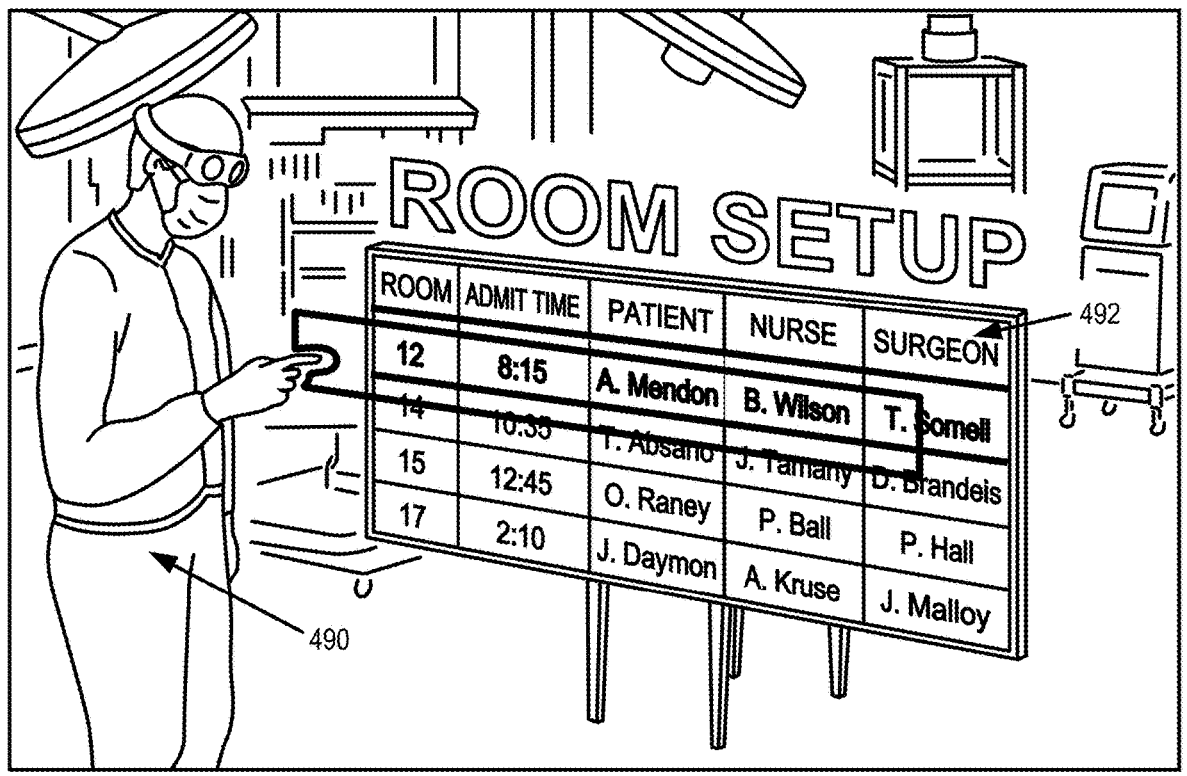
FIGS. 39 and 40 are perspective views of a room and users that are tasked to set the room up for surgery using the viewing system.

FIG. 39 illustrates a user 490 who is asked to set a room up for surgery. The user 490, wearing a head unit such as the head unit 402A is presented with a display of a room setup menu 492. The user 490 selects items from the menu 492 using their hand or the handheld controller component 404.

Figure 40:
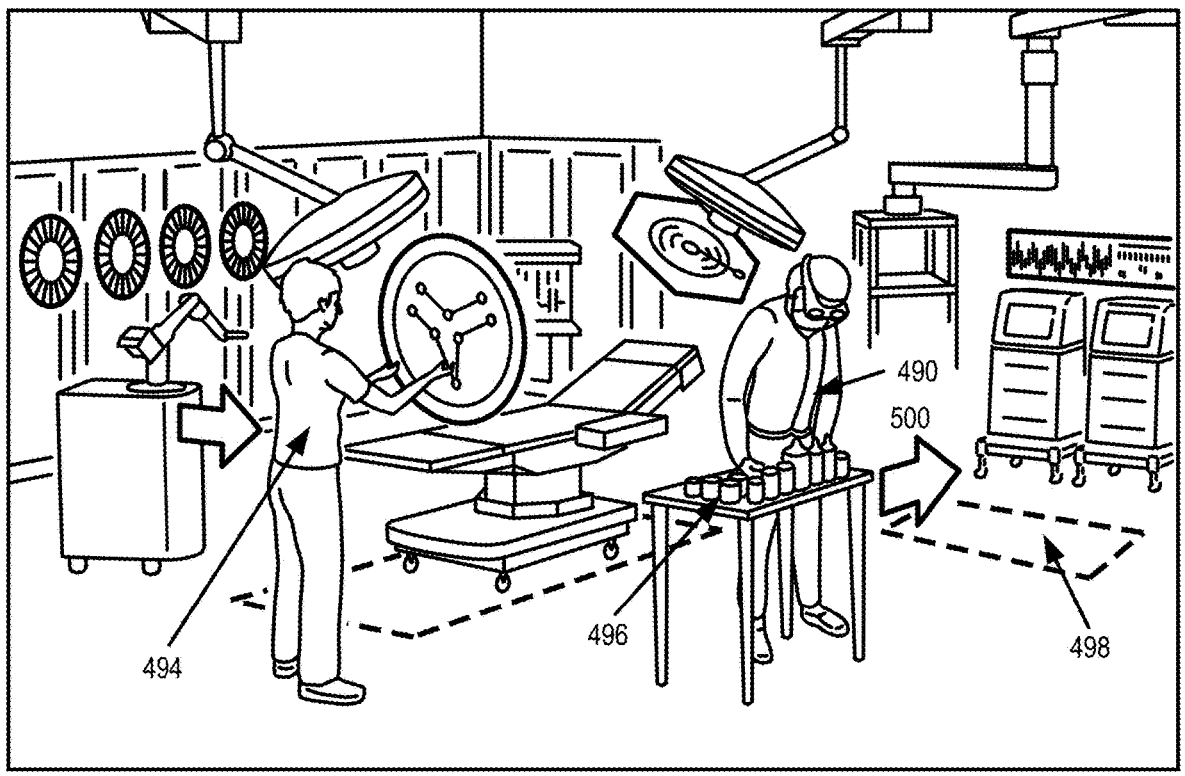

FIG. 40 illustrates the user 490 and a remote user 494. The remote user 494 is tasked to design and store the room layout using one of the personal computers 442. The fixed sensors 434 have detected a number of real objects within the room, for example a table 496. An image of a virtual object 498 is displayed to the user 490 and represents a desired location for the table 496. The user 490 then moves the table 496 in a direction 500. Movement of the table 496 in the direction 500 is tracked by the fixed sensors 434, head unit sensors 446 and potentially also a movable sensor 436 mounted to the table 496. The image 498 is originally in one color, for example red, and changes to another color, for example green, when the table 496 is located over the image 498. The user 490 then repeats the process with other objects until all the objects are located in their desired locations. When the surgery has been completed, the user 490 is presented with a tear down map which the user 490 can use to return all the objects to their original positions.

Figure 41:
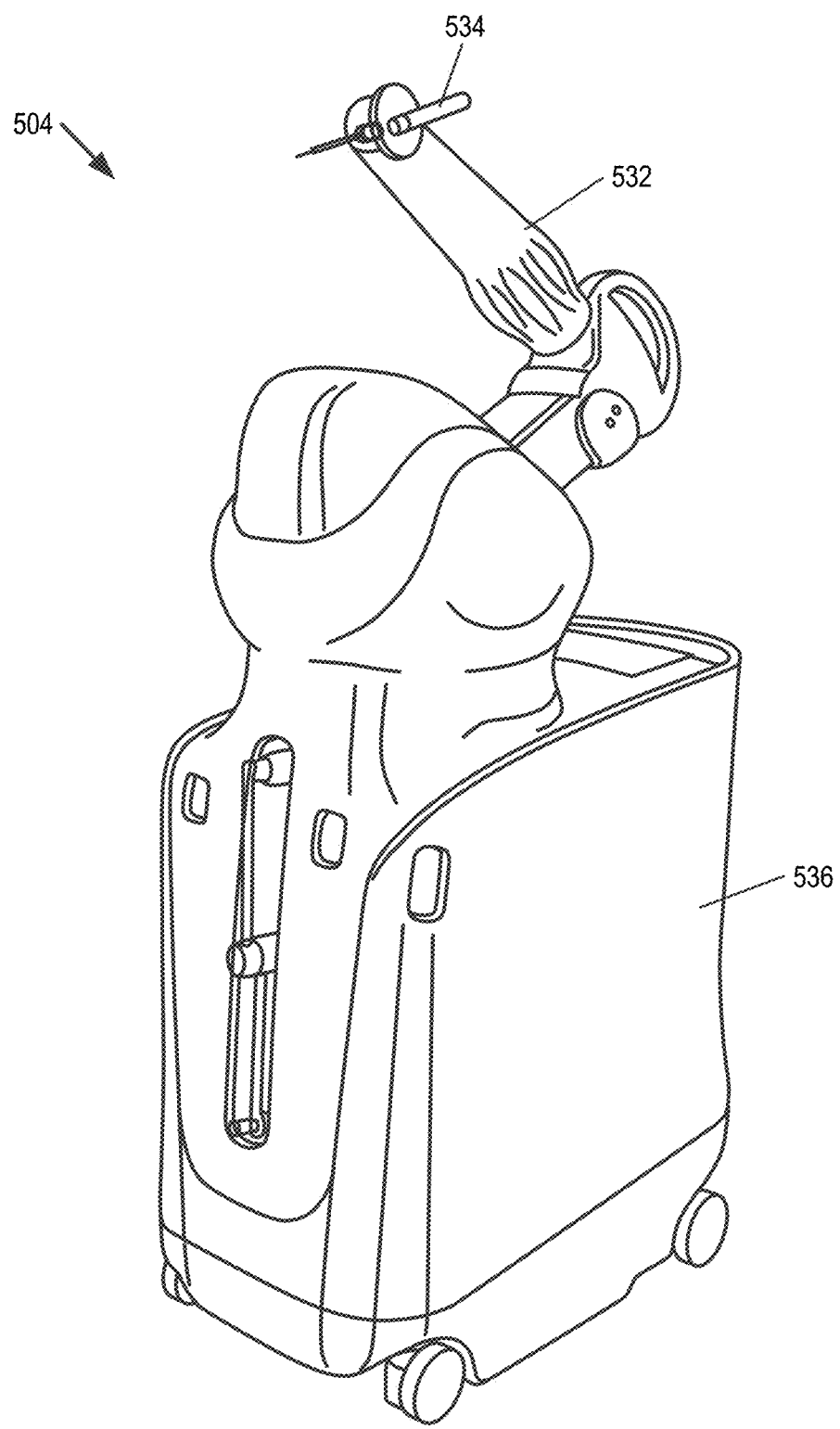
FIG. 41 is a perspective view of a surgical robot system.

FIG. 41 shows a surgical robot system 504 that is one of the real object that are located by the user 490. The surgical robot system 504 includes a surgical instrument 534, a movable arm 532, and a movable base 536. Such systems are available from vendors such as Stryker®, Intuitive Surgical®, and Johnson & Johnson®, and may be utilized for a variety of surgical procedures once "registered" to the anatomy of the patient so that a detailed and precise geometric relationship between portions of the surgical robot system, such as the surgical instrument 534, and the anatomy of the patient, are known to facilitate precise coordination of these relative to each other in three dimensional space. In other words, in an orthopedic surgery wherein one desires to cut a portion of a patient's bone with a bone cutting surgical instrument, of course it is important to precisely understand where in space the bone is relative to the instrument. In various embodiments, it is useful for surgical operators to wear systems such as that illustrated in FIG. 36, so that they may not only visualize the operating room around them, but also visualize virtual elements, such as preoperative images, intraoperative images, alternative views of various items, and understand geometric relationships of various objects, such as by the use of a common coordinate system (or "persistent coordinate frame", or "PCF") which may be established and utilized by one or more spatial computing users, and to which certain anatomy of the user and also certain aspects of a surgical instrument or system may also be registered. With the views of the one or more users registered to the PCF along with the surgical instruments and anatomy, virtual elements may be presented to users to assist in not only planning, but execution of surgical procedures.

Figure 42:
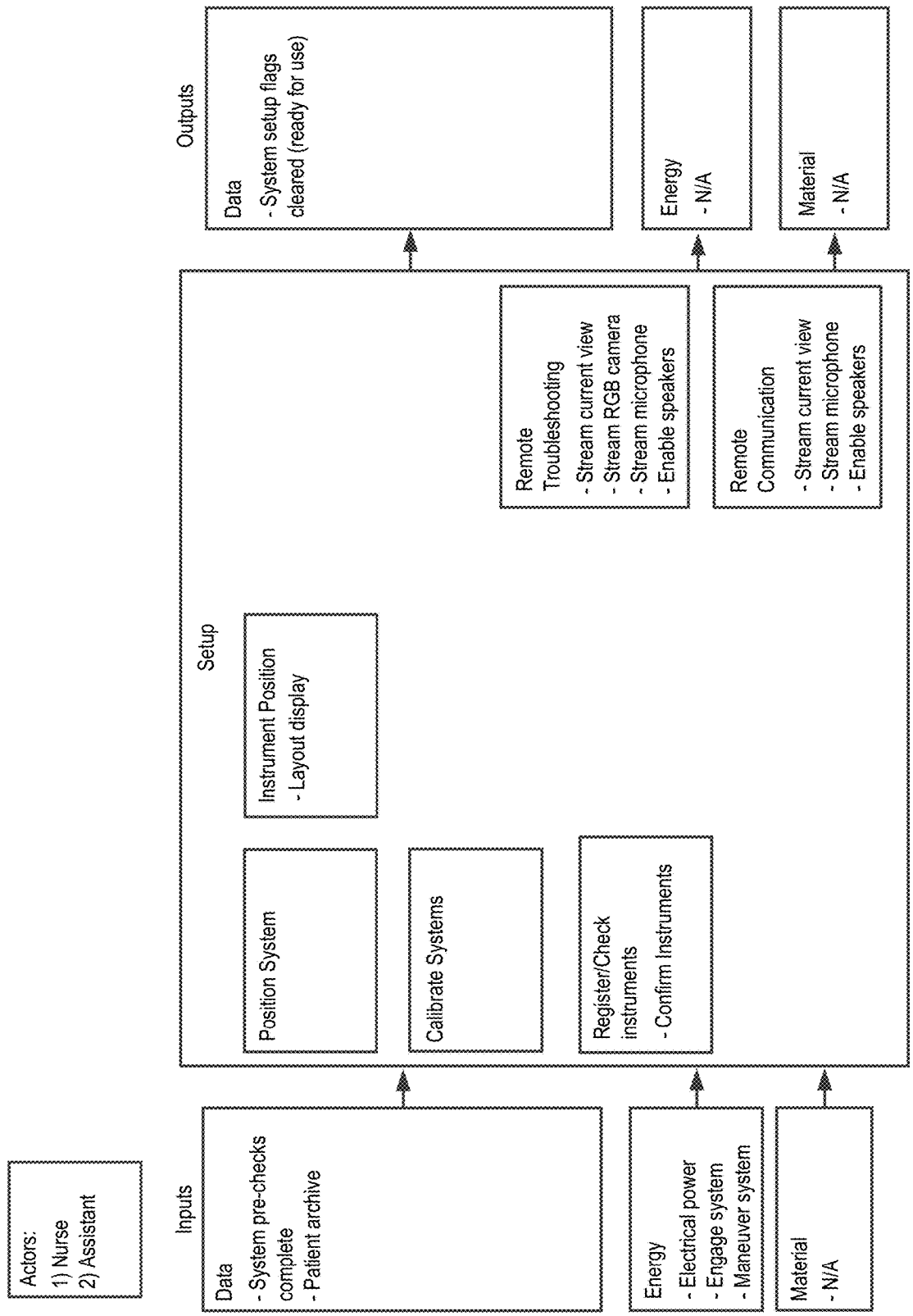
FIG. 42 is block diagram that illustrates various aspects of the room setup module.

FIG. 42 illustrates various aspects of the room setup module 458, including data input, data output, various actors, etc.

Figure 43:
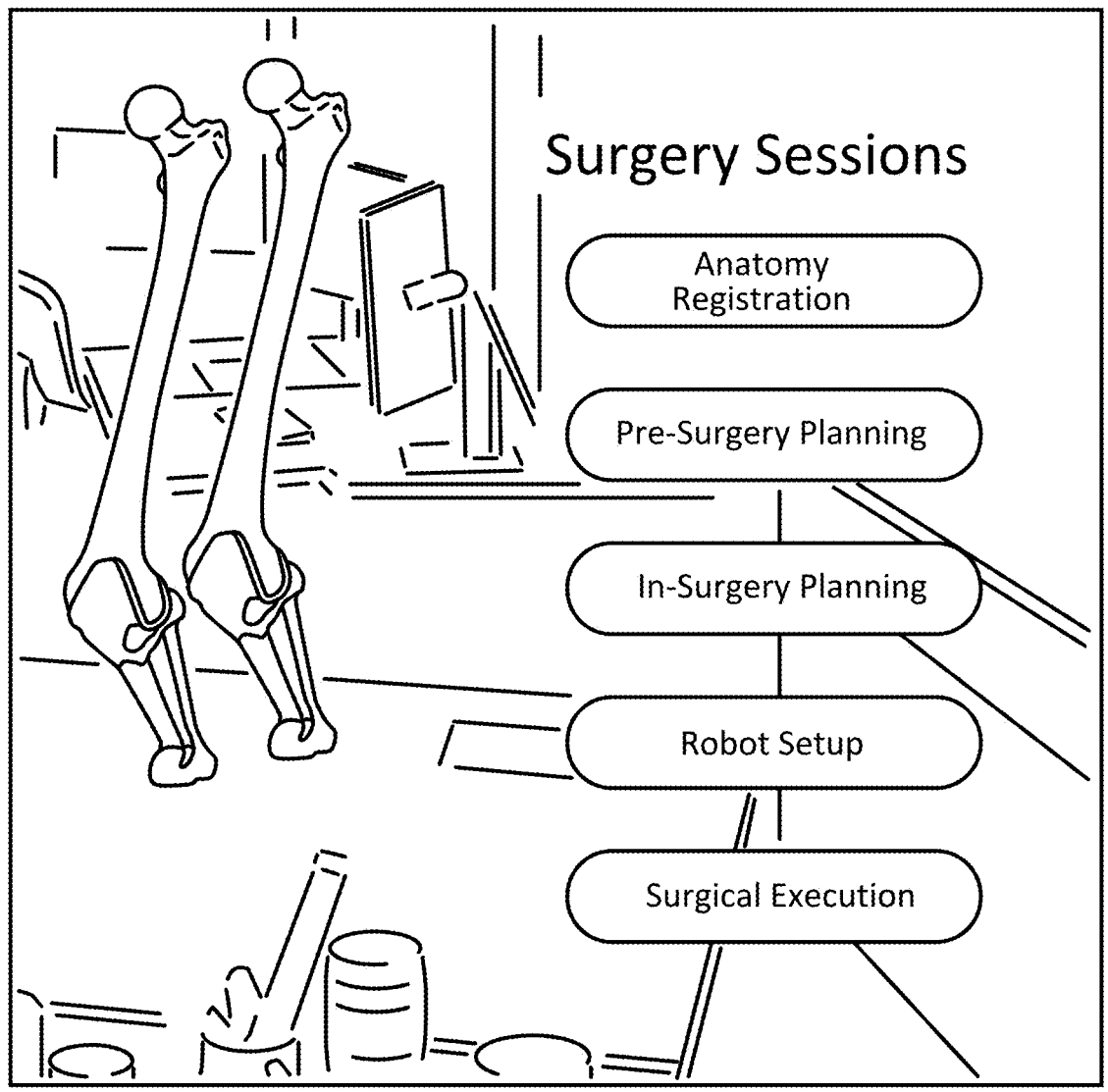
FIGS. 43 and 44 show an interface that is presented to a user for selecting execution of various guiding modules.

FIG. 43 shows an interactive interface that is presented to a user of one of the head units 402A, 402B or 402C. A rendering of a body part of patient is shown rotating about a vertical axis in a left of the view. The rendering may be based on radiology data that may have been collected using a CT scanner as described with reference to FIG. 2 and may be supplemented with further images following execution of the surgical planning module 462 in FIG. 37 or any further data or changes that are detected with the real object detection devices 452. The right side of view includes a menu with options that are selectable to access the various guiding modules 440. A user may select the "Robot Setup" option to access the room setup module 458, the "Anatomy Registration" option to execute the anatomy registration module 460, the "Pre-Surgery Planning" option or the "In-Surgery Planning" option to execute the surgical planning module 462, or the "Surgical Execution" option to execute the surgical execution module 464. All these options are available to a single user using a single head unit.

Figure 44:
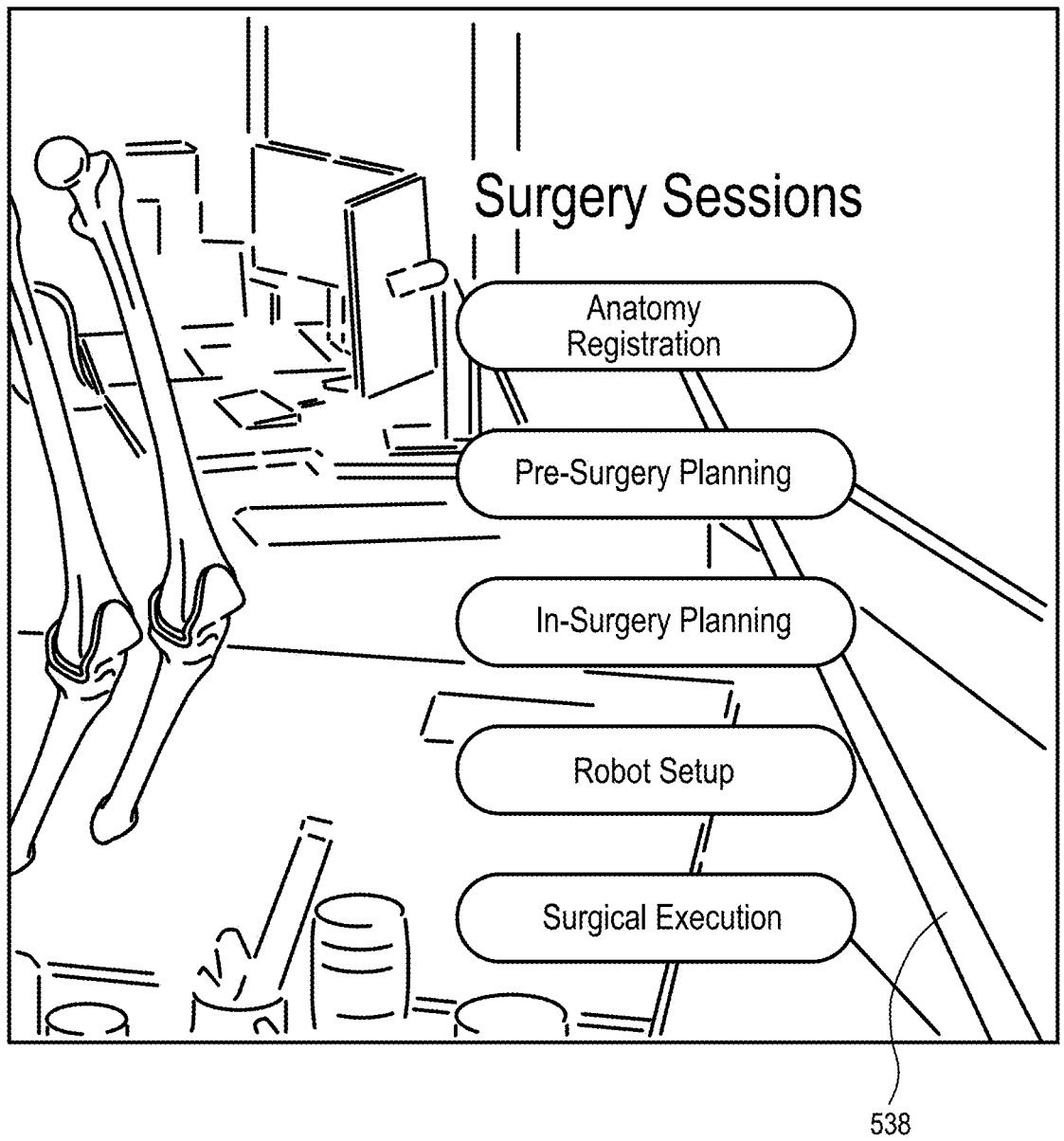

In FIG. 44, the user uses the handheld controller component 404 to make a selection. A selection wand 538 appears in the view of the user. The user can move the selection wand 538 to select one of the options. In the present example, the user selects the "Anatomy Registration" option. The user may, for example, tap on a thumb interface of the handheld controller component 404 to make the selection.

Figure 45:
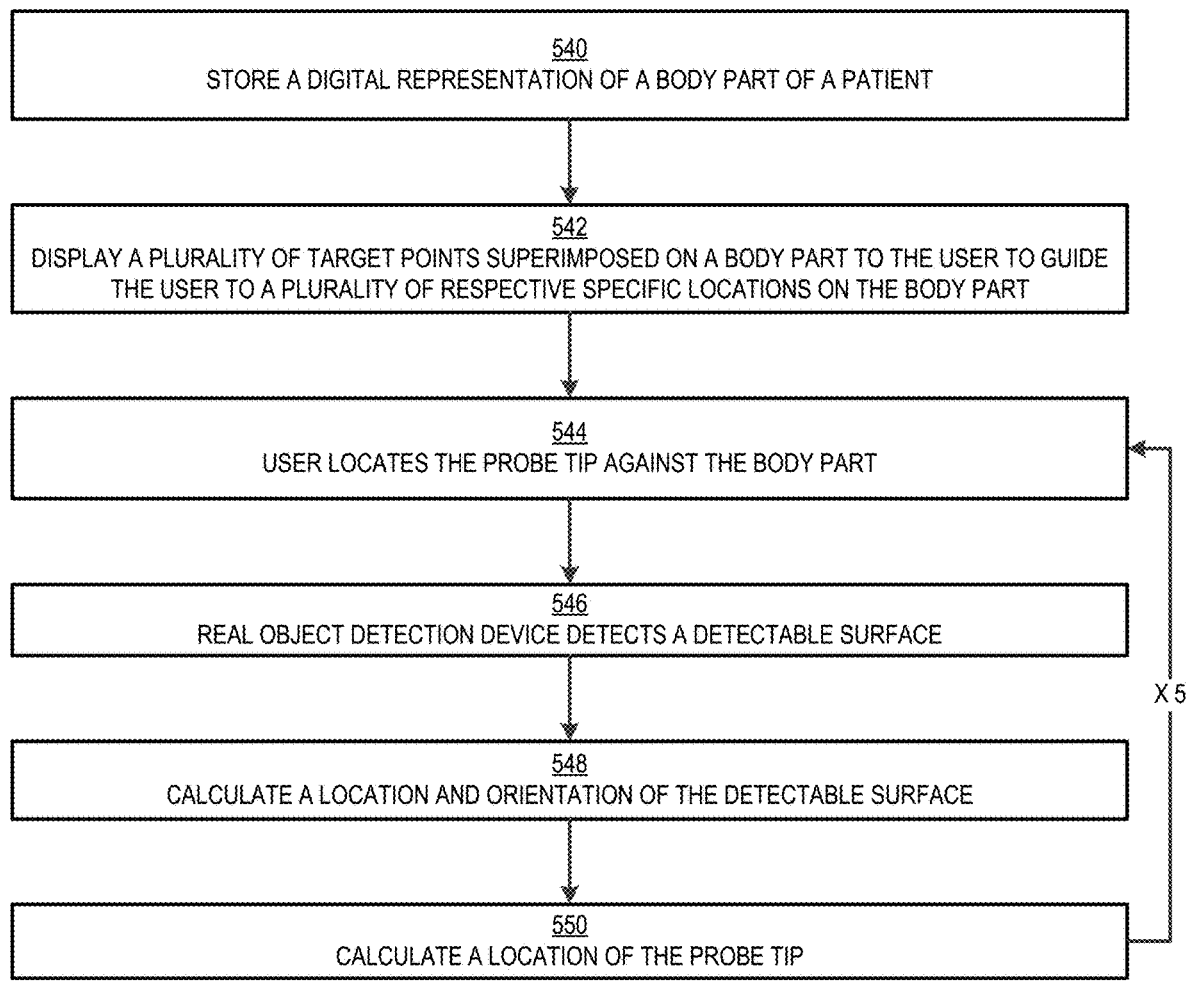
FIG. 45 is flow chart illustrating functioning of an anatomy registration module.

FIG. 45 illustrates the functioning of the anatomy registration module 460. At 540, a digital representation of a body part of a patient is stored. At 542, a plurality of target points are displayed to a user. The target points are superimposed on a body part to guide the user to a plurality of respective specific locations on the body part. At 544, the user locates a probe tip against the body part. At 546, one of the real object detection devices 452 in FIG. 37 detects a detectable surface. At 548, a location and orientation of the detectable surface is calculated. At 550, a location of the probe tip is calculated based on the location and orientation of the detectable surface. Steps 544 to 550 are repeated, for example five times for five target points.

Figure 46:
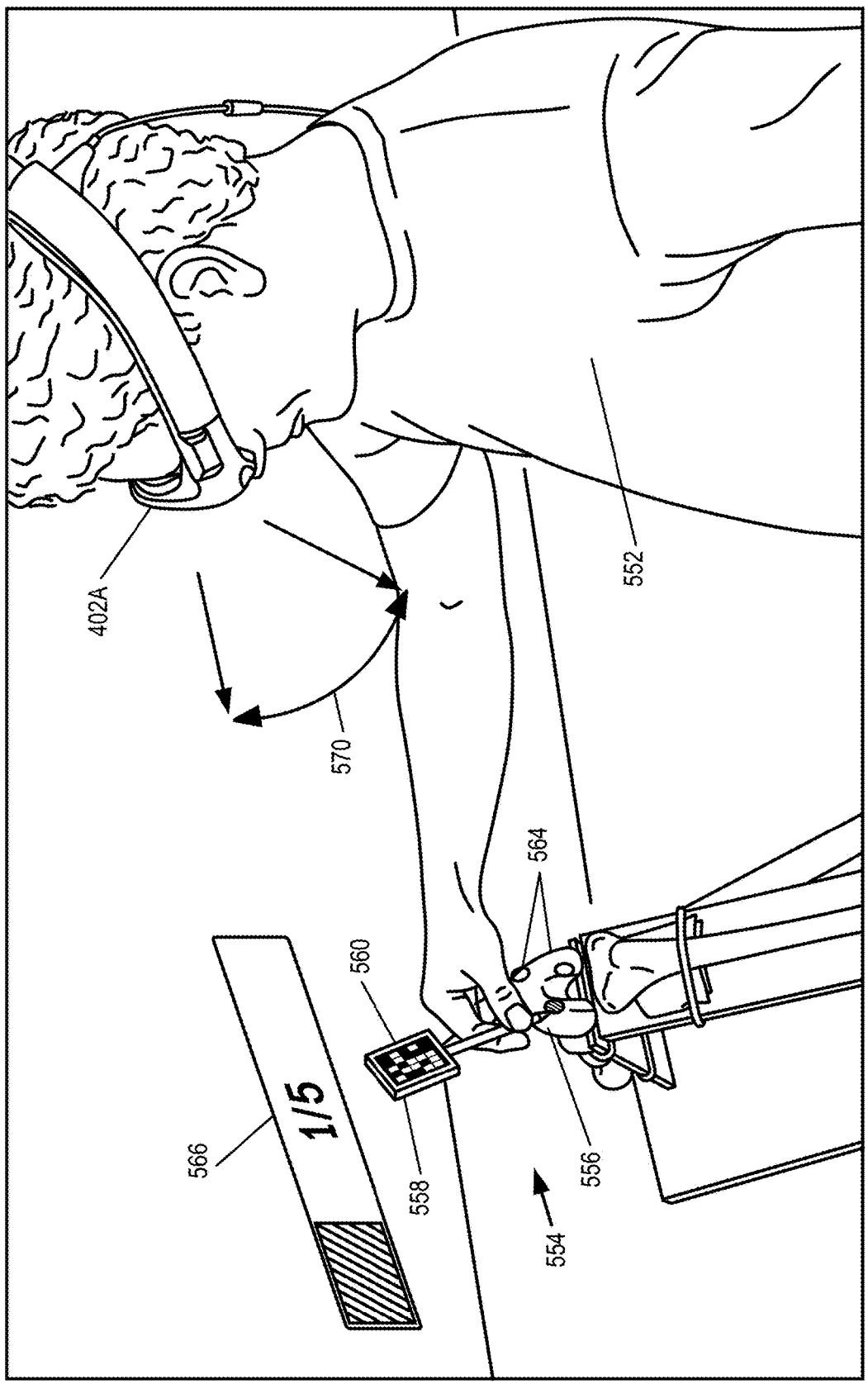
FIG. 46 is a perspective view showing a user using a probe to register points on an anatomy of a body part.

FIG. 46 illustrates the functioning of the anatomy registration module 460 in more detail. A user 552 wearing the first head unit 402A is holding a probe 554. The probe 554 has probe tip 556 and a reference object 558. The reference object 558 has a detectable surface 560. The detectable surface 560 has an image that is detectable by the head unit sensors 446 in FIG. 37.

Also shown is a body part 562 of a patient. The system presents and overlays five target points 564 on the body part 562. The user 552 is guided by the target points 564 and locates the probe tip 556 on each one of the target points 564. By detecting the detectable surface 560, the system can calculate a location of the probe tip 556 and precisely register five locations on the body part 562. The user is also provided with a visual output 566, which indicates to the user how many target points have been registered.

It should be noted that although the probe tip 556 moves and the canonical map 438 changes to reflect movement of the probe tip 556, it may also be possible that the body part 562 is not stationary and that the canonical map 438 changes in response to movement of the body part 562. Such movement of the body part 562 will primarily be recorded by the head unit sensors 446 of the head unit 402A because they span a field of view 570 that is within a direction that the user 552 is looking and the body part 562 is within the field of view 570.

Figure 47:
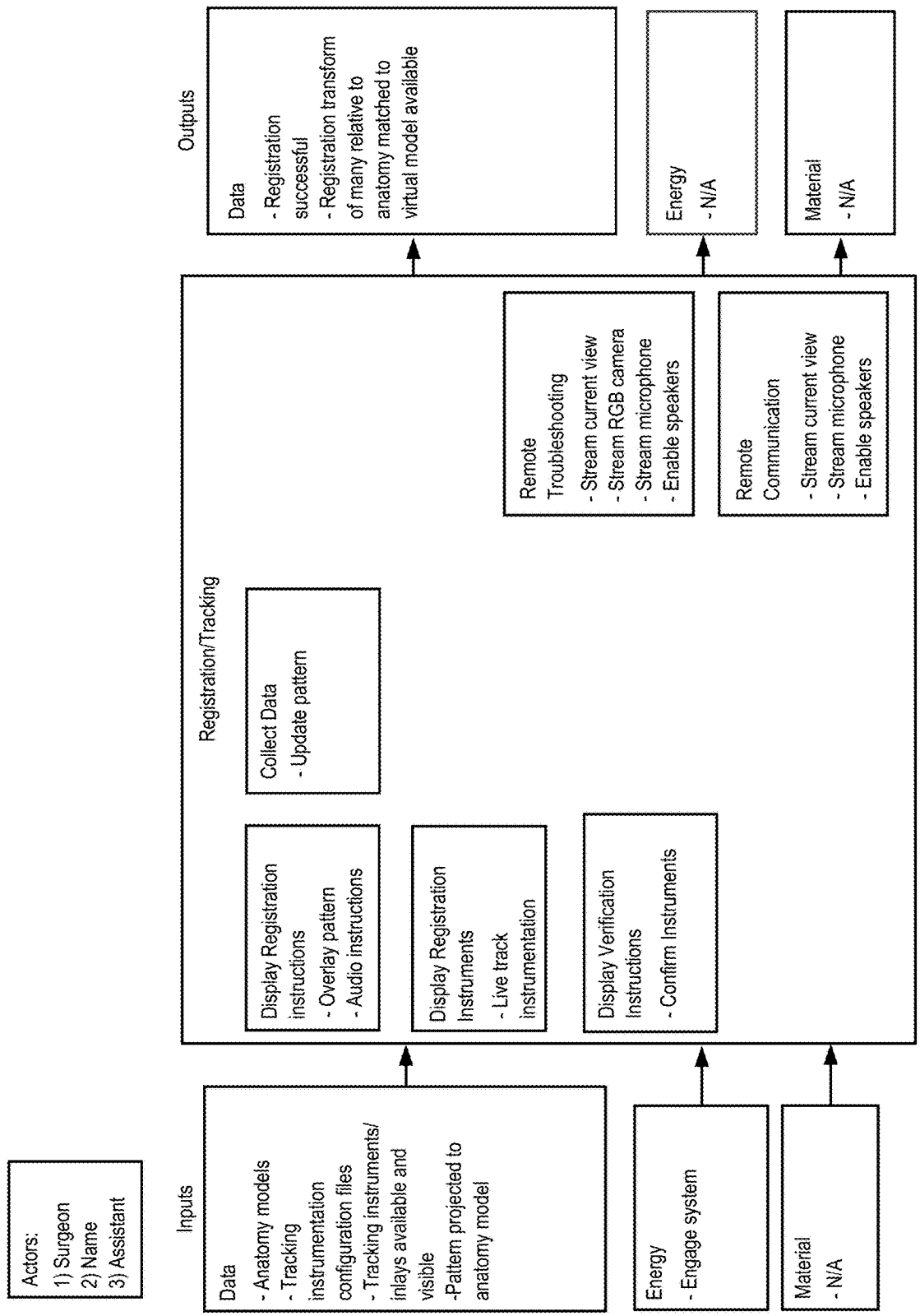
FIG. 47 is block diagram that illustrates various aspects of the anatomy registration module.

FIG. 47 illustrates various aspects of the anatomy registration module 460, including data input, data output, various actors, etc. The functioning of the anatomy registration module 460 has been described in the context of a user that facilitates registration of a body part. It should, however, be understood that registration may alternatively be executed entirely automatically, i.e., without user assistance using various sensors, computer vision and other mechanisms.

Figure 48:
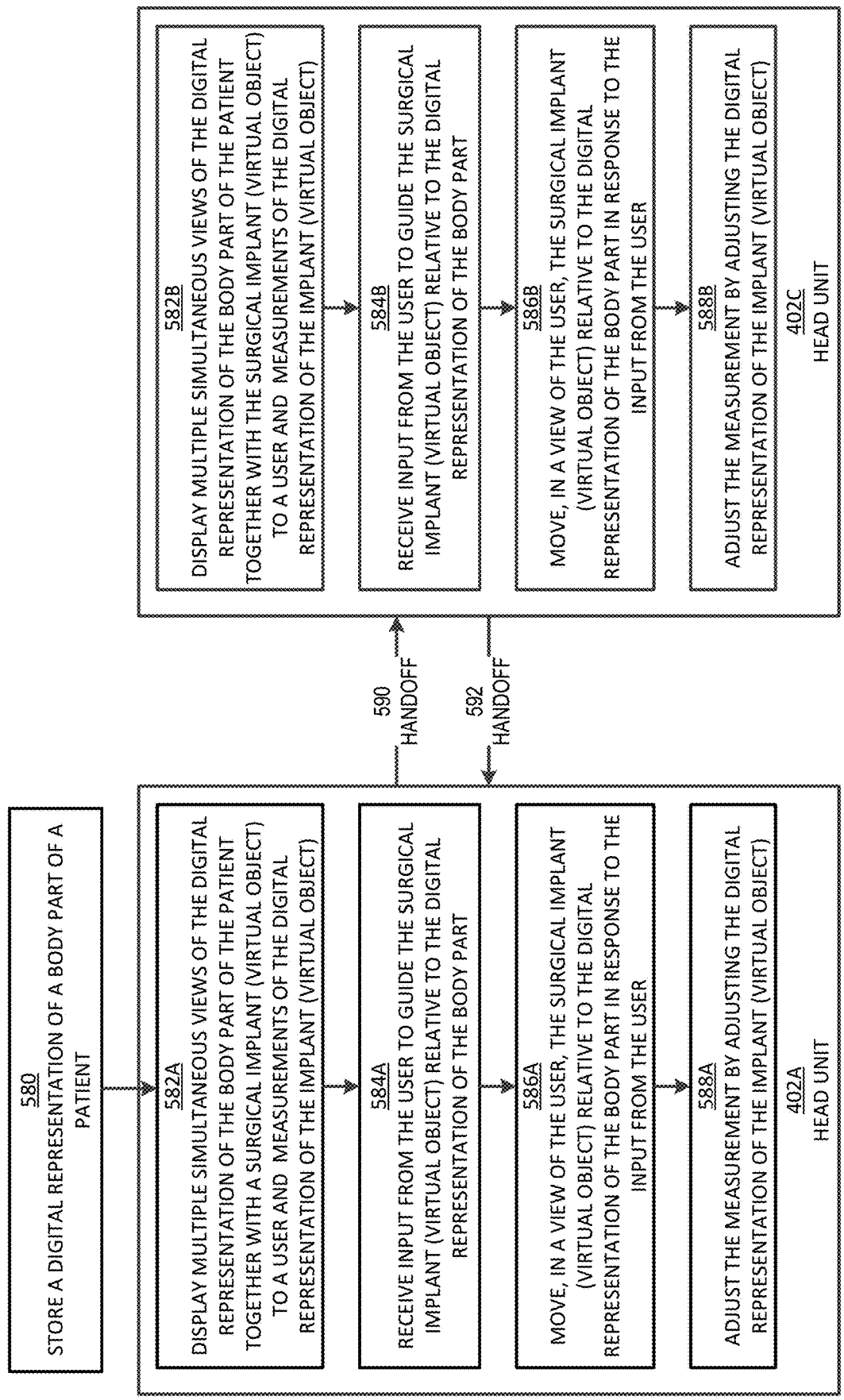
FIG. 48 is a flow chart illustrating the functioning of a surgical planning module.

FIG. 48 illustrates the functioning of the surgical planning module 462. At 580, a digital representation of a body part of a patient is stored. The digital representation that is stored at 580 may be the same digital representation that is stored at 540 in FIG. 45. At 582A, multiple simultaneous views are displayed on the head unit 402A. The views are different views of the digital representation of the body part of the patient together with a surgical implant (a virtual object) and measurements of the digital representation of the implant. At 584A, the user may provide an input that is received by the surgical planning module 462 to guide the surgical implant relative to the digital representation of the body part. At 586A, the surgical implant is moved in the view of the user relative to the digital representation of the body part in response to the input from the user. At 588A, the user may adjust the measurement by adjusting the digital representation of the surgical implant.

The user of the head unit 402A may at any time at 590 execute a handoff to a user of the head unit 402C. The user of the head unit 402C may then execute any one or more of steps 582B, 584B, 586B and 588B. The user of the head unit 402C may, at 592, execute a handoff to return control to the user of the head unit 402A.

Figure 49:
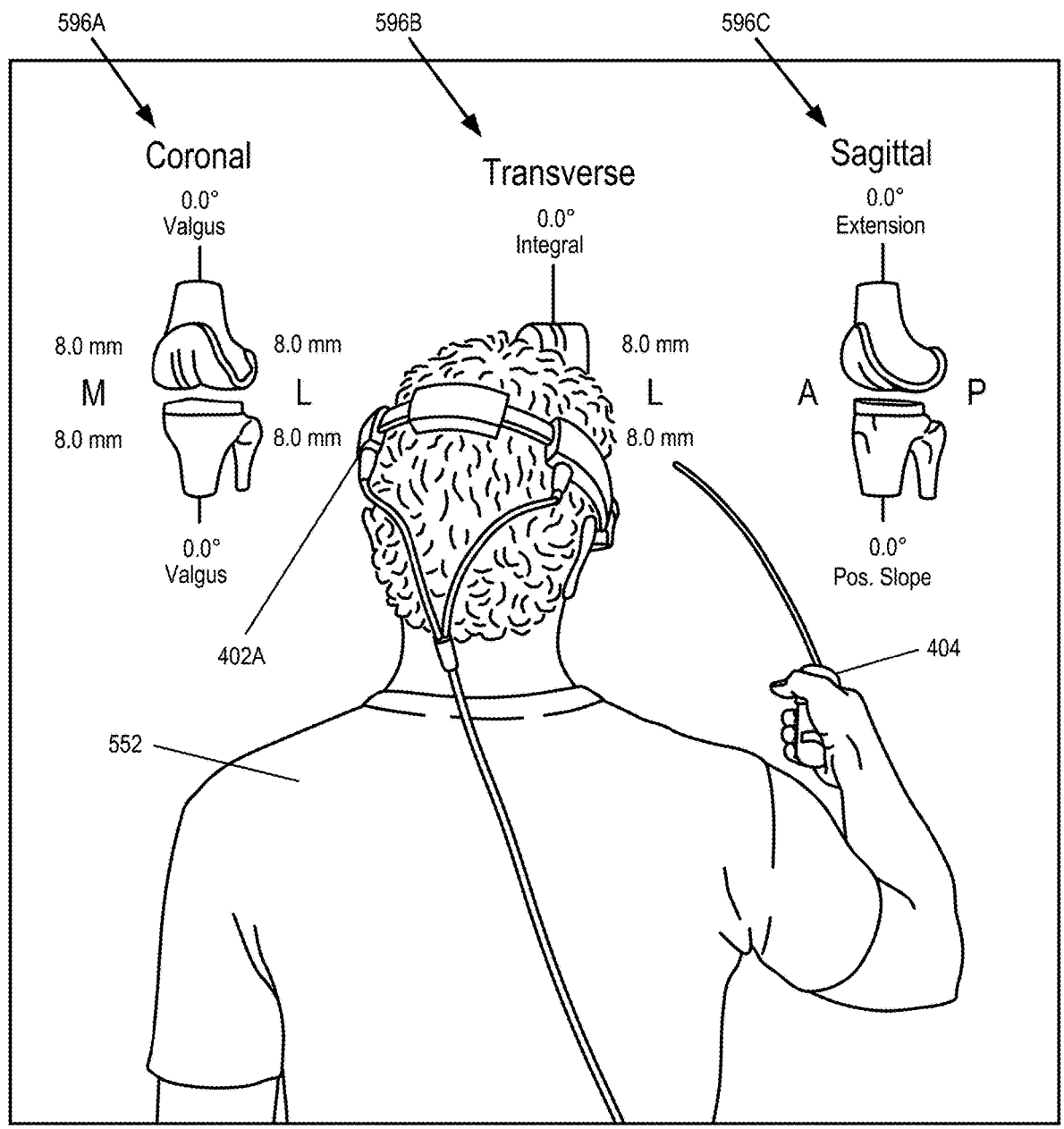
FIG. 49 is a front view of a user with a representation of a view that is seen by a user.

FIG. 49 shows the user 552 wearing the head unit 402A and using handheld controller component 404 thereof to view and manipulate three different views 596A, 596B and 596C. The three different views 596A, 596B and 596C represent a coronal, transverse, and sagittal view of a knee, respectively.

Figure 50B:
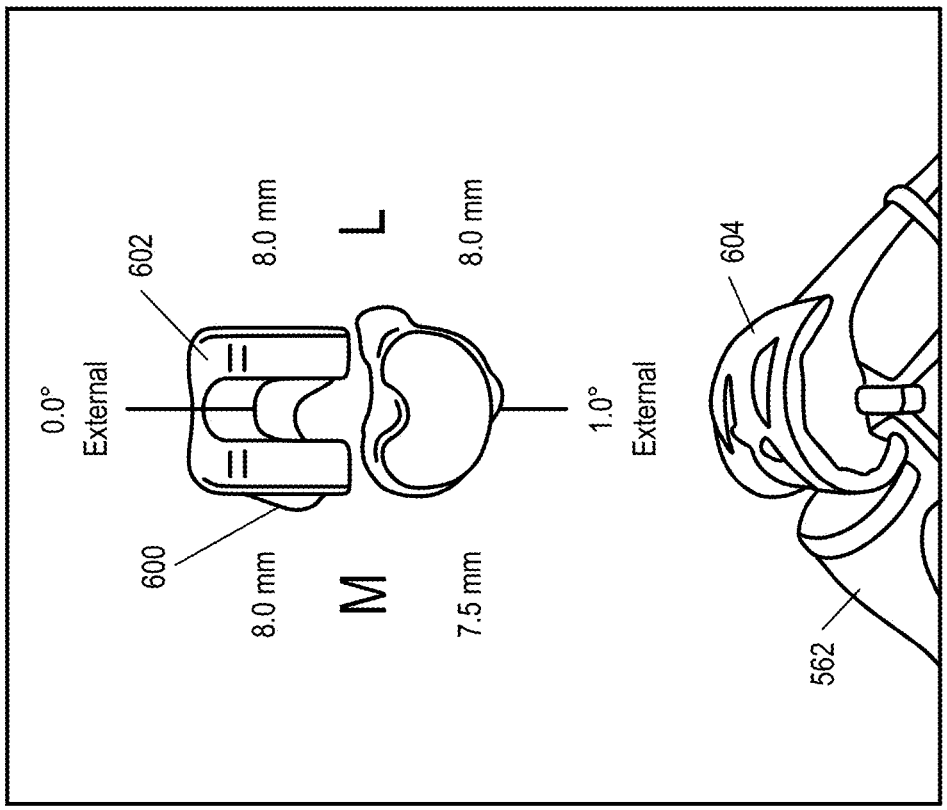
FIGS. 50a and 50b illustrate a portion of a view as seen through a head unit of the user when the user makes adjustments to an image of a digital representation of an implant.
Figure 50A:
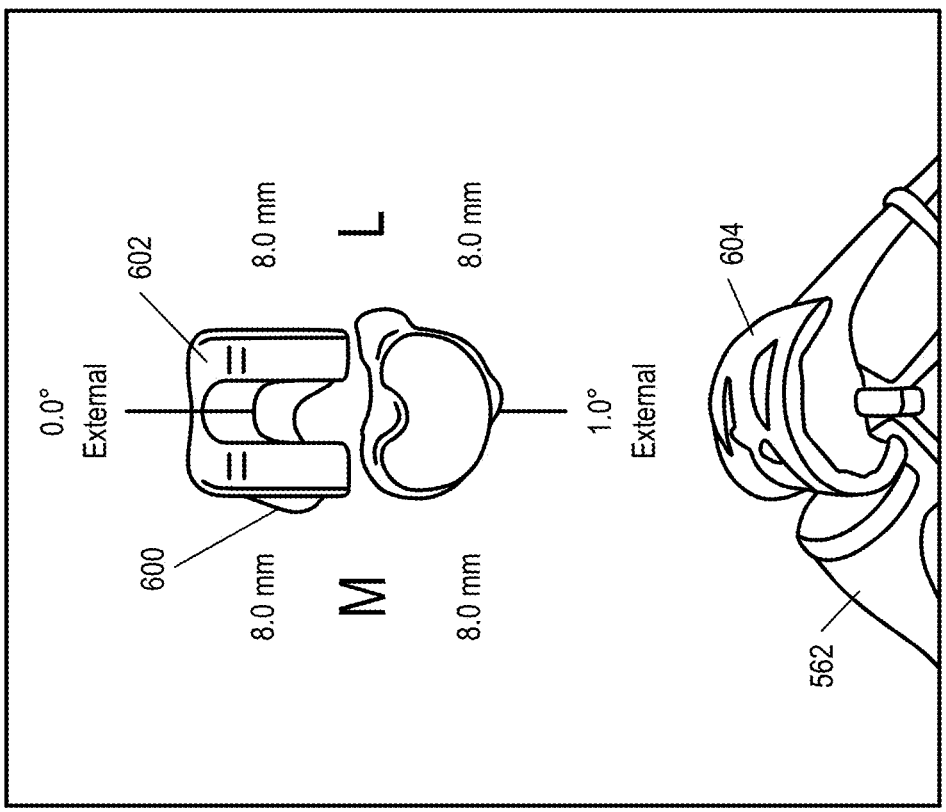

FIGS. 50a and 50b show one of the views as seen through head unit 402A by the user 552. The respective view includes a rendered view 600 of the digital representation of the body part and a rendered view 602 of the surgical implant. Because the head unit 402A is a see-through head unit, the user can also see the body part 562. A further rendered view 604 of the surgical implant is shown on the actual body part 562. The actual body part 562 is not cluttered with an additional rendering of the digital representation of the body part. The user can then adjust the surgical implant, for example by moving the rendered view 602 of the surgical implant. In the present example, movement of the rendered view 602 causes a change in a measurement from 8.0 mm to 7.5 mm.

Figure 51:
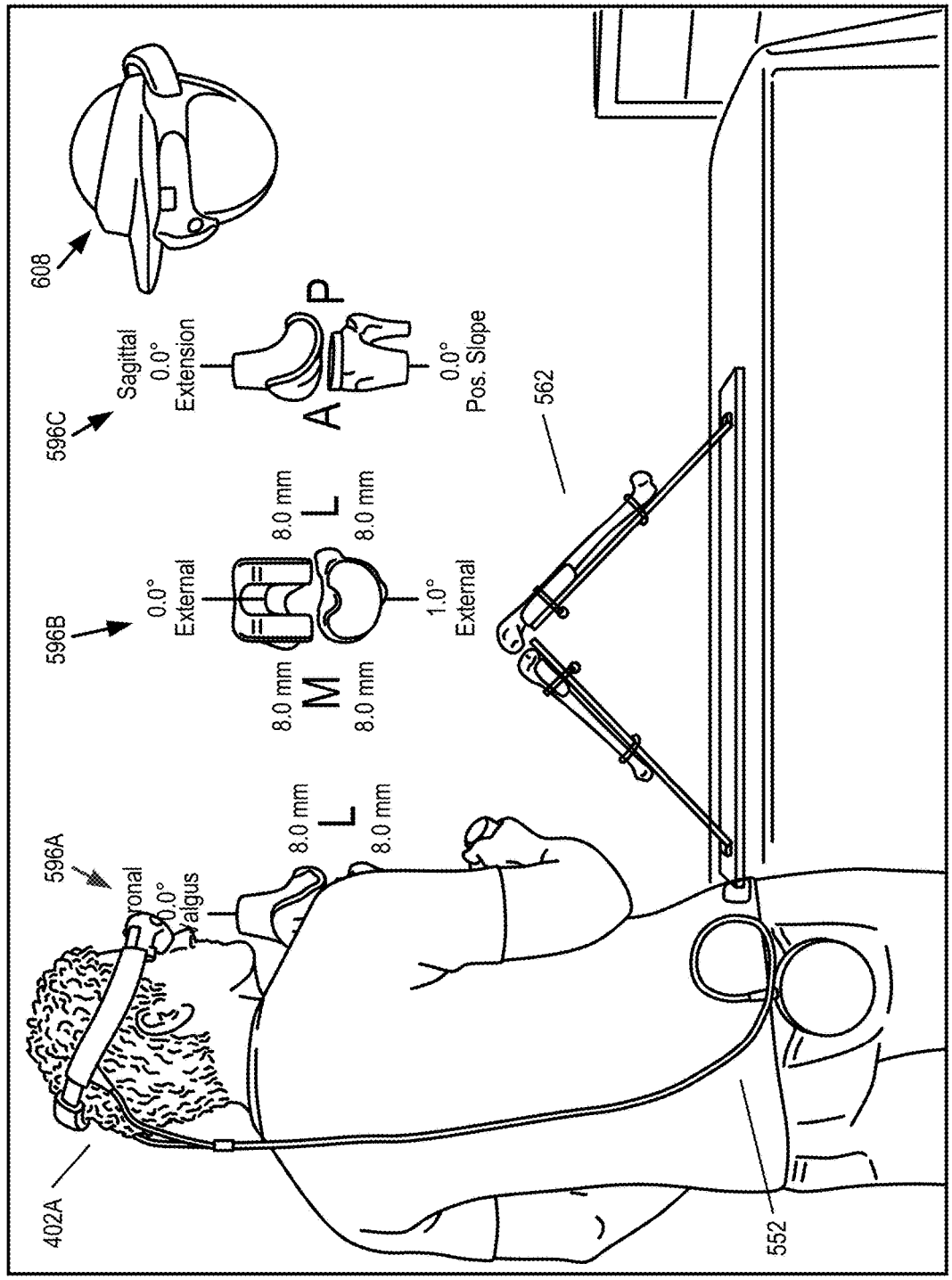
FIG. 51 is a view of the user interacting with a digital representation of a remote user.

FIG. 51 shows a rendered view 608 of the user of the head unit 402C. The user of the head unit 402C is located in a remote location. The user 552 can consult with the user of the head unit 402C. Both users can see each other in the same session as described with reference to FIG. 34 above and may hear each other from the appropriate location that they are located as described with reference to FIG. 31. The user represented by the rendered view 608 may also take over control from the user 552 as described with reference to FIG. 48.

Figure 52:
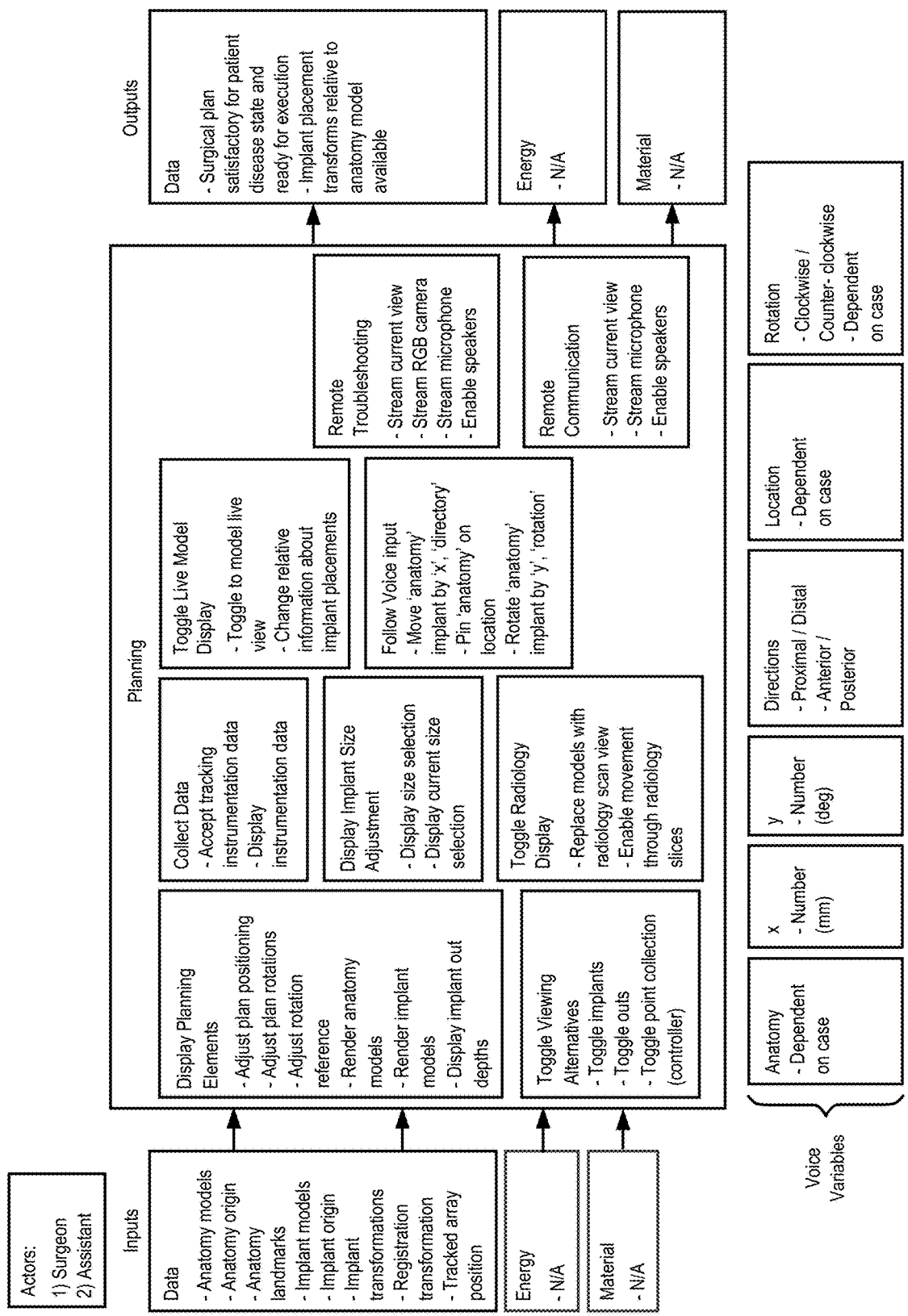
FIG. 52 is block diagram that illustrates various aspects of the surgical planning module.

FIG. 52 illustrates various aspects of the surgical planning module 462, including data input, data output, various actors, etc.

Figure 53:
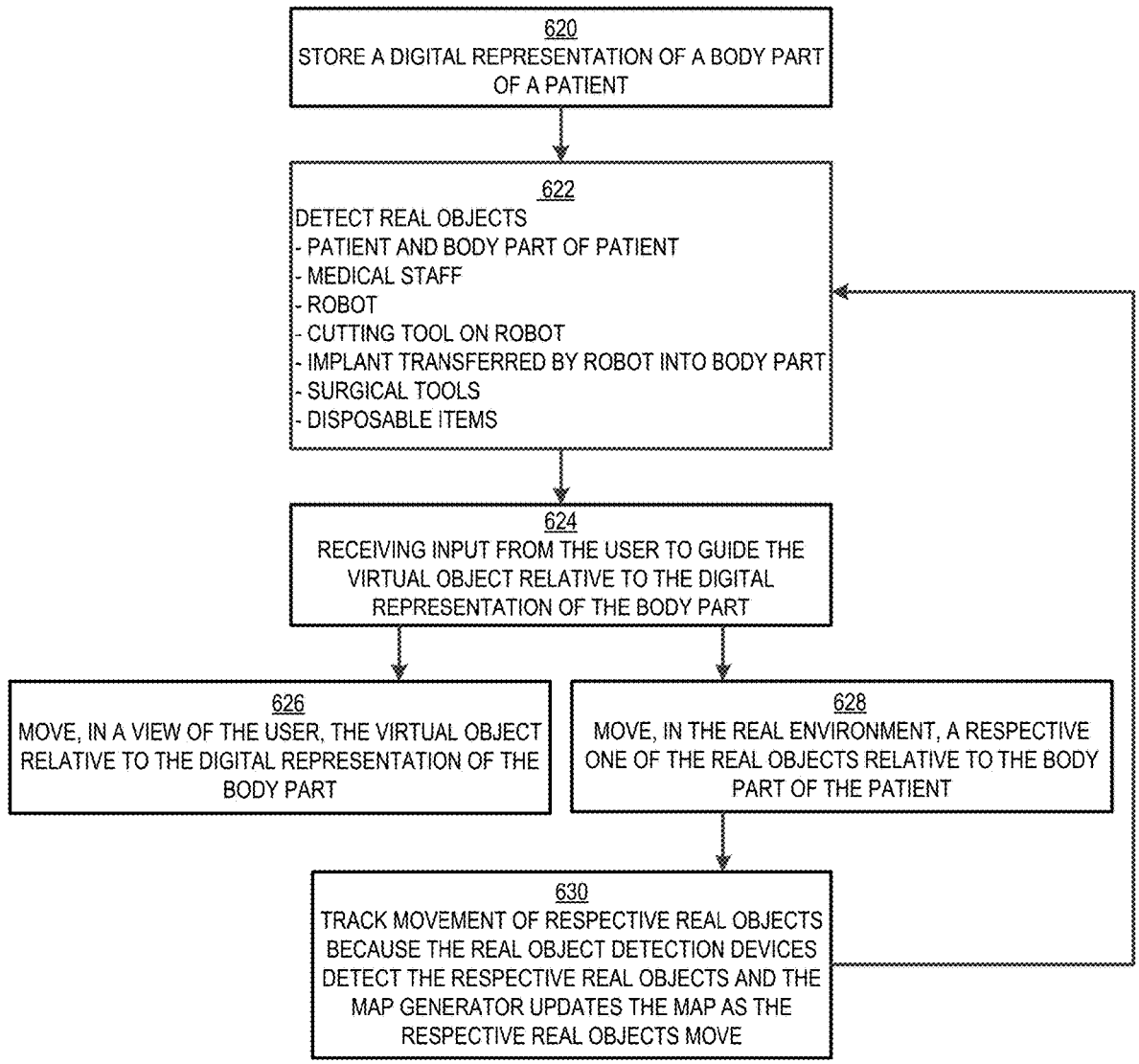
FIG. 53 is a flow chart illustrating functioning of a surgical execution module.

FIG. 53 shows the functioning of the surgical execution module 464 in more detail. At 620, a digital representation of a body part of a patient is stored as described above. At 622, real objects are detected by the various real object detection devices 452. The real objects that are detected include the patient and a body part of the patient, medical staff, one or more robots, a cutting tool on a robot, an implant transferred by the robot into the body part, surgical tools, and disposable items.

At 624, the system receives an input from the user to guide a virtual object relative to the digital representation of the body part. At 626, the virtual object is moved in a view of the user relative to the digital representation of the body part. It should be noted that the actual digital representation of the body part may not be rendered for viewing by the user. At 628, in the real environment, a respective one of the real objects is moved relative to the body part of the patient. At 630, all movements of the respective real objects are tracked because the real object detection devices 452 detect the respective real objects and the map generator updates the map as the respective real objects move.

Figure 54:
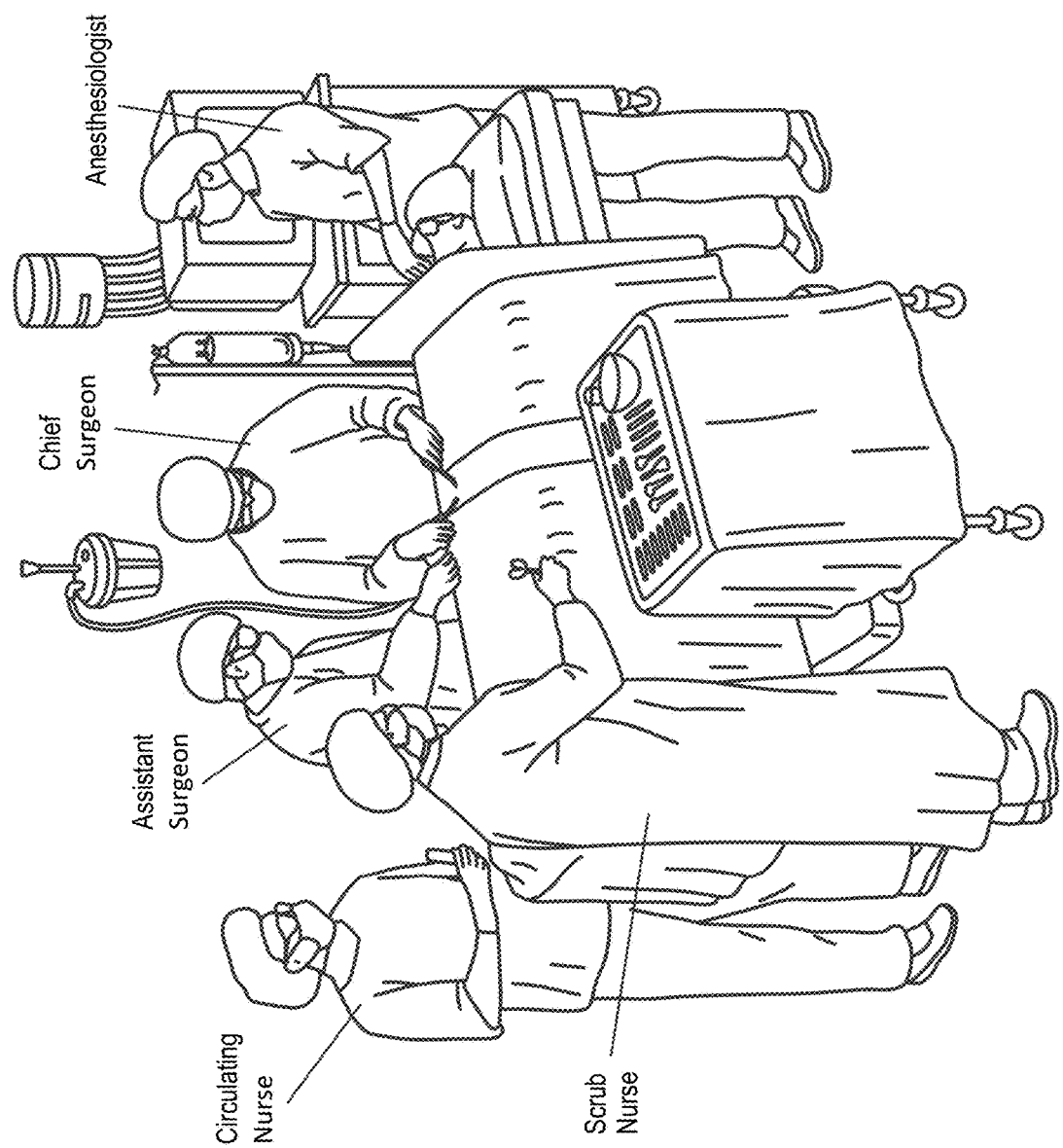
FIG. 54 is a perspective view of objects that are detected by real object detection devices, including various personnel.

FIG. 54 illustrates some of the real objects that are tracked by the real object detection devices 452, including the patient, various medical staff (Anesthesiologist, Chief Surgeon, Assistant Surgeon, Circulating Nurse, Scrub Nurse). Although not shown in detail, it will be appreciated that other real objects that may be tracked may include a body part of a patient, a robot, cutting tools of the robot, surgical implants, disposable items, surgical tools that are handheld, etc.

Figure 55:
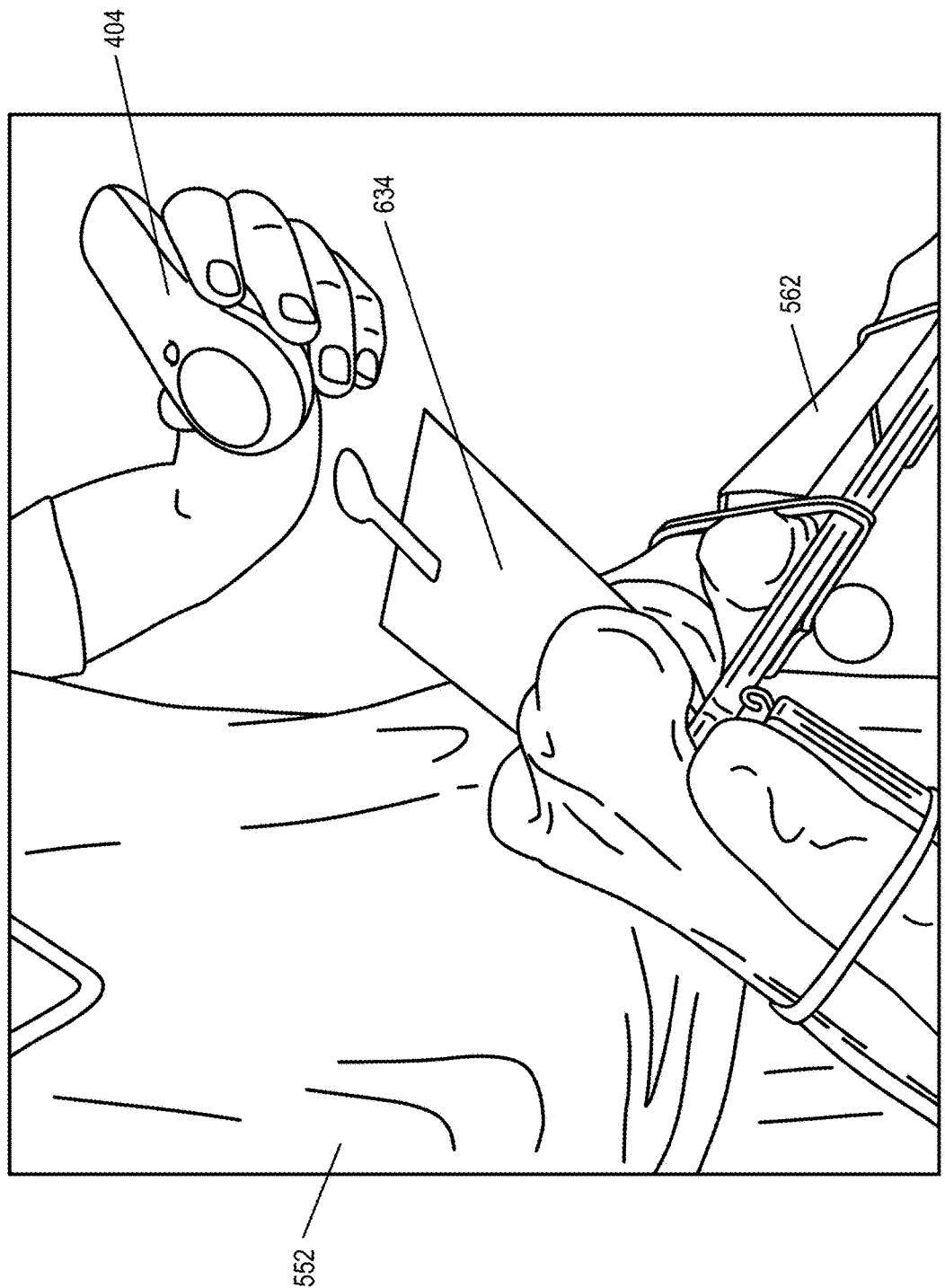
FIG. 55 is a perspective view showing a plane that presented to a user wherein the user sets a cutting plane for a robot.

FIG. 55 illustrates how the user 552 uses the handheld controller component 404 to plan and position a cutting plane of a cutting blade of the robot. A cutting plane 634 is displayed to the user 552 and the cutting plane 634 moves as the user 552 moves the handheld controller component.

Figure 56:
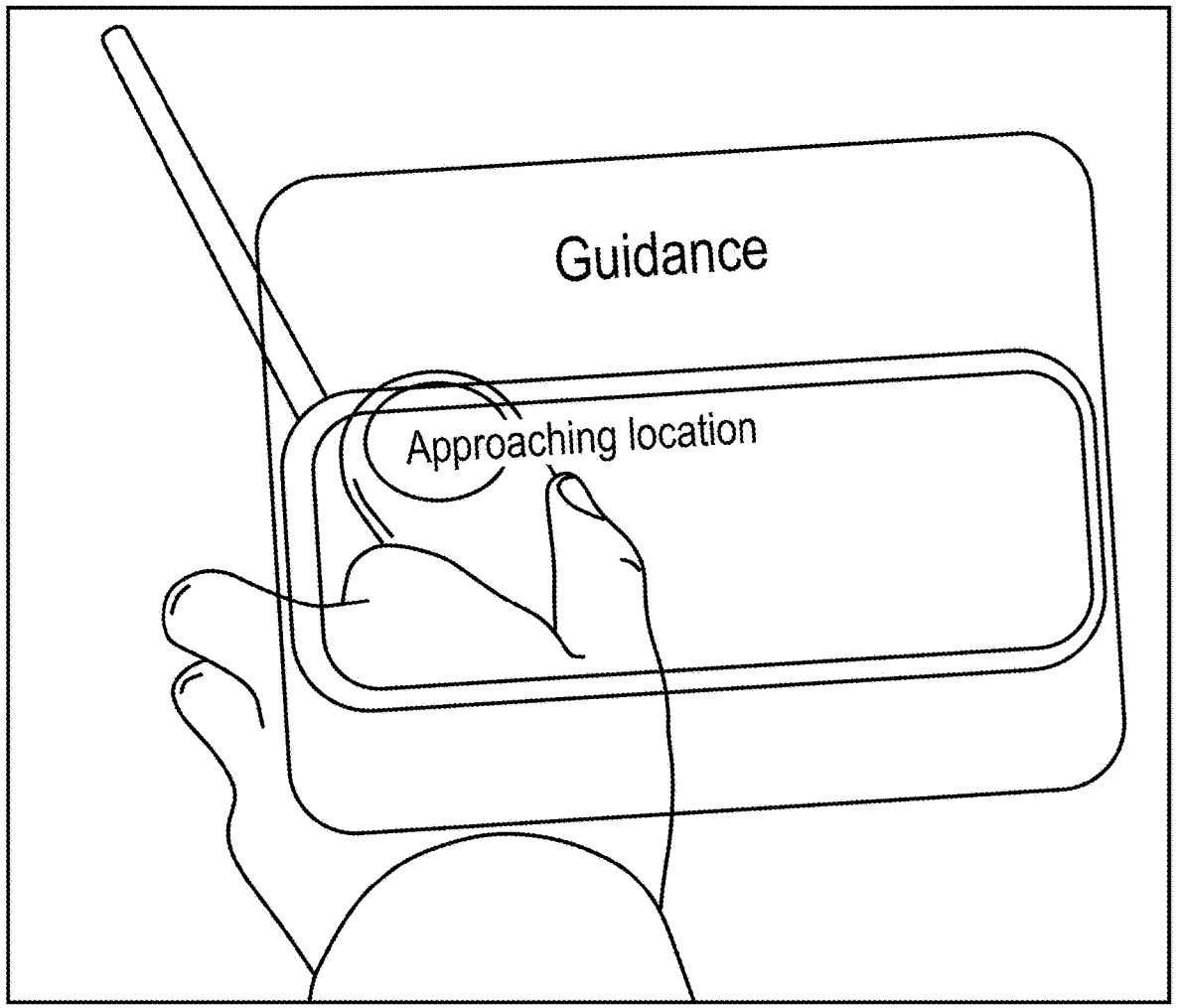
FIG. 56 is a menu item that is displayed to the user when the robot approaches a location that has been set by the user.

FIG. 56 displays a message that is shown to the user 552 when the cutting blade is approaching a desired location.

Figure 57:
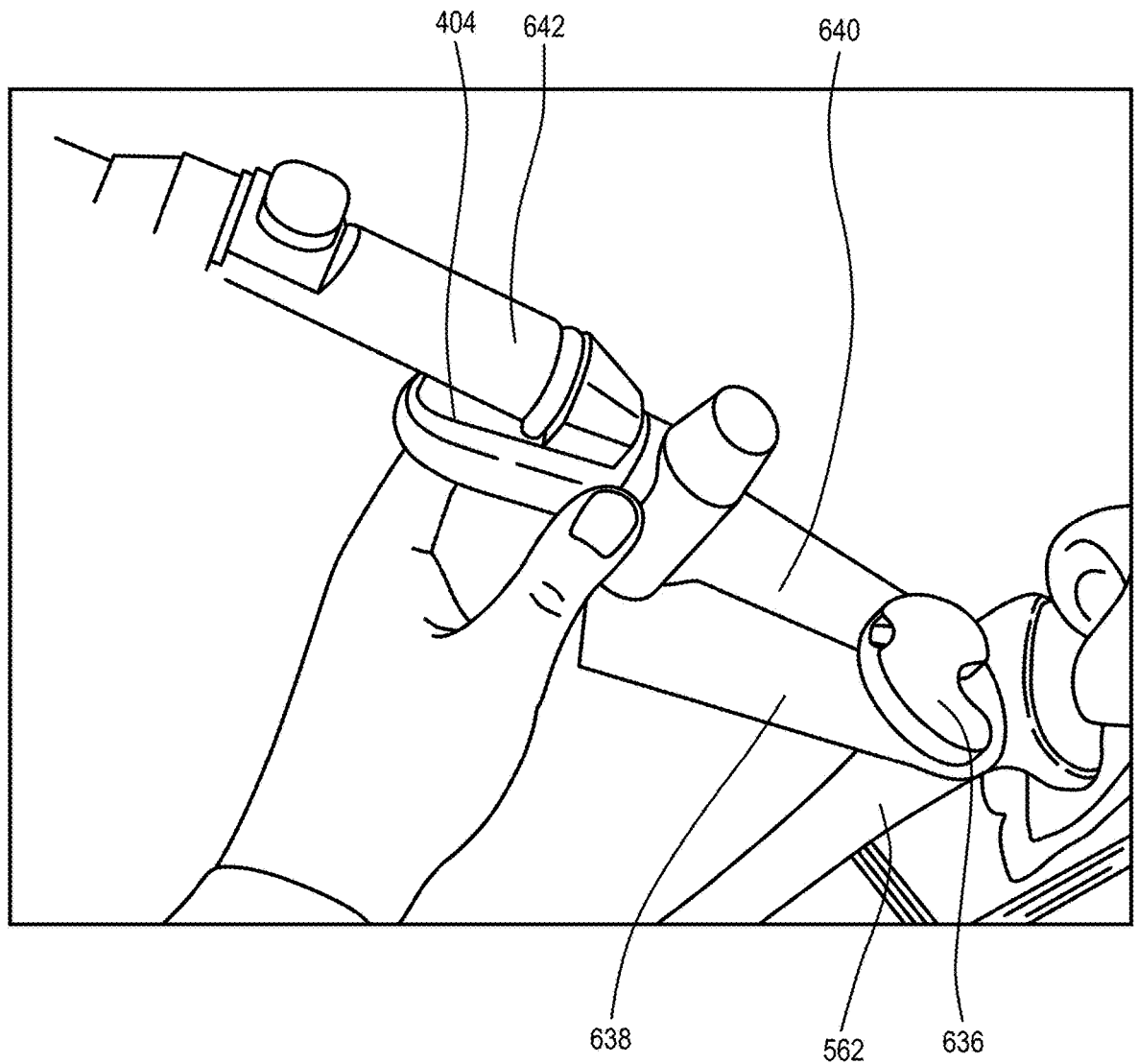
FIG. 57 illustrates a view that is presented to a user when the user sets the location of an implant.

FIG. 57 illustrates how the user 552 uses the handheld controller component 404 to select a placement of a rendering 636 of an implant. The user 552 is also provided with a visualization of a plane 638 of the implant 636, an end effector 640 and a robot arm 642.

FIGS. 58a, 58b and 58c may use a finger input surface of the handheld controller component 404 to move a robot arm so that a cutting tool or an implant is incrementally moved or rotated until it matches a desired location on the body part.

Figure 59:
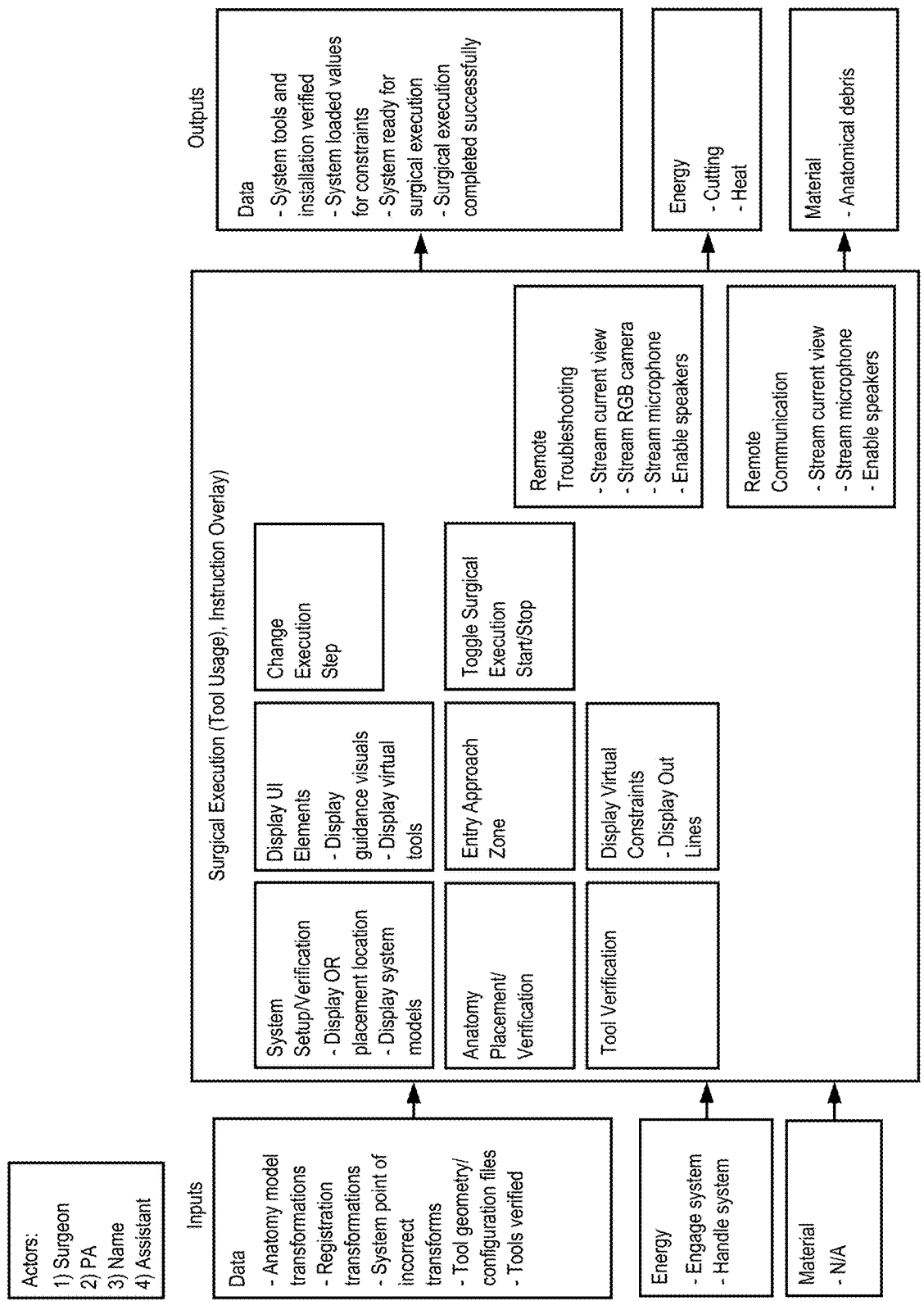
FIG. 59 is block diagram that illustrates various aspects of the surgical execution module.

FIG. 59 illustrates various aspects of the surgical execution module 464, including data input, data output, various actors, etc.

It should be evident from the above description that the digital representation of the real environment as represented by the canonical map 438 in FIG. 37 serves as a basis that the guiding modules 440 use to guide virtual objects and/or real objects. The digital representation is sometimes visible to a user and sometimes is not visible. The room setup module 458 does not display the digital representation of the canonical map 438, but instead displays target locations for objects. These target locations are, however, based on the digital representation in the canonical map 438 and the user is 100% digitally guided. Such digital guidance results in more accuracy and repeatability in a room setup. The anatomy registration module 460 does not display the digital representation of the canonical map 438, but instead displays target points that are based on the digital representation. When the user then locates the probe tip on the body part, the canonical map 438 can be very accurately updated, which makes the surgery more accurate. The surgical planning module 462 does display a digital representation of a body part. The digital representation of the body part may be acquired from radiology data that exists outside of the canonical map 438. However, after the body part has been registered using the anatomy registration module 460, the digital representation of the body part is based on the canonical map 438 and the visualization of the body part is based on the canonical map 438. Such a visualization of the body part, especially in its exact location within the canonical map 438, leads to more accurate planning of the surgery. The surgical execution module 464 uses the digital representation of the canonical map 438 to guide a robot without necessarily displaying a visualization of the canonical map 438 to a user. Because the canonical map 438 forms a digital twin of the real environment, the robot can be accurately guided based on the digital representation.

Spatial computing has many applications and use cases in the hospital. The following are a sampling of representative use cases where spatial computing can have the most impact. Many of them are interconnected and represent elements of a complete platform that can drive many clinical and operational transformations.

General—Training and Operations

Expert capture: On the fly training captured on device by an expert in a task or other workflow, and delivered on device to workers and clinical staff as needed.

Remote Assist: Bring in remote experts through video, avatar, or 3D rendering to provide remote assistance. This virtual visit can also include sharing digital content in 3D, placement of objects in a dedicated room (for reuse) and customized views to replace screens and physical information. This can also be used to support clinical work such as a specialist consult from another facility, a medical device expert providing supporting to facilitate a procedure being conducted using their device or remote technical support and applications training. This same capability can be used to augment field service engineers with a "can you see what I see" back to an operations center, overlay of documentation and schematics, identification of parts and components, etc.

Medical simulation: Current medical simulation implementations require large amounts of physical real estate and props. Simulations using location based spatial computing can leverage a smaller physical footprint and minimal props, allowing a smaller overall space to be used for multiple scenarios. In this use case a "blank room" can be filled with digital content, adaptive and reactive simulation scenarios can be delivered via the device, and student performance can be measured and tracked using the onboard sensors. Simulations and performance can be played back to the student for further understanding and review with instructors.

Physical Plant Design: Use the device to map, plan and visualize new construction or renovation in 3D, this includes operating room design with placement of devices and equipment for optimal workflow and throughput.

Tumor Board/Expert Consult: Expert panels from various geographic locations can come together as an avatar or 3D rendering in a virtual room and view a variety of 3D and other content. Content can be retained in the room and reviewed again later, including with the patient.

Hospital Services and Patient Engagement

Patient Consultation: Patients can receive remote consultation (at home, in a clinic, in a local doctor's office) with their specialist (at a hospital) prior to surgery or other procedures to be conducted at a hospital. Pre-surgery, the consultation can include 3D visualization of the patient's condition using radiology images, a walkthrough of the anatomy and discussion about the surgical approach with their surgeon. This can be done in a remote clinic, connected to a main hospital.

Informed Consent: Informed consent and patient education can be delivered on device, including pre-surgical 3D visualization, explanation of procedure, explanation of risks and benefits. The consultations can be recorded and documented for future use, including patient and family education, legal documentation.

Data Visualization: Spatial computing presents many opportunities to take electronic health records and other clinical and administrative data and leverage 3D spatial visualization for better integration of data sources, new ways of understanding those data and thus facilitating new insights.

Operating Room ("OR") and Interventional Suite Integration

Augmented Assistant: Use the device to provide virtual instructions and guidance to accomplish all clinical workflow steps, reduce physical interactions with software and hardware, through intuitive human interface improvements, facilitate independent troubleshooting for most issues commonly resolved through human to human interactions. This can make workflows more standardized, more accurate and can help reduce the overall amount of personnel required to physically be present in the room. The same underlying capability can be used for a virtual surgical checklist, including a full walk through and documentation.

Pre-Surgical Planning: Traditional 2D images can be ported to 3D spatial for enhanced visualization and collaboration with others who are able to see what you see from where you see it, ultimately replacing physical monitors and screens throughout the hospital and in doctor's offices and clinics. The first manifestation of this is a digital imaging and communications in medicine (DICOM) viewer that can be used to take models from a 2D surgical planning workstation and move the entire experience into the Magic Leap device, with the ability to join multiple people into a single session, view segmentation and scroll through multiple slices, adjust the size of the image for better visualization, etc. Images can be annotated and recorded. Surgeons can plan and practice their approach and visualize potential areas of complication, that may otherwise be difficult or impossible to see in 2D.

Registration, Planning and Execution: Radiology images and models can be registered to physical anatomy for enhanced planning and preparation, including anatomy, implant and robot placement and alignment. This also includes anatomy identification, landmark capture guidance, incision guidance and registration points overlay. During surgery execution the device could provide guidance, tissue interference detection, assembly instructions, and cut selection advancement.

Device Control: Use the device along with the control or other input mechanisms such as eye tracking, hand gestures, voice commands, etc. to control medical devices like surgical robots, surgical lights, surgical beds, and other tools.

Screenless Display: Provide on device displays of feeds from a variety of medical devices, either in the operating room, patient room or other areas of the hospital. This allows surgeons, clinical workers, and other staff, to bring in multiple feeds into one optimized display. This reduces the overall number of monitors and allows for more ergonomic viewing of data. Displays on device can be customized based on individual user preferences or based on more specific use cases, providing the optimal virtual cockpit.

Live video: Live video feeds from a variety of sources could be visualized through the device, including stored and live ultrasound images, endoscopy images, microscopy images. This video can be overlayed on top of other clinical content.

Digital Twin: Full digital twins can be created of individual rooms or the whole hospital. This will allow for tracking of objects, understanding and optimizing workflows and providing AI-driven augmentation of workers and workflows. This will serve as the base for a broader IoT implementation that will allow equipment control and manipulation through the device. Other use cases include markerless tracking of instruments and tools with visual depictions of tracked markers, better overall placement of devices and equipment as well as enhanced training, instrument labeling and setup, inventory management/asset tracking. Coupled with AI and other IoT sensors at the edge, this can provide real time workflow optimization and correction.

Radiation Therapy

Patient Positioning: Expand current patient positioning tools to include overlays on top of patient anatomy and ongoing monitoring and visualization of patient position.

Equipment Positioning: Accurate positioning of device and/or table using digital overlays and ongoing monitoring and visualization.

Telehealth, Patient Diagnostics and Therapies

Biomarkers: The device can be used to measure a variety of biomarkers including: eye movement, pupil size, gait, balance, eye/hand/finger coordination, and in the future a variety of respiratory and cardiac measures.

Neurology and Ophthalmology: Using some of the biomarkers, clinical studies are being conducted to validate diagnostic tests related to neuro-psychological conditions, including concussion, vestibular disorders, anxiety, PTSD, and other neuro-psychological conditions.

Neuro-muscular: Using some of the biomarkers, clinical studies are being conducted to validate diagnostic tests, monitoring protocols and digital therapeutics related to a number of motor disorders or neurological, brain, nervous system or neurodegenerative disorders, such as Parkinson's disease.

Telehealth: Deliver virtual, distributed health visits leveraging biomarkers, external sensors and avatar or 3D volumetric communication tools. Some examples include: a patient in a remote clinic consulting with a specialist at an urban hospital, a patient in their home receiving a primary care visit, chronic disease monitoring or device-delivered support for physical therapy. This can extend to concierge medicine, medical tourism, or global expert consultation. It is also possible to set up small, multi-purpose "blank" rooms in clinics or retail locations that can then leverage digital content delivered via the device (coupled with a suite of external sensors) to transform and enable the delivery of a variety of digital health services.

Following completion of each surgery, a time-based recording of a change in the digital representation or "digital twin" of the entire surgery is stored in a database or data sore. Live data from all past surgeries grow into a live, dynamic database and data system that includes all prior and future surgeries and is used to then provide augmentation to the workforce during all cases. This data is also mapped to patient outcomes and other data about the patient and the surgery that can then help identify what during the surgery delivers a good outcome (why is a good surgeon a good surgeon, etc.). This database also informs synthetic training that is much more like a real-life experience and ultimately becomes the ongoing artificial intelligence (AI) driven "guidance" that surgeons and other clinical works can leverage in real time throughout the case.

Figure 60:
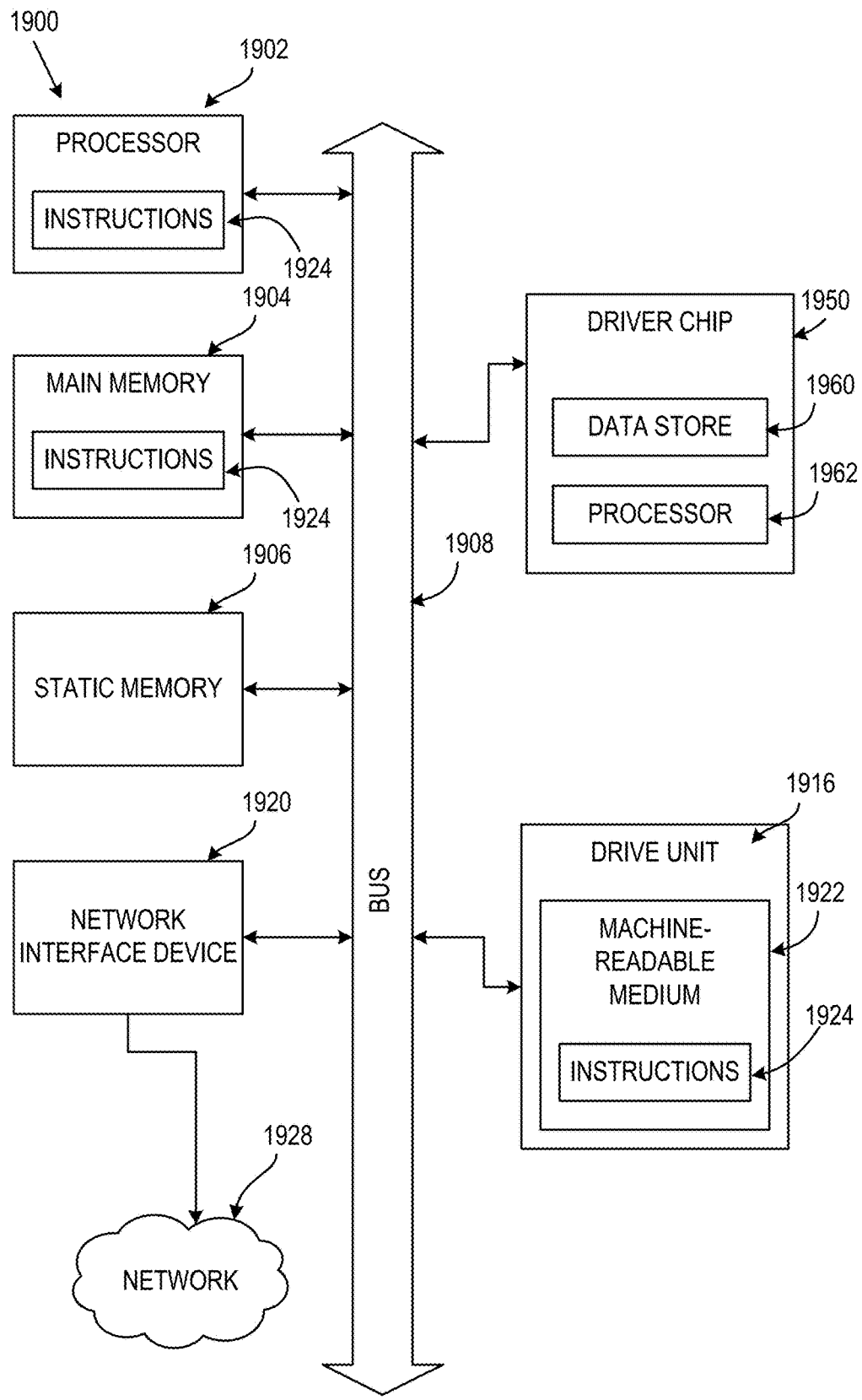
FIG. 60 is a block diagram of a machine in the form of a computer that can find application in the present invention system, in accordance with one embodiment of the invention.

FIG. 60 shows a diagrammatic representation of a machine in the exemplary form of a computer system 900 within which a set of instructions, for causing the machine to perform any one or more of the methodologies discussed herein, may be executed. In alternative embodiments, the machine operates as a standalone device or may be connected (e.g., networked) to other machines. Further, while only a single machine is illustrated, the term "machine" shall also be taken to include any collection of machines that individually or jointly execute a set (or multiple sets) of instructions to perform any one or more of the methodologies discussed herein.

The exemplary computer system 1900 includes a processor 1902 (e.g., a central processing unit (CPU), a graphics processing unit (GPU) or both), a main memory 1904 (e.g., read only memory (ROM), flash memory, dynamic random access memory (DRAM) such as synchronous DRAM (SDRAM) or Rambus DRAM (RDRAM), etc.), and a static memory 1906 (e.g., flash memory, static random access memory (SRAM), etc.), which communicate with each other via a bus 1908.

The computer system 1900 may further include a disk drive unit 916, and a network interface device1 1920.

The disk drive unit 1916 includes a machine-readable medium 1922 on which is stored one or more sets of instructions 1924 (e.g., software) embodying any one or more of the methodologies or functions described herein. The software may also reside, completely or at least partially, within the main memory 1904 and/or within the processor 1902 during execution thereof by the computer system 1900, the main memory 1904 and the processor 902 also constituting machine-readable media.

The software may further be transmitted or received over a network 1928 via the network interface device 1920.

The computer system 1900 includes a laser driver chip 1950 that is used to drive projectors to generate laser light. The laser driver chip 1950 includes its own data store 1960 and its own processor 1962.

While the machine-readable medium 1922 is shown in an exemplary embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform any one or more of the methodologies of the present invention. The term "machine-readable medium" shall accordingly be taken to include, but not be limited to, solid-state memories, optical and magnetic media, and carrier wave signals.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:

1. A viewing system comprising:
    a real object detection device positioned to detect locations of real objects in a real environment, the real objects including at least a plurality of objects that make up a layout of a room and are movable relative to one another;
    at least one processor;
    a computer-readable medium connected to the processor;
    a data store on the computer-readable medium;
    a set of instructions stored on the computer-readable medium and executable by the processor, including:
        a map generator connected to the real object detection device to receive data of the real environment including the real objects represented by at least the plurality of objects that make up the layout of the room and are movable relative to one another and executable to create a map that forms a digital representation of the real environment including the real objects represented by at least the objects that make up the layout of the room and are movable relative to one another;
        a map storing routine executable to store the map on the data store; and
        a guiding module connected to the data store to retrieve the map and executable to guide at least one of a virtual object and a real object based on the digital representation, wherein the guiding module is a room setup module that is executable by the processor to set the room up based on the digital representation, including:
    storing a desired room layout; and
    providing an output that superimposes the desired room layout digitally relative to the real environment, wherein the room setup module generates an image based on the desired room layout and superimposes the image over the real environment, wherein the room setup module generates an image of a desired placement of one of the objects that are movable relative to one another in the desired room layout and superimposes the image over the real environment, wherein the room setup module provides an output indicating that the respective object has been moved into a position to match the desired placement, wherein the room setup module tracks movement of the respective object because the object detection device detects the respective object, and the map generator updates the map as the respective object moves.

2. The viewing system of claim 1, wherein the room setup module provides a visual output indicating that the respective object has been moved into a position to match the desired placement by changing a color of the image of the desired placement.

3. The viewing system of claim 1, wherein the room setup module provides an output that superimposes the desired room teardown layout digitally relative to the real environment.

4. The viewing system of claim 1, wherein the room setup module tracks items that have been disposed of during surgery and provides an output of the items for replacement.

5. The viewing system of claim 1, further comprising:
    a viewing device that includes:
        a head unit comprising:
            a head-mountable frame;
            a data channel to receive image data of an image; and
            a light wave guide that is a transparent light wave guide positioned between an eye of a user and an external surface of the real object while light from an external surface of the real object transmits to the retina of the eye so that the user sees an external surface of the real object augmented with a rendering of the image that includes at least one object in the desired room layout.

6. The viewing system of claim 1, wherein the guiding module includes at least an anatomy registration module that is executable by the processor to execute anatomy registration based on the digital representation, including:
   storing a location of a body part of a patient, wherein the location of the body part is based on a location of a real object by the real object detection device.

7. The viewing system of claim 6, further comprising:
   a probe, the probe being the real object being guided and the probe having a probe tip and a detectable surface, wherein, when a user locates the probe tip against the body part, the real object detection device detects the detectable surface, wherein the anatomy registration module calculates a location of the probe tip based on a location of the detectable surface.

8. The viewing system of claim 7, wherein the anatomy registration module displays a target point superimposed on the body part to the user to guide the user to a specific location on the body part.

9. The viewing system of claim 8, wherein the anatomy registration module displays a plurality of target points to the user to guide the user to a plurality of respective specific locations on the body part and the anatomy registration module calculates respective locations of the probe tip based on respective locations of the detectable surface when the probe tip is at the respective specific locations.

10. The viewing system of claim 7, wherein the anatomy registration module calculates an orientation of the detectable surface and uses the orientation to calculate the location of the probe tip.

11. The viewing system of claim 8, further comprising:
    a viewing device that includes:
       a head unit comprising:
          a head-mountable frame;
          a data channel to receive image data of an image; and
          a light wave guide that is a transparent light wave guide positioned between an eye of a user and an external surface of the real object while light from an external surface of the real object transmits to the retina of the eye so that the user sees an external surface of the real object augmented with a rendering of the image that includes a rendering of the target point.

12. The viewing system of claim 1, wherein the guiding module includes at least a surgical planning module that is executable by the processor to plan a surgery based on the digital representation, including:
    storing a digital representation of a body part of a patient;
    displaying the digital representation of the body part of the patient together with the virtual object to a user;
    receiving input from the user to guide the virtual object relative to the digital representation of the body part; and
    moving, in a view of the user, the virtual object relative to the digital representation of the body part in response to the input from the user.

13. The viewing system of claim 12, wherein the user is simultaneously provided with at least two views of the digital representation of the body part.

14. The viewing system of claim 12, wherein the virtual object is a digital representation of an implant that moves into the digital representation of the body.

15. The viewing system of claim 14, wherein the surgical planning module displays a measurement of the digital representation of the implant and the measurement is adjustable by adjusting the digital representation of the implant.

16. The viewing system of claim 12, further comprising:
    a viewing device that includes:
       a data channel to receive image data of an image;
       a display connected to the data channel so that the user sees the image that includes the digital representation of the body part of the patient together with the virtual object; and
       a user input device though which the user provides the input to guide the virtual object.

17. The viewing system of claim 16, wherein the viewing device is a first viewing device, and the user is a first user, further comprising:
    a second viewing device that includes:
       a data channel to receive image data of an image;
       a display connected to the data channel so that a second user sees the image that includes the digital representation of the body part of the patient together with the virtual object; and
       a user input device though which the second user provides the input to guide the virtual object.

18. The viewing system of claim 17, wherein the surgical planning module displays a rendering of the second user in the display of the first viewing device.

19. The viewing system of claim 1, wherein the guiding module includes at least a surgical execution module that is executable by the processor to assist in executing a surgery based on the digital representation, including:
    storing a digital representation of a body part of a patient;
    receiving input from the user to guide the virtual object relative to the digital representation of the body part; and
    in response to the input from the user:
       moving, in a view of the user, the virtual object relative to the digital representation of the body part; and
       moving, in the real environment, a respective one of the real objects relative to the body part of the patient.

20. The viewing system of claim 19, wherein one of the real objects detected by the real object detection device is the body part of the patient.

21. The viewing system of claim 19, wherein one of the real objects detected by the real object detection device is a medical staff member.

22. The viewing system of claim 19, wherein one of the real objects detected by the real object detection device is a robot.

23. The viewing system of claim 19, wherein the real object that is a cutting tool that is moved into the body part of the patient.

24. The viewing system of claim 19, wherein the real object that is moved is an implant that is inserted into the body part of the patient.

25. The viewing system of claim 19, wherein one of the real objects detected by the real object detection device is a disposable item.

26. The viewing system of claim 19, wherein the surgical execution module tracks movement of the respective real object because the real object detection device detects the respective real object, and the map generator updates the map as the respective real object moves.

27. The viewing system of claim 1, further comprising:
    a head-mountable frame, the light wave guide being secured to the head-mountable frame;
    a raw data reception unit that receives raw data;
    an image generation unit connected to the data store to process the raw data of the return wave to create image data representing an image and store the image data in the data store;
    an image data reception unit that receives the image data from the data store;

at least one projector connected to the image data reception unit to receive the image data, the projector generating light in a pattern representative of the image data; and at least one light wave guide connected to the projector and secured to the head-mountable frame to guide the light to a retina of an eye of a user so that the user sees a rendering of the image data.

28. The viewing system of claim 1, further comprising:

a map storing routine to store a first map having a plurality of anchors, each anchor of the first map having a set of coordinates;

an anchor identification system connected to the real object detection device to detect, based on the locations of the real objects, anchors of a second map, each anchor of the second map having a set of coordinates; and a localization module connected to the first map and the second map and executable to localize the second map to the first map by matching a first anchor of the second map to a first anchor of the first map and matching a second anchor of the second map to a second anchor of the first map.

\* \* \* \* \*